United States Patent
Mueller et al.

(10) Patent No.: US 10,568,852 B2
(45) Date of Patent: Feb. 25, 2020

(54) COMBINATION COMPOSITIONS AND THEIR USE IN METHODS FOR TREATING OBESITY AND OBESITY-RELATED DISORDERS

(71) Applicant: Helmholtz Zentrum Munchen—Deutsches Forschungszentrum fur Gesundheit Und Umwelt (GMBH), Neuherberg (DE)

(72) Inventors: Timo Dirk Mueller, Munich (DE); Matthias Tschoep, Munich (DE); Christoffer Clemmensen, Munich (DE); Brian Finan, Indianapolis, IN (US)

(73) Assignee: HELMHOLTZ ZENTRUM MUNCHEN - DEUTSCHES FORSCHUNGSZENTRUM FUR GESUNDHEIT UND UMWELT (GMBH) (DE)

( * ) Notice: Subject to any disclaimer, the term of this patent is extended or adjusted under 35 U.S.C. 154(b) by 0 days.

(21) Appl. No.: 15/575,970

(22) PCT Filed: May 23, 2016

(86) PCT No.: PCT/EP2016/061514
§ 371 (c)(1),
(2) Date: Nov. 21, 2017

(87) PCT Pub. No.: WO2016/188932
PCT Pub. Date: Dec. 1, 2016

(65) Prior Publication Data
US 2018/0147163 A1    May 31, 2018

(30) Foreign Application Priority Data
May 22, 2015   (EP) .................................... 15168945

(51) Int. Cl.
| | | |
|---|---|---|
| *A61K 31/16* | (2006.01) | |
| *A61K 45/06* | (2006.01) | |
| *A61K 31/4439* | (2006.01) | |
| *A61K 31/513* | (2006.01) | |
| *A61P 1/16* | (2006.01) | |
| *A61P 3/04* | (2006.01) | |
| *A61P 3/06* | (2006.01) | |
| *A61K 31/40* | (2006.01) | |
| *A61K 31/438* | (2006.01) | |
| *A61K 31/46* | (2006.01) | |
| *A61K 31/465* | (2006.01) | |
| *A61K 31/55* | (2006.01) | |
| *A61P 27/02* | (2006.01) | |
| *A61P 19/02* | (2006.01) | |
| *A61P 9/12* | (2006.01) | |

(52) U.S. Cl.
CPC .............. *A61K 31/16* (2013.01); *A61K 31/40* (2013.01); *A61K 31/438* (2013.01); *A61K 31/4439* (2013.01); *A61K 31/46* (2013.01); *A61K 31/465* (2013.01); *A61K 31/513* (2013.01); *A61K 31/55* (2013.01); *A61K 45/06* (2013.01); *A61P 1/16* (2018.01); *A61P 3/04* (2018.01); *A61P 3/06* (2018.01); *A61P 9/12* (2018.01); *A61P 19/02* (2018.01); *A61P 27/02* (2018.01)

(58) Field of Classification Search
CPC ...... A61K 31/16; A61K 31/40; A61K 31/438; A61K 31/4439; A61K 31/46; A61K 31/465; A61K 31/495; A61K 31/513; A61K 31/55; A61K 45/06; A61P 19/02; A61P 1/16; A61P 27/02; A61P 3/04; A61P 3/06; A61P 9/12
See application file for complete search history.

(56) References Cited

U.S. PATENT DOCUMENTS

| | | | | |
|---|---|---|---|---|
| 8,058,243 | B2 * | 11/2011 | Tyers ................... | A61K 31/164 435/377 |
| 8,865,641 | B2 * | 10/2014 | Pavlov .................. | A61K 31/14 514/1.1 |
| 2005/0000529 | A1 | 1/2005 | Bereman et al. | |
| 2005/0123502 | A1 * | 6/2005 | Chan .................. | A61K 31/4439 424/78.3 |
| 2005/0181022 | A1 | 8/2005 | Cai et al. | |
| 2006/0057207 | A1 | 3/2006 | Ziegler et al. | |
| 2016/0361386 | A1 * | 12/2016 | Boss .................. | A61K 38/1825 |

FOREIGN PATENT DOCUMENTS

| | | |
|---|---|---|
| CN | 103284318 | 9/2013 |
| DE | 3645036 | 1/1989 |
| KR | 20100028182 | 3/2010 |

(Continued)

OTHER PUBLICATIONS

Amato et al., "Involvement of cholinergic nicotinic receptors in the menthol-induced gastric relaxation", 2014, European Journal of Pharmacology, vol. 745, pp. 129-134. (Year: 2014).*

(Continued)

*Primary Examiner* — My-Chau T. Tran
(74) *Attorney, Agent, or Firm* — Riverside Law LLP

(57) ABSTRACT

The present invention relates to compositions comprising at least two different active compounds and the use of such combination compositions in medicine, in particular in methods for treating obesity and obesity-related disorders and/or in methods for inhibiting weight gain.

7 Claims, 6 Drawing Sheets
(3 of 6 Drawing Sheet(s) Filed in Color)

(56) References Cited

FOREIGN PATENT DOCUMENTS

| KR | 20100069333 | | 6/2010 | |
|---|---|---|---|---|
| WO | WO-03037329 | A1 * | 5/2003 | ............. A61K 45/00 |
| WO | WO-2005117860 | A1 * | 12/2005 | ............. A61K 31/13 |

OTHER PUBLICATIONS

Clemmensen et al., "Coordinated targeting of cold and nicotinic receptors synergistically improves obesity and type 2 diabetes", 2018, Nature Communications, 9(Article No. 4304), pp. 1-13. (Year: 2018).*

Somm, Nicotinic Cholinergic Signaling in Adipose Tissue and Pancreatic Islets Biology: Revisited Function and Therapeutic Perspectives Arch. Immunol. Ther. Exp. (2014) 62:87-101.

Lupien J R et al: "Nicotine increases thermogenesis in brown adipose tissue in rats", Pharmacology Biochemistry and Behavior, Elsevier, US, vol. 29, No. 1, Jan. 1, 1988 (Jan. 1, 1988), pp. 33-37, XP025497879, ISSN: 0091-3057.

P. B. Martinez De Morentin et al: "Nicotine Induces Negative Energy Balance Through Hypothalamic AMP-Activated Protein Kinase", Diabetes, vol. 61, No. 4, Apr. 1, 2012 (Apr. 1, 2012), pp. 807-817, XP055299315, US, ISSN: 0012-1797.

S. Ma et al: "Activation of the cold-sensing TRPM8 channel triggers UCP1-dependent thermogenesis and prevents obesity", Journal of Molecular Cell Biology, vol. 4, No. 2, Jan. 11, 2012 (Jan. 11, 2012), pp. 88-96, XP055299244, ISSN: 1674-2788.

Allison C Hoffman: "The health effects of menthol cigarettes as compared to non-menthol cigarettes", Tobacco Induced Diseases, Biomed Central Ltd, London UK, vol. 9, No. Suppl 1, May 23, 2011 (May 23, 2011), p. S7, XP021 097967, ISSN: 1617-9625.

Sonali S. Bharate et al: "Modulation of Thermoreceptor TRPM8 by Cooling Compounds", ACS Chemical Neuroscience, vol. 3, No. 4, Apr. 18, 2012 (Apr. 18, 2012), pp. 248-267, XP055090754, ISSN: 1948-7193.

M. Hans et al: "Menthol Suppresses Nicotinic Acetylcholine Receptor Functioning in Sensory Neurons via Allosteric Modulation", Chemical Senses., vol. 37, No. 5, Jan. 25, 2012 (Jan. 25, 2012), pp. 463-469, XP055322365, GB, ISSN: 0379-864X.

Brian O'Neill et al: "Striatal Dopamine Release Regulation by the Cholinergic Properties of the Smokeless Tobacco, Gutkha", ACS Chemical Neuroscience, vol. 6, No. 6, Mar. 22, 2015 (Mar. 22, 2015), pp. 832-837, XP055322809, US, ISSN: 1948-7193.

Nadine Kabbani: "Not so Cool? Menthol's discovered actions on the nicotinic receptor and its implications for nicotine addiction", Frontiers in Pharmacology, vol. 4, Jan. 1, 2013 (Jan. 1, 2013), CH, XP055322533, ISSN: 1663-9812.

Journigan V Blair et al: "TRPM8 ion channel ligands for new therapeutic applications and as probes to study menthol pharmacology", Life Sciences, Pergamon Press, Oxford, GB, vol. 92, No. 8, Nov. 16, 2012 (Nov. 16, 2012), pp. 425-437, XP028986720, ISSN: 0024-3205.

Amato Antonella et al: "Involvement of cholinergic nicotinic receptors in the menthol-induced gastric relaxation", European Journal of Pharmacology, Elsevier Science, NL, vol. 745, Oct. 16, 2014 (Oct. 16, 2014), pp. 129-134, XP029107372, ISSN: 0014-2999.

Teichert et al., "Using constellation pharmacology to define comprehensively a somatosensory neuronal subclass," 2014, PNAS, 111(6):2319-2324.

* cited by examiner

A)

B)

C)

D)

A)

2 way-ANOVA Vhcl vs. Combo: p<0.05

2 way-ANOVA Combo vs. WS-12: p<0.05

2 way-ANOVA Combo vs. DMPP: p<0.001

B)

COMBINATION COMPOSITIONS AND THEIR USE IN METHODS FOR TREATING OBESITY AND OBESITY-RELATED DISORDERS

CROSS-REFERENCE TO RELATED APPLICATIONS

The present application is the U.S. national phase application filed under 35 U.S.C. § 371 claiming benefit to International Patent Application No. PCT/EP2016/061514, filed May 23, 2016, which is entitled to priority under 35 U.S.C. § 119(a)-(d) to European Application No. 15168945.2, filed May 22, 2015, all of which applications are incorporated herein by reference in their entireties.

TECHNICAL FIELD OF THE INVENTION

The present invention relates to compositions comprising at least two different active compounds and the use of such combination compositions in medicine, in particular in methods for treating obesity and obesity-related disorders and/or in methods for inhibiting weight gain.

BACKGROUND

The incidence of many debilitating diseases, especially obesity and its related disorders (such as diabetes and metabolic syndrome), is continuously increasing in industrialized countries, and, thus, represents not only a major health problem but also a growing socio-economic burden. Since lifestyle modification has not been proven effective, therapeutic strategies are required. However, potent and safe therapeutic strategies to combat these diseases are inadequate, in part since many previous startegies were directed at single molecular targets and, thus, resulted in insufficient efficacy. For example, orlistat, sibutramine, and liraglutide (brand names: Victoza and Saxenda), i.e., compounds used so far for treating metabolic syndrome or obesity, cause a series of severe side effects. In particular, the European Medicines Agency has reviewed the safety and effectiveness of sibutramine and came to the conclusion that the benefits of sibutramine do not outweigh its risks, and that all marketing authorisations for medicines containing sibutramine should be suspended throughout Europe (cf. "Questions and answers on the suspension of medicines containing sibutramine—Outcome of a procedure under Article 107 of Directive 2001/83/EC", EMA/808179/2009). Furthermore, the primary side effects of orlistat comprise steatorrhea, fecal incontinence and the inhibition of absorption of fat-soluble vitamins thereby forcing the patient who takes orlistat to (i) avoid foods with high fat content and (ii) separately take dietary supplements containing fat-soluble vitamins and other fat-soluble nutrients. Therefore, there is still a need for the development of alternative and/or improved therapeutic strategies for the treatment obesity and/or its related discorders.

SUMMARY OF THE INVENTION

Accordingly, it is an object of the present invention to provide alternative, improved and/or integrated means or methods that address one or more problems, including those described above such as in the treatment (including prophylactic treatment) of one or more conditions, disorders or diseases selected from obesity and its related discorders, and/or agents and pharmaceutical compositions useful for such treatment. Such an object underlying the present invention is solved by the subject-matter as disclosed or defined anywhere herein, for example by the subject-matter of the attached claims.

The present invention is based on the surprising finding of the inventors that the administration of both (i) an agonist of transient receptor potential M8 (TRPM8-agonist) and (ii) an agonist of the nicotinic acetylcholine receptor (nAChR-agonist) results in a significant weight loss which is synergistic compared to controls (i.e., an administration of only one or none of those two agonists). In particular, it was shown that in certain embodiments, the combination administration can improve different aspects of the glucose metabolism (e.g., food intake, glucose control, and thermogenesis). Moreover, in certain embodiments, it is possible that significant weight loss is not accompanied with unsdesirable side effects, such as nausea, steatorrhea, and/or fecal incontinence.

Thus, in a first aspect, the present invention provides a composition comprising an agonist of TRPM8 (TRPM8-agonist) and an agonist of the nicotinic acetylcholine receptor (nAChR-agonist).

In a further aspect, the present invention provides a composition, in particular a pharmaceutical composition, comprising a TRPM8-agonist and an nAChR-agonist for use in medicine, in particular, for treating or preventing a disease selected from the group consisting of obesity and obesity-related disorders or conditions (such as diabetes (e.g., type 2 diabetes), hyperlipidemia (such as hypercholesterolemia and/or hypertriglyceridemia), renal disease (such as diabetic nephropathy), gallbladder disease (such as gall stones), eye disease (such as diabetic retinopathy), osteoarthritis, hypertension, advanced glycoxidation and/or lipoxidation end-product formation, stroke, metabolic syndrome, arteriosclerosis, coronary heart disease, gout, sleep apnea (such as obstructive sleep apnea), non-alcoholic fatty liver disease (NAFLD), and/or non-alcoholic steatohepatitis (NASH)).

In a further aspect, the present invention provides a composition, in particular a pharmaceutical composition, comprising a TRPM8-agonist and an nAChR-agonist for inhibiting weight gain, e.g., weight gain following smoking cessation or for reducing weight.

In a further aspect, the present invention provides a composition, in particular a pharmaceutical composition, wherein an agonist of TRPM8 (TRPM8-agonist) and an agonist of the nicotinic acetylcholine receptor (nAChR-agonist) are connected by a linker.

In a further aspect, the present invention provides a method of treating or preventing a disease in a subject in need thereof, comprising administering to the subject a TRPM8-agonist and an nAChR-agonist, wherein the disease is preferably selected from the group consisting of obesity and obesity-related disorders (such as diabetes (e.g., type 2 diabetes), hyperlipidemia (such as hypercholesterolemia and/or hypertriglyceridemia), renal disease (such as diabetic nephropathy), gallbladder disease (such as gall stones), eye disease (such as diabetic retinopathy), osteoarthritis, hypertension, advanced glycoxidation and/or lipoxidation end-product formation, stroke, metabolic syndrome, arteriosclerosis, coronary heart disease, gout, sleep apnea (such as obstructive sleep apnea), non-alcoholic fatty liver disease (NAFLD), and/or non-alcoholic steatohepatitis (NASH)).

In a further aspect, the present invention provides a method of inhibiting weight gain (e.g., weight gain following smoking cessation or for reducing weight) in a subject in need thereof, comprising administering to the subject a TRPM8-agonist and an nAChR-agonist.

Other features and advantages of the present invention will be apparent from the following detailed description and claims.

The patent or application file contains at least one drawing executed in color. Copies of this patent or patent application publication with color drawing(s) will be provided by the Office upon request and payment of the necessary fee.

Without being bound to any theory, it is believed that by acting on nicotinic acetylcholine receptors in the brain nAChR-agonists decrease the food intake, whereas the thermogenesis in brown fat tissues is increased by TRMP8-agonists.

Figure 2:
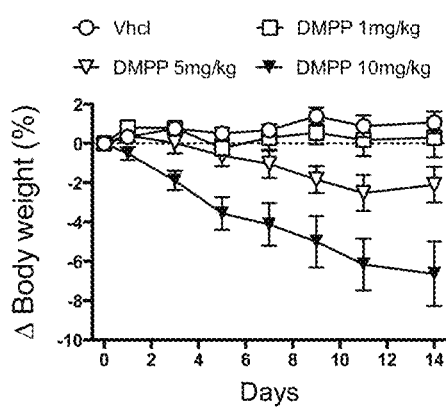
Figure 2:
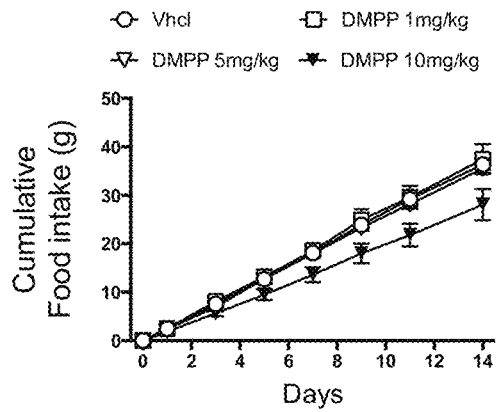
Figure 2:
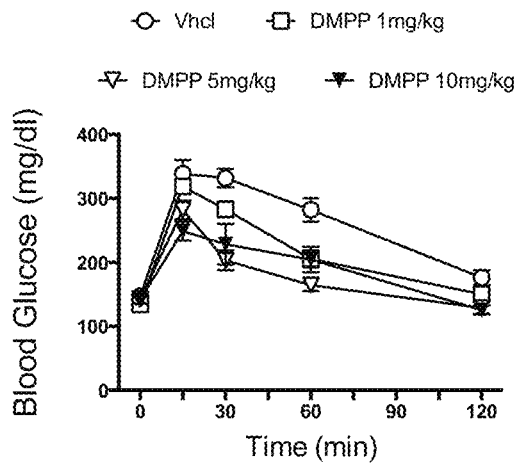
Figure 2:
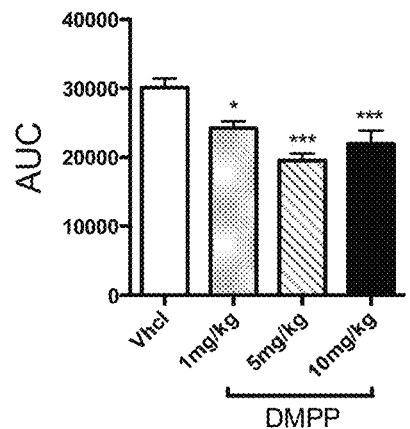

FIG. 2: Effects of a monotherapy (using an nAChR-agonist alone) on obese mice

Effect on (A) body weight and (B) food intake: DIO male mice were treated 14 days with vehicle (control; white circle) or the nAChR-agonist DMPP (1 mg/kg (white square), 5 mg/kg (white triangle) or 10 mg/ml (black triangle)). Compounds were administered by daily subcutaneous injections. Effect on (C) glucose tolerance and (D) area under the curve (AUC): Glucose tolerance was assessed following 7-days treatment of DIO male mice with vehicle (white circle) or DMPP (1 mg/kg (white square), 5 mg/kg (white triangle) or 10 mg/ml (black triangle)). Compounds were administered by daily subcutaneous injections. Data represent means±SEM; n=8. *P<0.05, P<0.01, *P<0.001.

Figure 3:
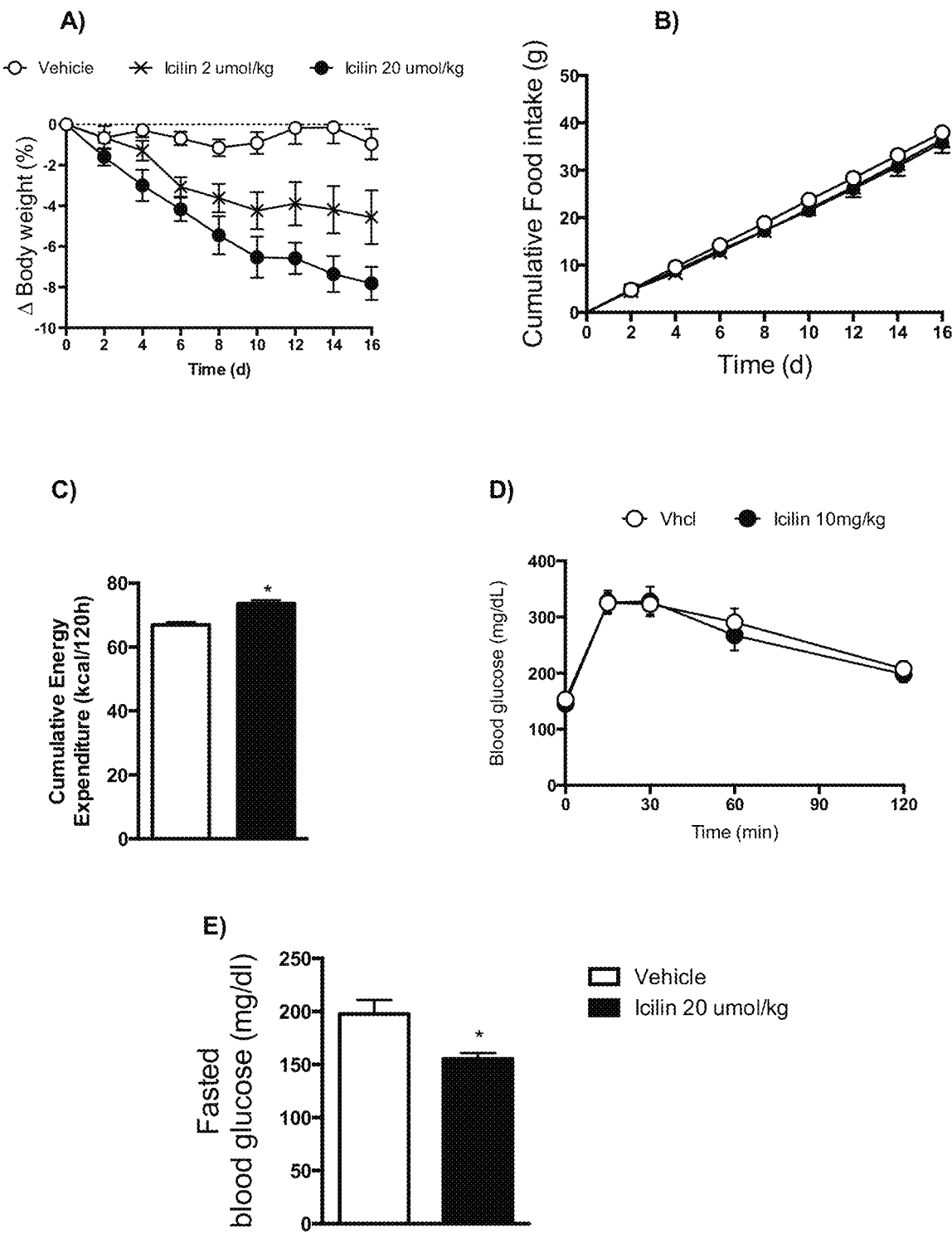

FIG. 3: Effects of a monotherapy (using a TRPM8-agonist alone) on obese mice

Effect on (A) body weight and (B) food intake: DIO male mice were treated 16 days with vehicle (white circle) or the TRPM8-agonist icilin (0.6 mg/kg (star) or 6 mg/kg (black circle)). Effect on (C) energy expenditure: DIO male mice were treated 5 days with vehicle (white bar) or icilin (6 mg/kg (black bar)). Compounds were administered by daily subcutaneous injections. Effect on (D) glucose tolerance: Glucose tolerance was assessed following 7-days treatment of DIO male mice with vehicle (white) or icilin (6 mg/kg) (black). Effect on (E) fasting glucose: Fasting glucose was assessed following 23-days treatment of DIO male mice with vehicle (white bar) or icilin (6 mg/kg) (black bar). Compounds were administered by daily subcutaneous injections. Data represent means±SEM; n=8. *P<0.05.

Figure 4:
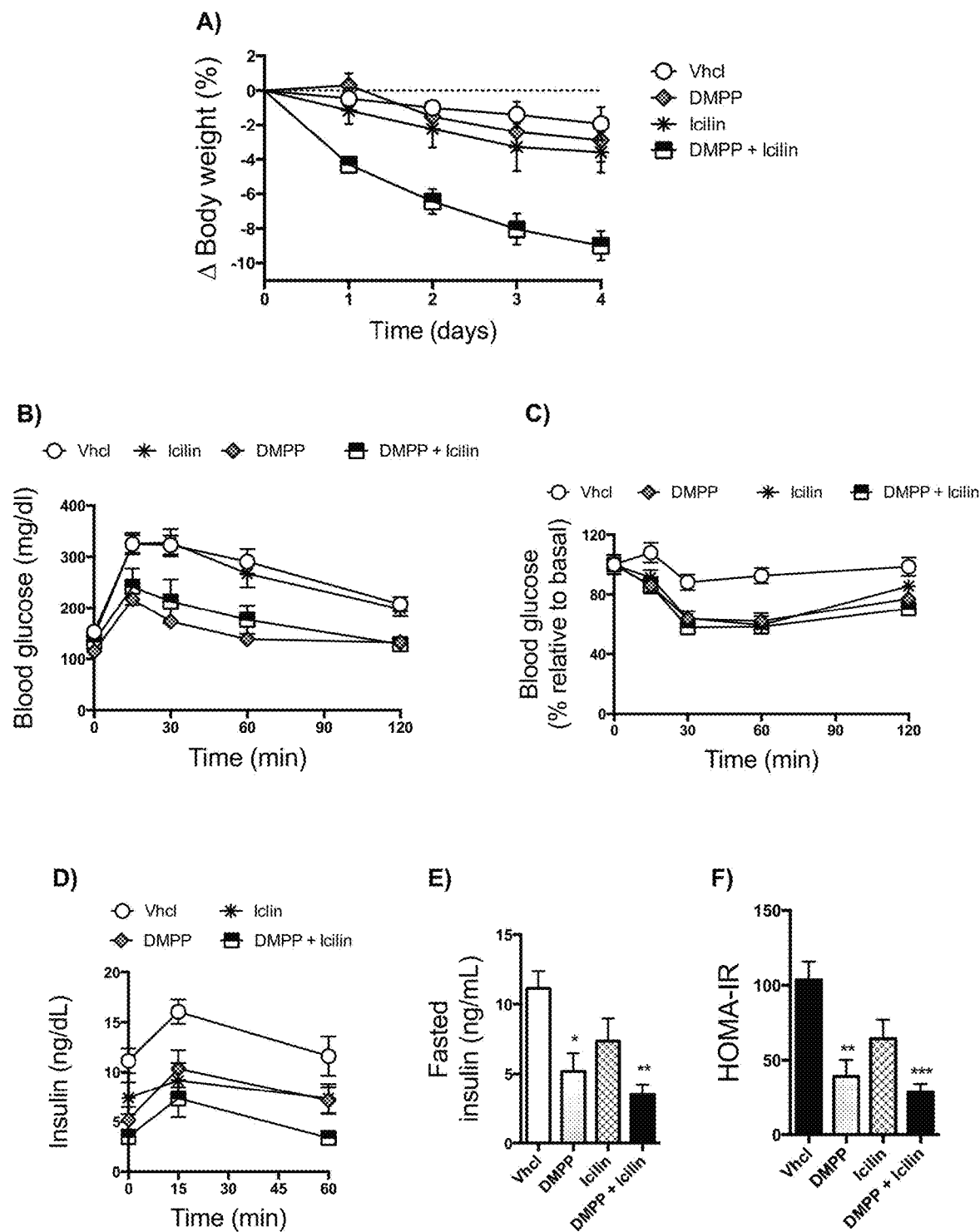

FIG. 4: Effects of a combination therapy (using an nAChR-agonist and a TRPM8-agonist) on obese mice Effect on (A) body weight: DIO male mice were treated 4 days with vehicle (white circle), the nAChR-agonist DMPP alone (10 mg/kg) (grey diamond), the TRPM8-agonist icilin alone (5 mg/kg) (black star), or DMPP (10 mg/ml)+icilin (5 mg/kg) (checkered square). Compounds were administered by daily subcutaneous injections. Effect on (B) glucose tolerance, (C) glucose-stimulated insulin secretion, (D) insulin sensitivity, (E) fasting insulin and (F) HOMA-IR score: Glucose tolerance was assessed following 7-days treatment of DIO male mice with vehicle (white circle), DMPP alone (10 mg/kg) (grey diamond), icilin alone (5 mg/kg) (black star), or DMPP (10 mg/kg)+icilin (5 mg/kg) (checkered square). Compounds were administered by daily subcutaneous injections. Data represent means±SEM; n=8. *P<0.05, P<0.01, *P<0.001.

Figure 5:
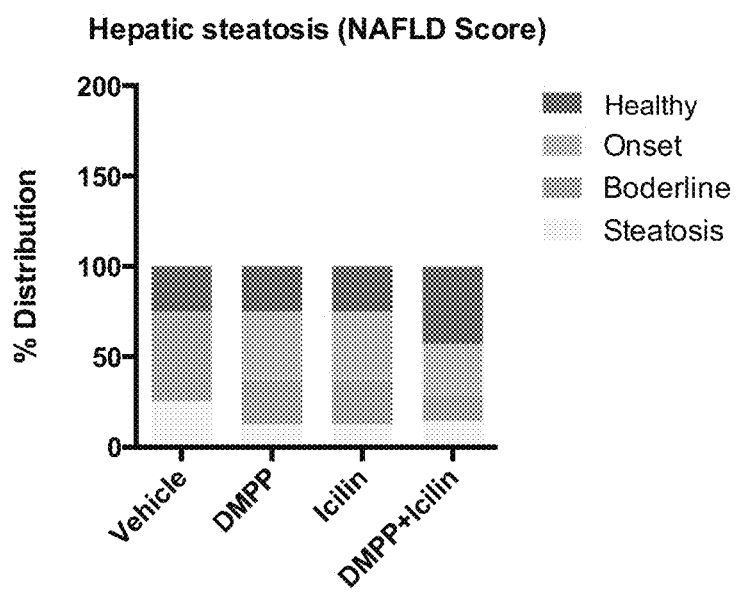
Figure 5:
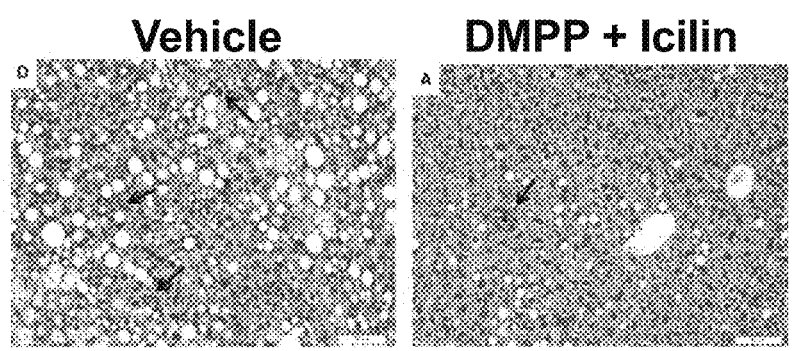

FIG. 5: Effects of a combination therapy (using an nAChR-agonist and a TRPM8-agonist) on hepatic lipid accumulation Hepatic lipid accumulation following 2-weeks treatment of DIO male mice with vehicle, DMPP (10 mg/kg), icilin (5 mg/kg) or DMPP (10 mg/ml)+icilin (5 mg/kg). Compounds were administered by daily subcutaneous injections. Effect on (A) non-alcoholic fatty liver disease activity score (NAFLD Score) and (B) histological H&E staining of livers from representative mice treated with either vehicle or DMPP (10 mg/kg)+icilin (5 mg/kg).

Figure 6:
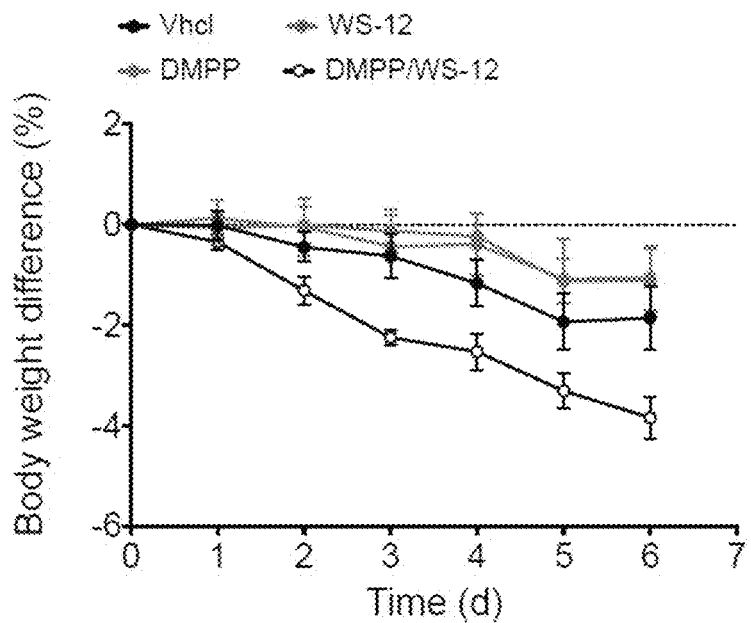
Figure 6:
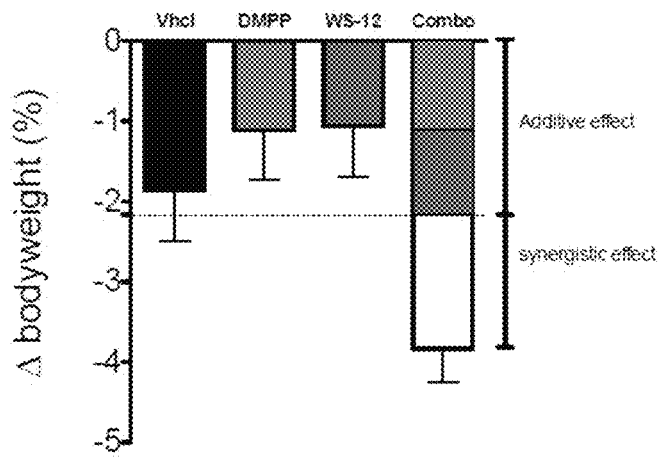

FIG. 6: Effects of a combination therapy (using an nAChR-agonist and a TRPM8-agonist) on obese mice.

Effect on (A) body weight in diet-induced obese (DIO) male mice treated daily for 6 consecutive days with either vehicle (black circle), the nAChR-agonist DMPP alone (5 mg/kg) (light blue circle), the TRMP8-agonist N-(4-methoxyphenyl)-5-methyl-2-(1-methylethyl)cyclohexanecarboxamide (also designated as WS-12) alone (20 nmol/kg; 5 mg/kg) (red circle), or the combination of DMPP (5 mg/kg) and N-(4-methoxyphenyl)-5-methyl-2-(1-methylethyl)cyclohexanecarboxamide (5 mg/kg) (white circle). Compounds were administered by daily via subcutaneous injections in a volume of 5 µl per gram body weight. Effect on (B) body weight showing the synergistic effect for the combination of DMPP and N-(4-methoxyphenyl)-5-methyl-2-(1-methylethyl)cyclohexanecarboxamide at the end of the study (day 6). N=7-8 mice each group. Data represent means±SEM.

DETAILED DESCRIPTION OF THE PRESENT INVENTION

Although the present invention is further described in more detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims and other disclosures herein. Unless defined otherwise, all technical and scientific terms used herein have the same meanings as commonly understood by one of ordinary skill in the art.

In the following, the elements of the present invention will be described in more detail. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in one embodiment the nAChR-agonist is a DMPP salt and in another embodiment the TRMP8-agonist is icilin, then in a preferred embodiment, the composition according to the present invention comprises a DMPP salt as nAChR-agonist and icilin as TRMP8-agonist.

Preferably, the terms used herein are defined as described in "*A multilingual glossary of biotechnological terms: (IU-*

*PAC Recommendations*)", H. G. W. Leuenberger, B. Nagel, and H. Kolbl, Eds., Helvetica Chimica Acta, CH-4010 Basel, Switzerland, (1995).

The practice of the present invention will employ, unless otherwise indicated, conventional methods of chemistry, biochemistry, and recombinant DNA techniques which are explained in the literature in the field (cf., e.g., *"Molecular Cloning: A Laboratory Manual"*, $2^{nd}$ Edition, J. Sambrook et al. eds., Cold Spring Harbor Laboratory Press, Cold Spring Harbor 1989).

Throughout this specification and the claims which follow, unless the context requires otherwise, the term "comprise", and variations such as "comprises" and "comprising", will be understood to imply the inclusion of a stated member, integer or step or group of members, integers or steps but not the exclusion of any other member, integer or step or group of members, integers or steps. The term "consisting essentially of" means excluding other members, integers or steps of any essential significance. For example, a pharmaceutical composition consisting essentially of the members/components as defined herein (such as a TRMP8-agonist, an nAChR-agonist and optionally one additional active compound) would exclude further active compounds (besides the TRMP8-agonist, the nAChR-agonist derivative and the optional one additional active compound) but would not exclude contaminants (e.g., those from the isolation and purification method(s) used to produce the TRMP8-agonist, the nAChR-agonist and/or the optional one additional active compound) in trace amounts (e.g., the amount of the contaminant (preferably the amount of all contaminants present in the composition) is less than 5% by weight, such as less than 4% by weight, 3% by weight, 2% by weight, 1% by weight, 0.5% by weight, 0.1% by weight, with respect to the total composition) and/or pharmaceutically acceptable excipients (such as carriers, e.g., phosphate buffered saline, preservatives, and the like). The term "consisting of" means excluding all other members, integers or steps of significance. For example, a pharmaceutical composition consisting of the members/components as defined herein (such as a TRMP8-agonist, an nAChR-agonist, one excipient, and optionally one additional active compound) would exclude any other compound (including a second or further excipient) in an amount of more than 2% by weight (such as any other compound in an amount of more than 1% by weight, more than 0.5% by weight, more than 0.4% by weight, more than 0.3% by weight, more than 0.2% by weight, more than 0.1% by weight, more than 0.09% by weight, more than 0.08% by weight, more than 0.07% by weight, more than 0.06% by weight, more than 0.05% by weight, more than 0.04% by weight, more than 0.03% by weight, more than 0.02% by weight, more than 0.01% by weight) with respect to the total composition. The term "comprising" encompasses the term "consisting essentially of" which, in turn, encompasses the term "consisting of". Thus, at each occurrence in the present application, the term "comprising" may be replaced with the term "consisting essentially of" or "consisting of". Likewise, at each occurrence in the present application, the term "consisting essentially of" may be replaced with the term "consisting of".

The terms "a" and "an" and "the" and similar reference used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by the context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "alkyl" refers to a monoradical of a saturated straight or branched hydrocarbon. Preferably, the alkyl group comprises from 1 to 20 carbon atoms, such as from 1 to 12 or from 1 to 10 carbon atoms, i.e., 1, 2, 3, 4, 5, 6, 7, 8, 9, or 10 carbon atoms, more preferably 1 to 8 carbon atoms, such as 1 to 6 or 1 to 4 carbon atoms. Exemplary alkyl groups include methyl, ethyl, propyl, iso-propyl, butyl (e.g., n-butyl, iso-butyl, tert-butyl), pentyl (e.g., n-pentyl, iso-pentyl, sec-pentyl, neo-pentyl), 1,2-dimethyl-propyl, iso-amyl, n-hexyl, iso-hexyl, sec-hexyl, 2,2-dimethylbutyl, n-heptyl, iso-heptyl, n-octyl, 2-ethyl-hexyl, n-nonyl, n-decyl, and the like. A "substituted alkyl" means that one or more (such as 1 to the maximum number of hydrogen atoms bound to an alkyl group, e.g., 1, 2, 3, 4, 5, 6, 7, 8, 9, or up to 10, such as between 1 to 5, 1 to 4, or 1 to 3, or 1 or 2) hydrogen atoms of the alkyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl. Examples of a substituted alkyl include trifluoromethyl, 2,2,2-trichloroethyl, arylalkyl (also called "aralkyl", e.g., benzyl, chloro(phenyl)methyl, 4-methylphenylmethyl, (2,4-dimethylphenyl)methyl, o-fluorophenylmethyl, 2-phenylpropyl, 2-, 3-, or 4-carboxyphenylalkyl), or heteroarylalkyl (also called "heteroaralkyl").

The term "alkenyl" refers to a monoradical of an unsaturated straight or branched hydrocarbon having at least one carbon-carbon double bond. Generally, the maximum number of carbon-carbon double bonds in the alkenyl group can be equal to the integer which is calculated by dividing the number of carbon atoms in the alkenyl group by 2 and, if the number of carbon atoms in the alkenyl group is uneven, rounding the result of the division down to the next integer. For example, for an alkenyl group having 9 carbon atoms, the maximum number of carbon-carbon double bonds is 4. Preferably, the alkenyl group has 1 to 4, i.e., 1, 2, 3, or 4, carbon-carbon double bonds. Preferably, the alkenyl group comprises from 2 to 20 carbon atoms, such as from 2 to 12 or from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkenyl group comprises from 2 to 10 carbon atoms and 1, 2, 3, 4, or 5 carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenyl groups include ethenyl (i.e., vinyl), 1-propenyl, 2-propenyl (i.e., allyl), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, and the like. If an alkenyl group is attached to a nitrogen atom, the double bond cannot be alpha to the nitrogen atom. A "substituted alkenyl" means that one or more (such as 1 to the maximum number of hydrogen atoms bound to an alkenyl group, e.g., 1, 2, 3, 4, 5, 6, 7, 8, 9, or up to 10, such as between 1 to 5, 1 to 4, or 1 to 3, or 1 or 2) hydrogen atoms of the alkenyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl. An example of a substituted alkenyl is styryl (i.e., 2-phenylvinyl).

The term "alkynyl" refers to a monoradical of an unsaturated straight or branched hydrocarbon having at least one carbon-carbon triple bond. Generally, the maximum number of carbon-carbon triple bonds in the alkynyl group can be equal to the integer which is calculated by dividing the number of carbon atoms in the alkynyl group by 2 and, if the number of carbon atoms in the alkynyl group is uneven, rounding the result of the division down to the next integer. For example, for an alkynyl group having 9 carbon atoms, the maximum number of carbon-carbon triple bonds is 4. Preferably, the alkynyl group has 1 to 4, i.e., 1, 2, 3, or 4, more preferably 1 or 2 carbon-carbon triple bonds. Preferably, the alkynyl group comprises from 2 to 20 carbon atoms, such as from 2 to 12 or from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkynyl group comprises from 2 to 10 carbon atoms and 1, 2, 3, 4, or 5 (preferably 1, 2, or 3) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. Exemplary alkynyl groups include ethynyl, 1-propynyl (i.e., —C≡CCH$_3$), 2-propynyl (i.e., —CH$_2$C≡CH or propargyl), 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, and the like. If an alkynyl group is attached to a nitrogen atom, the triple bond cannot be alpha to the nitrogen atom. A "substituted alkynyl" means that one or more (such as 1 to the maximum number of hydrogen atoms bound to an alkynyl group, e.g., 1, 2, 3, 4, 5, 6, 7, 8, 9, or up to 10, such as between 1 to 5, 1 to 4, or 1 to 3, or 1 or 2) hydrogen atoms of the alkynyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl.

The term "aryl" or "aromatic ring" refers to a monoradical of an aromatic cyclic hydrocarbon. Preferably, the aryl group contains 3 to 14 (e.g., 5 to 10, such as 5, 6, or 10) carbon atoms which can be arranged in one ring (e.g., phenyl) or two or more condensed rings (e.g., naphthyl). Exemplary aryl groups include cyclopropenylium, cyclopentadienyl, phenyl, indenyl, naphthyl, azulenyl, fluorenyl, anthryl, and phenanthryl. Preferably, "aryl" refers to a monocyclic ring containing 6 carbon atoms or an aromatic bicyclic ring system containing 10 carbon atoms. Preferred examples are phenyl and naphthyl. A "substituted aryl" means that one or more (such as 1 to the maximum number of hydrogen atoms bound to an aryl group, e.g., 1, 2, 3, 4, 5, 6, 7, 8, 9, or up to 10, such as between 1 to 5, 1 to 4, or 1 to 3, or 1 or 2) hydrogen atoms of the aryl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), =X (e.g., =O, =S, or =NH), alkyl (e.g., C$_{1-6}$ alkyl), alkenyl (e.g., C$_{2-6}$ alkenyl), and alkynyl (e.g., C$_{2-6}$ alkynyl). Examples of a substituted aryl include biphenyl, 2-fluorophenyl, anilinyl, 3-nitrophenyl, 4-hydroxyphenyl, methoxyphenyl (i.e., 2-, 3-, or 4-methoxyphenyl), and 4-ethoxyphenyl.

The term "areno" refers to an aromatic cyclic hydrocarbon which is fused to (or condensed with) another cyclic moiety. Preferably, the areno group contains 5 to 14 (i.e., 5, 6, 7, 8, 9, 10, 11, 12, 13, or 14 such as 5, 6, or 10) carbon atoms which can be arranged in one ring (e.g., benzo) or two or more condensed rings (e.g., naphtho). Exemplary areno groups include cyclopentadieno, benzo, indeno, naphtho, azuleno, fluoreno, anthra, and phenanthro. Preferably, "areno" refers to a monocyclic ring containing 6 carbon atoms or an aromatic bicyclic ring system containing 10 carbon atoms. Preferred examples are benzo and naphtho.

The term "heteroaryl" or "heteroaromatic ring" means an aryl group as defined above in which one or more carbon atoms in the aryl group are replaced by heteroatoms of O, S, or N. Preferably, heteroaryl refers to a five or six-membered aromatic monocyclic ring wherein 1, 2, or 3 carbon atoms are replaced by the same or different heteroatoms of O, N, or S. Alternatively, it means an aromatic bicyclic or tricyclic ring system wherein 1, 2, 3, 4, or 5 carbon atoms are replaced with the same or different heteroatoms of O, N, or S. Preferably, in each ring of the heteroaryl group the maximum number of O atoms is 1, the maximum number of S atoms is 1, and the maximum total number of O and S atoms is 2. Exemplary heteroaryl groups include furanyl, thienyl, oxazolyl, isoxazolyl, oxadiazolyl, pyrrolyl, imidazolyl, pyrazolyl, triazolyl, tetrazolyl, thiazolyl, isothiazolyl, thiadiazolyl, pyridyl, pyrimidinyl, pyrazinyl, triazinyl, benzofuranyl, indolyl, isoindolyl, benzothienyl, 1H-indazolyl, benzimidazolyl, benzoxazolyl, indoxazinyl, benzisoxazolyl, benzothiazolyl, benzisothiazolyl, benzotriazolyl, quinolinyl, isoquinolinyl, benzodiazinyl, quinoxalinyl, quinazolinyl, benzotriazinyl, pyridazinyl, phenoxazinyl, thiazolopyridinyl, pyrrolothiazolyl, phenothiazinyl, isobenzofuranyl, chromenyl, xanthenyl, pyrrolizinyl, indolizinyl, indazolyl, purinyl, quinolizinyl, phthalazinyl, naphthyridinyl, cinnolinyl, pteridinyl, carbazolyl, phenanthridinyl, acridinyl, perimidinyl, phenanthrolinyl, and phenazinyl. Exemplary 5- or 6-membered heteroaryl groups include furanyl, thienyl, oxazolyl, isoxazolyl, oxadiazolyl, pyrrolyl, imidazolyl (e.g., 2-imidazolyl), pyrazolyl, triazolyl, tetrazolyl, thiazolyl, isothiazolyl, thiadiazolyl, pyridyl (e.g., 4-pyridyl), pyrimidinyl, pyrazinyl, triazinyl, and pyridazinyl. A "substituted heteroaryl" means that one or more (such as 1 to the maximum number of hydrogen atoms bound to a heteroaryl group, e.g., 1, 2, 3, 4, 5, 6, 7, 8, 9, or up to 10, such as between 1 to 5, 1 to 4, or 1 to 3, or 1 or 2) hydrogen atoms of the heteroaryl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), =X (e.g., =O, =S, or =NH), alkyl (e.g., C$_{1-6}$ alkyl), alkenyl (e.g., C$_{2-6}$ alkenyl), and alkynyl (e.g., C$_{2-6}$ alkynyl). Examples of a substituted heteroaryl include 3-phenylpyrrolyl, 2,3'-bifuryl, 4-methylpyridyl, 2-, or 3-ethylindolyl.

The term "heteroareno" refers to an areno group as defined above in which one or more carbon atoms in the areno group are replaced by heteroatoms (such as O, S, or N). Preferably, heteroareno refers to a five or six-membered aromatic monocyclic ring wherein 1, 2, or 3 carbon atoms are replaced by the same or different heteroatoms (such as O, N, or S). Alternatively, it means an aromatic bicyclic or tricyclic ring system wherein 1, 2, 3, 4, or 5 carbon atoms are replaced with the same or different heteroatoms (such as O, N, or S). Preferably, in each ring of the heteroareno group the maximum number of O atoms is 1, the maximum number of S atoms is 1, and the maximum total number of O and S atoms is 2. Exemplary heteroareno groups include furano (also called furo), thieno, oxazolo, isoxazolo, oxadiazolo (1,2,5- and 1,2,3-), pyrrolo, imidazolo (also called imidazo), pyrazolo, triazolo (1,2,3- and 1,2,4-), tetrazolo, thiazolo, isothiazolo, thiadiazolo (1,2,3- and 1,2,5-), pyridino (also called pyrido), pyrimidino (also called pyrimido), pyrazino, triazino (1,2,3-, 1,2,4-, and 1,3,5-), indolo, isoindolo, 1H-indazolo, indoxazino, quinolino (also called quino), isoquinolino (also called isochino), quinoxalino, quinazolino, pyridazino, phenoxazino, phenothiazino, chromeno, xantheno, phenoxathiinyl, pyrrolizino, indolizino, indazolo, purino, quinolizino, phthalazino, naphthyridino (1,5-, 1,6-, 1,7-, 1,8-, and 2,6-), cinnolino, pteridino, carbazolo, phenanthridino, acridino, perimidino, phenanthrolino (1,7-, 1,8-, 1,10-, 3,8-, and 4,7-), phenazino, and combinations of any of the foregoing such as benzothieno (1- and 2-), benzofurano (1- and 2-), benzimidazolo, benzoxazolo, benzisoxazolo, benzothiazolo, benzisothiazolo, benzotriazolo, benzodiazino, benzotriazino (1,2,3- and 1,2,4-benzotriazino), thiazolopyridino, pyrrolothiazolo, isobenzofurano, oxazolopyridino, isoxazolopyridino, pyrrolooxazolo, and pyrrolopyrrolo. In one embodiment, the heteroareno is 5- or 6-membered (preferably monocyclic) and examples thereof include furano, thieno, oxazolo, isoxazolo, oxadiazolo (1,2,5- and 1,2,3-), pyrrolo, imidazolo, pyrazolo, triazolo (1,2,3- and 1,2,4-), thiazolo, isothiazolo, thiadiazolo (1,2,3- and 1,2,5-), pyridino, pyrimidino, pyrazino, triazino (1,2,3-, 1,2,4-, and 1,3,5-), and pyridazino. In one embodiment, the heteroareno is selected from the group consisting of pyridino, pyrimidino, pyrrolo, pyrazine, pyrazolo, imidazo, furano, and oxazolo.

The term "cycloalkyl" or "cycloaliphatic" represents cyclic non-aromatic versions of "alkyl" and "alkenyl" with preferably 3 to 14 carbon atoms, such as 3 to 10 carbon atoms, i.e., 3, 4, 5, 6, 7, 8, 9, or 10 carbon atoms, more preferably 3 to 7 carbon atoms. In one embodiment, the cycloalkyl group has 1, 2, or more (preferably 1 or 2) double bonds. Exemplary cycloalkyl groups include cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl, cyclooctenyl, cyclononyl, cyclononenyl, cylcodecyl, cylcodecenyl, and adamantyl. The term "cycloalkyl" is also meant to include bicyclic and tricyclic versions thereof. If bicyclic rings are formed it is preferred that the respective rings are connected to each other at two adjacent carbon atoms, however, alternatively the two rings are connected via the same carbon atom, i.e., they form a spiro ring system or they form "bridged" ring systems. Preferred examples of cycloalkyl include C$_3$-C$_8$-cycloalkyl, in particular cyclopropyl, cyclobutyl, cyclopentyl, cyclopentenyl, cyclohexyl, cyclohexenyl, cyclohexadienyl, cycloheptyl, cyclooctyl, spiro[3,3]heptyl, spiro[3,4] octyl, spiro[4,3]octyl, spiro[4,5]decanyl, bicyclo[4.1.0] heptyl, bicyclo[3.2.0]heptyl, bicyclo[2.2.1]heptyl (i.e., norbornyl), bicyclo[2.2.2]octyl, bicyclo[5.1.0]octyl, bicyclo [4.2.0]octyl, bicyclo[4.3.0]nonyl, 1,2,3,4-tetrahydronaphthyl (i.e., tetralinyl), and bicyclo[4.4.0]decanyl (i.e., decalinyl). A "substituted cycloalkyl" means that one or more (such as 1 to the maximum number of hydrogen atoms bound to a cycloalkyl group, e.g., 1, 2, 3, 4, 5, 6, 7, 8, 9, or up to 10, such as between 1 to 5, 1 to 4, or 1 to 3, or 1 or 2) hydrogen atoms of the cycloalkyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), =X (e.g., =O, =S, or =NH), alkyl (e.g., C$_{1-6}$ alkyl), alkenyl (e.g., C$_{2-6}$ alkenyl), and alkynyl (e.g., C$_{2-6}$ alkynyl). Examples of a substituted cycloalkyl include oxocyclohexyl, oxocyclopentyl, fluorocyclohexyl, and oxocyclohexenyl.

The term "heterocyclyl" or "heterocyclic ring" means a cycloalkyl group as defined above in which from 1, 2, 3, or 4 carbon atoms in the cycloalkyl group are replaced by heteroatoms of oxygen, nitrogen, silicon, selenium, phosphorous, or sulfur, preferably O, S, or N. A heterocyclyl group has preferably 1 or 2 rings containing from 3 to 10, such as 3, 4, 5, 6, or 7, ring atoms. Preferably, in each ring of the heterocyclyl group the maximum number of O atoms is 1, the maximum number of S atoms is 1, and the maximum total number of O and S atoms is 2. The term "heterocyclyl" is also meant to encompass partially or completely hydrogenated forms (such as dihydro, tetrahydro or perhydro forms) of the above-mentioned heteroaryl groups. Exemplary heterocyclyl groups include morpholinyl, pyrrolidinyl, imidazolidinyl, pyrazolidinyl, piperidinyl (also called piperidyl), piperazinyl, di- and tetrahydrofuranyl, di- and tetrahydrothienyl, di- and tetrahydropyranyl, urotropinyl, lactones, lactams, cyclic imides, and cyclic anhydrides. A "substituted heterocyclyl" means that one or more (such as 1 to the maximum number of hydrogen atoms bound to a heterocyclyl group, e.g., 1, 2, 3, 4, 5, 6, 7, 8, 9, or up to 10, such as between 1 to 5, 1 to 4, or 1 to 3, or 1 or 2) hydrogen atoms of the heterocyclyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —OR$^{11}$ (e.g., —OH), —SR$^{11}$ (e.g., —SH), —N(R$^2$)(R$^{13}$) (e.g., —NH$_2$), =X (e.g., =O, =S, or =NH), alkyl (e.g., C$_{1-6}$ alkyl), alkenyl (e.g., C$_{2-6}$ alkenyl), and alkynyl (e.g., C$_{2-6}$ alkynyl).

The term "aromatic" as used in the context of hydrocarbons means that the whole molecule has to be aromatic. For example, if a monocyclic aryl is hydrogenated (either partially or completely) the resulting hydrogenated cyclic structure is classified as cycloalkyl for the purposes of the present invention. Likewise, if a bi- or polycyclic aryl (such as naphthyl) is hydrogenated the resulting hydrogenated bi- or polycyclic structure (such as 1,2-dihydronaphthyl) is classified as cycloalkyl for the purposes of the present invention (even if one ring, such as in 1,2-dihydronaphthyl, is still aromatic). A similar distinction is made within the present application between heteroaryl and heterocyclyl. For example, indolinyl, i.e., a dihydro variant of indolyl, is classified as heterocyclyl for the purposes of the present invention, since only one ring of the bicyclic structure is aromatic and one of the ring atoms is a heteroatom.

The term "5- to 8-membered ring" means a cycloaliphatic, aromatic, heterocyclic or heteroaromatic ring as defined above which is condensed with another ring (e.g., with the phenyl group of formula (VI), (VI'), (VI$_1$), (VI$_1$'), (VI$_2$), or (VI$_2$')) and which has 5, 6, 7, or 8, preferably 6 ring atoms. In one embodiment, the 5- to 8-membered ring is cycloaliphatic. In another embodiment, the 5- to 8-membered ring is aromatic. The 5- to 8-membered ring may be substituted, i.e., so that one or more (such as 1 to the maximum number of hydrogen atoms bound to the 5- to 8-membered ring, e.g., 1, 2, 3, 4, 5, or 6, such as between 1 to 5, 1 to 4, or 1 to 3, or 1 or 2) hydrogen atoms of the 5- to 8-membered ring are replaced with a substituent other than hydrogen (when more than one hydrogen atom is replaced the substituents may be the same or different). Preferably, the substituent other than hydrogen is a 1$^{st}$ level substituent, a 2$^{nd}$ level substituent, or a 3$^{rd}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), =X (e.g., =O, =S, or =NH), alkyl (e.g., C$_{1-6}$ alkyl), alkenyl (e.g., C$_{2-6}$ alkenyl), and alkynyl (e.g., C$_{2-6}$ alkynyl).

The term "halogen" or "halo" means fluoro, chloro, bromo, or iodo. The term "hydroxy" means OH. The term "nitro" means NO$_2$. The term "cyano" means the group —CN. The term "isocyano" means the group —NC. The term "cyanato" means the group —OCN. The term "isocyanato" means the group —NCO. The term "thiocyanato" means the group —SCN. The term "isothiocyanato" means the group —NCS. The term "azido" means N$_3$.

The term "amino" includes unsubstituted amino (i.e., the group —NH$_2$) and substituted amino (i.e., mono- or disubstituted amino, wherein one or two of the hydrogen atoms have been replaced with a group other than hydrogen). Thus, the term "amino" means the group —N(R$^{12}$)(R$^{13}$), wherein R$^{12}$ and R$^{13}$ are, in each case, independently selected from the group consisting of —H, alkyl, alkenyl, alkynyl, cycloalkyl, aryl, heteroaryl, and heterocyclyl, or R$^{12}$ and R$^{13}$ may join together with the nitrogen atom to which they are attached to form the group —N=CR$^{15}$R$^{16}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected R$^{30}$; R$^{15}$ and R$^{16}$ are independently selected from the group consisting of —H, alkyl, alkenyl, alkynyl, cycloalkyl, aryl, heteroaryl, heterocyclyl, and —NH$_y$R$^{20}_{2-y}$, or R$^{15}$ and R$^{16}$ may join together with the atom to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected R$^{30}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected R$^{30}$; y is an integer from 0 to 2; R$^{20}$ is selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected R$^{30}$; and R$^{30}$ is a 1$^{st}$ (or 2$^{nd}$ or 3$^{rd}$) level substituent.

The term "imino" means the group —N(R$^{14}$)—, wherein both free valences of the nitrogen atom may bind to one other atom (e.g., C) resulting in a double bond (e.g., C=N(R$^{14}$)) or to different atoms (e.g., two C atoms) resulting two single bonds (e.g., C—N(R$^{14}$)—C). In each case, R$^{14}$ is selected from the group consisting of —H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected R$^{30}$; and R$^{30}$ is a 1$^{st}$ (or 2$^{nd}$ or 3$^{rd}$) level substituent.

The term "optionally substituted" indicates that one or more (such as 1 to the maximum number of hydrogen atoms bound to a moiety, e.g., 1, 2, 3, 4, 5, 6, 7, 8, 9, or up to 10, such as between 1 to 5, 1 to 4, or 1 to 3, or 1 or 2) hydrogen atom(s) may be replaced with a group/substituent (i.e., a 1$^{st}$ level substituent) different from hydrogen such as alkyl (preferably, C$_{1-6}$ alkyl), alkenyl (preferably, C$_{2-6}$ alkenyl), alkynyl (preferably, C$_{2-6}$ alkynyl), aryl (preferably, 3- to 14-membered aryl), heteroaryl (preferably, 3- to 14-membered heteroaryl), cycloalkyl (preferably, 3- to 14-membered cycloalkyl), heterocyclyl (preferably, 3- to 14-membered heterocyclyl), halogen, —CN, —NC, —NCO, —CNO, —SCN, —NCS, —N$_3$, —NO$_2$, —OR$^{71}$, —N(R$^{72}$)(R$^{73}$), —ON(R$^{72}$)(R$^{73}$), —N$^+$(—O$^-$)(R$^{72}$)(R$^{73}$), —S(O)$_{0-2}$R$^{71}$ (i.e., —SR$^{71}$, —S(O)R$^{71}$, or —S(O)$_2$R$^{71}$), —S(O)$_{0-2}$OR$^{71}$ (e.g., —S(O)$_{1-2}$OR$^{71}$), —OS(O)$_{0-2}$OR$^{71}$ (e.g., —OS(O)$_{1-2}$OR$^{71}$), —S(O)$_{0-2}$N(R$^{72}$)(R$^{73}$) (e.g., —S(O)$_{1-2}$N(R$^{72}$)(R$^{73}$)), —OS(O)$_{0-2}$N(R$^{72}$)(R$^{73}$) (e.g., —OS(O)$_{1-2}$N(R$^{72}$)(R$^{73}$)), —N(R$^{71}$)S(O)$_{0-2}$R$^{71}$ (e.g., —N(R$^{71}$)S(O)$_{1-2}$R$^{71}$), —NR$^{71}$S(O)$_{0-2}$OR$^{71}$ (e.g., —NR$^{71}$S(O)$_{1-2}$OR$^{71}$), —NR$^{71}$S(O)$_{0-2}$N(R$^{72}$)(R$^{73}$) (e.g., —NR$^{71}$S(O)$_{1-2}$N(R$^{72}$)(R$^{73}$)), —C(=X$^1$)R$^{71}$, —C(=X$^1$)X$^1$R$^{71}$, —X$^1$C(=X$^1$)R$^{71}$, and —X$^1$C(=X$^1$)X$^1$R$^{71}$, and/or any two 1$^{st}$ level substituents which are bound to the same carbon atom of a cycloalkyl or heterocyclyl group may join together to form =X$^1$, wherein each of the alkyl, alkenyl, alkynyl, aryl, heteroaryl, cycloalkyl, and heterocyclyl groups of the 1$^{st}$ level substituent may themselves be substituted by one or more (e.g., one, two or three) substituents (i.e., $2^{nd}$ level substituents) selected from the group consisting of $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl, halogen, —$CF_3$, —CN, —NC, —NCO, —CNO, —SCN, —NCS, —$N_3$, —$NO_2$, —$OR^{81}$, —$N(R^{82})(R^{83})$, —$ON(R^{82})(R^{83})$, —$N^+(\text{—}O^-)(R^{82})(R^{83})$, —$S(O)_{0-2}R^{81}$ (i.e., —$SR^{81}$, —$S(O)R^{81}$, or —$S(O)_2R^{81}$), —$S(O)_{0-2}OR^{81}$ (e.g., —$S(O)_{1-2}OR^{81}$), —$OS(O)_{0-2}R^{81}$ (e.g., —$OS(O)_{1-2}R^{81}$), —$OS(O)_{0-2}OR^{81}$ (e.g., —$OS(O)_{1-2}OR^{81}$), —$S(O)_{0-2}N(R^{82})(R^{83})$ (e.g., —$S(O)_{1-2}N(R^{82})(R^{83})$), —$OS(O)_{0-2}N(R^{82})(R^{83})$ (e.g., —$OS(O)_{1-2}N(R^{82})(R^{83})$), —$N(R^{81})S(O)_{0-2}R^{81}$ (e.g., —$N(R^{81})S(O)_{1-2}R^{81}$), —$NR^{81}S(O)_{0-2}OR^{81}$ (e.g., —$NR^{81}S(O)_2OR^{81}$), —$NR^{81}S(O)_{0-2}N(R^{82})(R^{83})$ (e.g., —$NR^{81}S(O)_{1-2}N(R^{82})(R^{83})$), —$C(=X^2)R^{81}$, —$C(=X^2)X^2R^{81}$, —$X^2C(=X^2)R^{81}$, and —$X^2C(=X^2)X^2R^{81}$, and/or any two $2^{nd}$ level substituents which are bound to the same carbon atom of a cycloalkyl or heterocyclyl group may join together to form $=X^2$, wherein each of the $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl groups of the $2^{nd}$ level substituent is optionally substituted with one or more (e.g., one, two or three) substituents (i.e., $3^{rd}$ level substituents) independently selected from the group consisting of $C_{1-3}$ alkyl, halogen, —$CF_3$, —CN, —NC, —NCO, —CNO, —SCN, —NCS, —$N_3$, —$NO_2$, —OH, —$O(C_{1-3}$ alkyl), —$OCF_3$, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)(C_{1-3}$ alkyl), —$C(=O)OH$, —$C(=O)O(C_{1-3}$ alkyl), —$C(=O)NH_{2-z}(C_{1-3}$ alkyl)$_z$, —$OC(=O)(C_{1-3}$ alkyl), —$OC(=O)O(C_{1-3}$ alkyl), —$OC(=O)NH_{2-z}(C_{1-3}$ alkyl)$_z$, —$NHC(=O)(C_{1-3}$ alkyl), —$NHC(=O)NH_{2-2}(C_{1-3}$ alkyl)$_z$, —$NHC(=NH)NH_{2-z}(C_{1-3}$ alkyl)$_z$, and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl, and/or any two $3^{rd}$ level substituents which are bound to the same carbon atom of a cycloalkyl or heterocyclyl group may join together to form =O, =S, =NH, or =N($C_{1-3}$ alkyl);
wherein
$R^{71}$, $R^{72}$, and $R^{73}$ are independently selected from the group consisting of —H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents selected from the group consisting of $C_{1-3}$ alkyl, halogen, —$CF_3$, —CN, —NC, —NCO, —CNO, —SCN, —NCS, —$N_3$, —$NO_2$, —OH, —$O(C_{1-3}$ alkyl), —$OCF_3$, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)z, —$C(=O)(C_{1-3}$ alkyl), —$C(=O)OH$, —$C(=O)O(C_{1-3}$ alkyl), —$C(=O)NH_{2-z}(C_{1-3}$ alkyl)$_z$, —$OC(=O)(C_{1-3}$ alkyl), —$OC(=O)O(C_{1-3}$ alkyl), —$OC(=O)NH_{2-z}(C_{1-3}$ alkyl)$_z$, —$NHC(=O)(C_{1-3}$ alkyl), —$NHC(=O)NH_{2-2}(C_{1-3}$ alkyl)$_z$, —$NHC(=NH)NH_{2-z}(C_{1-3}$ alkyl)$_z$, and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl,
or $R^{72}$ and $R^{73}$ may join together with the nitrogen atom to which they are attached to form a 5- or 6-membered ring, which is optionally substituted with one, two or three substituents selected from the group consisting of $C_{1-3}$ alkyl, halogen, —$CF_3$, —CN, —NC, —NCO, —CNO, —SCN, —NCS, —$N_3$, —$NO_2$, —OH, —$O(C_{1-3}$ alkyl), —$OCF_3$, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)(C_{1-3}$ alkyl), —$C(=O)OH$, —$C(=O)O(C_{1-3}$ alkyl), —$C(=O)NH_{2-z}(C_{1-3}$ alkyl)$_z$, —$OC(=O)(C_{1-3}$ alkyl), —$OC(=O)O(C_{1-3}$ alkyl), —$OC(=O)NH_{2-z}(C_{1-3}$ alkyl)$_z$, —$NHC(=O)(C_{1-3}$ alkyl), —$NHC(=O)NH_{z-2}(C_{1-3}$ alkyl)$_z$, —$NHC(=NH)NH_{2-z}(C_{1-3}$ alkyl)$_z$, and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl;
$R^{81}$, $R^{82}$, and $R^{83}$ are independently selected from the group consisting of —H, $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl, wherein each of the $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents selected from the group consisting of $C_{1-3}$ alkyl, halogen, —$CF_3$, —CN, —NC, —NCO, —CNO, —SCN, —NCS, —$N_3$, —$NO_2$, —OH, —$O(C_{1-3}$ alkyl), —$OCF_3$, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)(C_{1-3}$ alkyl), —$C(=O)OH$, —$C(=O)O(C_{1-3}$ alkyl), —$C(=O)NH_{2-z}(C_{1-3}$ alkyl)$_z$, —$OC(=O)(C_{1-3}$ alkyl), —$OC(=O)O(C_{1-3}$ alkyl), —$OC(=O)NH_{2-z}(C_{1-3}$ alkyl)$_z$, —$NHC(=O)(C_{1-3}$ alkyl), —$NHC(=O)NH_{z-2}(C_{1-3}$ alkyl)$_z$, —$NHC(=NH)NH_{2-z}(C_{1-3}$ alkyl)$_z$, and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl,
or $R^{82}$ and $R^{83}$ may join together with the nitrogen atom to which they are attached to form a 5- or 6-membered ring, which is optionally substituted with one, two or three substituents selected from the group consisting of $C_{1-3}$ alkyl, halogen, —$CF_3$, —CN, —NC, —NCO, —CNO, —SCN, —NCS, —$N_3$, —$NO_2$, —OH, —$O(C_{1-3}$ alkyl), —$OCF_3$, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)(C_{1-3}$ alkyl), —$C(=O)OH$, —$C(=O)O(C_{1-3}$ alkyl), —$C(=O)NH_{2-z}(C_{1-3}$ alkyl)$_z$, —$OC(=O)(C_{1-3}$ alkyl), —$OC(=O)O(C_{1-3}$ alkyl), —$OC(=O)NH_{2-z}(C_{1-3}$ alkyl)$_z$, —$NHC(=O)(C_{1-3}$ alkyl), —$NHC(=O)NH_{z-2}(C_{1-3}$ alkyl)$_z$, —$NHC(=NH)NH_{2-z}(C_{1-3}$ alkyl)$_z$, and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl;
$X^1$ and $X^2$ are independently selected from O, S, and $N(R^{84})$, wherein $R^{84}$ is —H or $C_{1-3}$ alkyl.

Typical $1^{st}$ level substituents are preferably selected from the group consisting of $C_{1-6}$ alkyl, $C_{2-6}$ alkenyl, $C_{2-6}$ alkynyl, 3- to 14-membered (such as 5- or 6-membered) aryl, 3- to 14-membered (such as 5- or 6-membered) heteroaryl, 3- to 14-membered (such as 3- to 7-membered) cycloalkyl, 3- to 14-membered (such as 3- to 7-membered) heterocyclyl, halogen, —CN, —NC, —NCO, —CNO, —SCN, —NCS, —$N_3$, —$NO_2$, —$OR^{71}$, —$N(R^{72})(R^{73})$, —$S(O)_{0-2}R^{71}$, —$S(O)_{0-2}OR^{71}$, —$OS(O)_{0-2}R^{71}$, —$OS(O)_{0-2}OR^{71}$, —$S(O)_{0-2}N(R^{72})(R^{73})$, —$OS(O)_{0-2}N(R^{72})(R^{73})$, —$N(R^{71})S(O)_{0-2}R^7$, —$NR^{71}S(O)_2OR^{71}$, —$C(=X^1)R^{71}$, —$C(=X^1)X^1R^{71}$, —$X^1C(=X)R^{71}$, and —$X^1C(=X^1)X^1R^{71}$, such as $C_{1-4}$ alkyl, $C_{2-4}$ alkenyl, $C_{2-4}$ alkynyl, 5- or 6-membered aryl, 5- or 6-membered heteroaryl, 3- to 7-membered cycloalkyl, 3- to 7-membered heterocyclyl, halogen, —$CF_3$, —CN, —NC, —NCO, —CNO, —SCN, —NCS, —$N_3$, —$NO_2$, —OH, —$O(C_{1-3}$ alkyl), —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)OH$, —$C(=O)O(C_{1-3}$ alkyl), —$C(=O)NH_{2-z}(C_{1-3}$ alkyl)$_z$, —$NHC(=O)(C_{1-3}$ alkyl), —$NHC(=NH)NH_{z-2}(C_{1-3}$ alkyl)$_z$, and —$N(C_{1-3}$ alkyl)$C (=NH)NH$_{2-z}$(C$_{1-3}$ alkyl)$_z$, wherein z is 0, 1, or 2 and C$_{1-3}$ alkyl is methyl, ethyl, propyl or isopropyl; X$^1$ is independently selected from O, S, NH and N(CH$_3$); and R$^{71}$, R$^{72}$, and R$^{73}$ are as defined above or, preferably, are independently selected from the group consisting of —H, C$_{1-4}$ alkyl, C$_{2-4}$ alkenyl, C$_{2-4}$ alkynyl, 5- or 6-membered cycloalkyl, 5- or 6-membered aryl, 5- or 6-membered heteroaryl, and 5- or 6-membered heterocyclyl, wherein each of the alkyl, alkenyl, alkynyl, cycloalkyl, aryl, heteroaryl, and heterocyclyl groups is optionally substituted with one, two or three substituents selected from the group consisting of C$_{1-3}$ alkyl, halogen, —CF$_3$, —CN, —NC, —NCO, —CNO, —SCN, —NCS, —N$_3$, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl; or R$^{72}$ and R$^{73}$ may join together with the nitrogen atom to which they are attached to form a 5- or 6-membered ring, which is optionally substituted with one, two or three substituents selected from the group consisting of C$_{1-3}$ alkyl, halogen, —CF$_3$, —CN, —NC, —NCO, —CNO, —SCN, —NCS, —N$_3$, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl.

Typical 2$^{nd}$ level substituents are preferably selected from the group consisting of C$_{1-4}$ alkyl, C$_{2-4}$ alkenyl, C$_{2-4}$ alkynyl, 5- or 6-membered aryl, 5- or 6-membered heteroaryl, 5- or 6-membered cycloalkyl, 5- or 6-membered heterocyclyl, halogen, —CF$_3$, —CN, —NC, —NCO, —CNO, —SCN, —NCS, —N$_3$, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl. Particularly preferred 2$^{nd}$ level substituents include 4-morpholinyl, homomorpholinyl, 4-piperidinyl, homopiperidinyl (i.e., azepanyl, in particular 4-azepanyl), 4-piperazinyl, homopiperazinyl (i.e., diazepanyl, in particular 2,4-diazepanyl), N-methyl-piperazin-4-yl, N-methyl-homopiperazinyl, —CH$_2$CH$_2$OCH$_3$, —OCH$_2$CH$_2$OCH$_3$, —CH$_2$CH$_2$NH$_{2-z}$(CH$_3$)$_z$, —OCH$_2$CH$_2$NH$_{2-z}$(CH$_3$)$_z$, —CF$_3$, and —OCF$_3$.

Typical 3$^{rd}$ level substituents are preferably selected from the group consisting of phenyl, furanyl, pyrrolyl, thienyl, imidazolyl, oxazolyl, isoxazolyl, thiazolyl, pyridyl, pyrazinyl, pyrimidinyl, pyridazinyl, partially and completely hydrogenated forms of the forgoing groups, morpholino, C$_{1-3}$ alkyl, halogen, —NC, —NCO, —CNO, —SCN, —NCS, —N$_3$, —CF$_3$, —OH, —OCH$_3$, —OCF$_3$, —SCH$_3$, —NH$_{2-z}$(CH$_3$)$_z$, —C(=O)OH, and —C(=O)OCH$_3$, wherein z is 0, 1, or 2.

The term "optional" or "optionally" as used herein means that the subsequently described event, circumstance or condition may or may not occur, and that the description includes instances where said event, circumstance, or condition occurs and instances in which it does not occur.

"Isomers" are compounds having the same molecular formula but differ in structure ("structural isomers") or in the geometrical positioning of the functional groups and/or atoms ("stereoisomers"). "Enantiomers" are a pair of stereoisomers which are non-superimposable mirror-images of each other. A "racemic mixture" or "racemate" contains a pair of enantiomers in equal amounts and is denoted by the prefix (+). "Diastereomers" are stereoisomers which are not enantiomers. "Tautomers" are structural isomers of the same chemical substance that spontaneously interconvert with each other, even when pure.

In isotopically labeled compounds one or more atoms are replaced by a corresponding atom having the same number of protons but differing in the number of neutrons. For example, a hydrogen atom may be replaced by a deuterium atom. Exemplary isotopes which can be used in the compounds described herein (in particular, the TRMP8- and nAChR-agonists described herein) include deuterium, $^{11}$C, $^{13}$C, $^{14}$C, $^{15}$N, $^{18}$F, $^{32}$S, $^{36}$Cl, and $^{125}$I. The term "isotopically enriched" means that the occurrence of the isotope is beyond the natural abundance.

The term "half-life" relates to the period of time which is needed to eliminate half of the activity, amount, or number of molecules. In the context of the present invention, the half-life of a TRMP8- or nAChR-agonist is indicative for the stability of said agonist.

In case a structural formula shown in the present application can be interpreted to encompass more than one isomer, said structural formula, unless explicitly stated otherwise, encompasses all possible isomers, and hence each individual such isomer. For example, an nAChR-agonist of the formula:

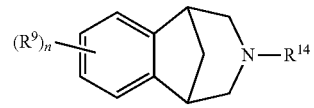

encompasses both isomers, i.e., the isomer having the following formula (a) and the isomer having the following formula (b):

(a)

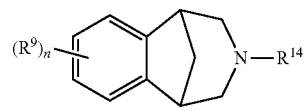

(Ib)

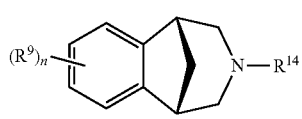

"Polymorphism" as referred to herein means that a solid material (such as a compound) is able to exist in more than one form or crystalline structure, i.e., "polymorphic modifications" or "polymorphic forms". The terms "polymorphic modifications", "polymorphic forms", and "polymorphs" are used interchangeable in the present invention. According to the present invention, these "polymorphic modifications" include crystalline forms, amorphous forms, solvates, and hydrates. Mainly, the reason for the existence of different polymorphic forms lies in the use of different conditions during the crystallization process, such as the following:

solvent effects (the packing of crystal may be different in polar and nonpolar solvents);

certain impurities inhibiting growth pattern and favor the growth of a metastable polymorphs;

the level of supersaturation from which material is crystallized (in which generally the higher the concentration above the solubility, the more likelihood of metastable formation);

temperature at which crystallization is carried out;

geometry of covalent bonds (differences leading to conformational polymorphism);

change in stirring conditions.

Polymorphic forms may have different chemical, physical, and/or pharmacological properties, including but not limited to, melting point, X-ray crystal and diffraction pattern, chemical reactivity, solubility, dissolution rate, vapor pressure, density, hygroscopicity, flowability, stability, compactability, and bioavailability. Polymorphic forms may spontaneously convert from a metastable form (unstable form) to the stable form at a particular temperature. According to Ostwald's rule, in general it is not the most stable but the least stable polymorph that crystallizes first. Thus, quality, efficacy, safety, processability and/or manufacture of a chemical compound, such as a compound of the present invention, can be affected by polymorphism. Often, the most stable polymorph of a compound (such as a TRMP8- or nAChR-agonist) is chosen due to the minimal potential for conversion to another polymorph. However, a polymorphic form which is not the most stable polymorphic form may be chosen due to reasons other than stability, e.g. solubility, dissolution rate, and/or bioavailability.

The term "crystalline form" of a material as used herein means that the smallest components (i.e., atoms, molecule or ions) of said material form crystal structures. A "crystal structure" as referred to herein means a unique three-dimensional arrangement of atoms or molecules in a crystalline liquid or solid and is characterized by a pattern, a set of atoms arranged in a particular manner, and a lattice exhibiting long-range order and symmetry. A lattice is an array of points repeating periodically in three dimensions and patterns are located upon the points of a lattice. The subunit of the lattice is the unit cell. The lattice parameters are the lengths of the edges of a unit cell and the angles between them. The symmetry properties of the crystal are embodied in its space group. In order to describe a crystal structure the following parameters are required: chemical formula, lattice parameters, space group, the coordinates of the atoms and occupation number of the point positions.

The term "amorphous form" of a material as used herein means that the smallest components (i.e., atoms, molecule or ions) of said material are not arranged in a lattice but are arranged randomly. Thus, unlike crystals in which a short-range order (constant distances to the next neighbor atoms) and a long-range order (periodical repetition of a basic lattice) exist, only a short-range order exists in an amorphous form.

The term "complex of a compound" as used herein refers to a compound of higher order which is generated by association of the compound with other one or more other molecules. Exemplary complexes of a compound include, but are not limited to, solvates, clusters, and chelates of said compound.

The term "solvate" as used herein refers to an addition complex of a dissolved material in a solvent (such as an organic solvent (e.g., an aliphatic alcohol (such as methanol, ethanol, n-propanol, isopropanol), acetone, acetonitrile, ether, and the like), water or a mixture of two or more of these liquids), wherein the addition complex exists in the form of a crystal or mixed crystal. The amount of solvent contained in the addition complex may be stoichiometric or non-stoichiometric. A "hydrate" is a solvate wherein the solvent is water.

The term "naturally occurring", as used herein in context with an object, refers to the fact that an object can be found in nature. For example, a protein, receptor or ligand that is present in an organism, that can be isolated from a source in nature and that has not been intentionally modified by man in the laboratory is naturally occurring.

By "treat" is meant to administer a compound or composition or a combination of compounds or compositions (e.g., pharmaceutical compositions) to a subject in order to eliminate a condition, disorder or disease; arrest or slow a condition, disorder or disease in a subject; decrease the frequency or severity of symptoms and/or recurrences in a subject who currently has or who previously has had a condition, disorder or disease; and/or prolong, i.e. increase the lifespan of the subject. In particular, the term "treating a condition, disorder or disease" includes curing, shortening the duration, ameliorating, slowing down or inhibiting progression or worsening, of a condition, disorder or disease or the symptoms of said condition, disorder or disease.

"Inhibiting weight gain" means that the weight of a patient is not increased during the period of time investigated. In one embodiment, the term "inhibiting weight gain" also includes the reduction of weight. This reduction may be a reduction by up to or by at least 10%, by up to or by at least 20%, by up to or by at least 30%, by up to or by at least 40%, by up to or by at least 50%, by up to or by at least 60%, by up to or by at least 70%, by up to or by at least 80%, by up to or by at least 90% or by up to 100%.

In one embodiment, the term "treating obesity" preferably means that the weight of a patient is to be reduced, e.g., by up to or by at least 10%, by up to or by at least 20%, by up to or by at least 30%, by up to or by at least 40%, by up to or by at least 50%, by up to or by at least 60%, by up to or by at least 70%, by up to or by at least 80%, by up to or by at least 90% or by up to 100%.

According to the present invention, terms such as "protect", "prevent", "prophylactic", "preventive", or "protective" relate to the prevention of the occurrence and/or the propagation of a condition, disorder or disease in a subject and, in particular, to minimizing the chance that a subject will develop a condition, disorder or disease or to delaying the onset or development of a condition, disorder or disease (e.g., by inhibiting or slowing the development of a new condition, disorder or disease in a subject). For example, a person at risk for being obese (e.g., a person having overweight or a BMI of about 29) would be a candidate for therapy to inhibit weight gain or prevent obesity and/or obesity-related disorders.

By "being at risk" is meant a subject that is identified as having a higher than normal chance of developing a condition, disorder or disease (in particular, obesity or an obesity-related disorder and/or a condition, disorder or disease that gains weight) compared to the general population (in particular, compared to healthy individuals). In addition, a subject who has had, or who currently has, a condition, disorder or disease (in particular, obesity or an obesity-related disorder and/or a condition, disorder or disease that gains weight), is a subject who has an increased risk for developing a condition, disorder or disease, as such a subject may continue to develop a condition, disorder or disease.

The terms "disease", "disorder" and "condition", when used in the context of treatment or therapy (including prophylactic therapy), are used herein interchangeably and refer to any pathological state, in particular those pathological states described herein.

The affinity of a ligand (e.g., a compound such as an agonist) is the ability of the ligand to bind to its binding side (e.g., a site (such as the active side) of a receptor). A measure of the affinity of a ligand to its binding side is its $K_i$ value. In general, high-affinity ligand binding (low $K_i$ value) implies that such binding involves greater intermolecular force between the ligand and its binding side and that a relatively low concentration of the ligand is adequate to maximally occupy the binding side and to maximally achieve a response. In contrast, low-affinity ligand binding (high $K_i$ value) implies that such binding involves less intermolecular force between the ligand and its binding side and that a relatively high concentration of the ligand is required to maximally occupy the binding side and to achieve the maximum response.

The term "agonist" means a compound that binds to a given receptor (e.g., TRPM8 or nAChR) and activates the receptor to produce a biological response. If upon binding to the receptor an agonist produces full efficacy at that receptor, said agonist is designated as full agonist. If upon binding to the receptor an agonist produces only partial efficacy at the receptor relative to a full agonist (such as an endogenuous agonist of the receptor) even at maximal receptor occupancy, then said agonist is designated as partial agonist. If upon binding to the receptor an agonist produces an efficacy at the receptor which is higher than the efficacy produced by a full agonist (in particular, an endogenuous agonist of the receptor), then said agonist is designated as superagonist. Preferably, the agonist is a reversible agonist (i.e., it does not bind permanently to a receptor through the formation of one or more covalent bonds). The potency of an agonist is inversely related to its $EC_{50}$ value.

The term "antagonist" means a compound which blocks the action of the agonist and which does not display efficacy to activate the receptors it binds. An antagonist does not maintain the ability to activate a receptor and, once bound, inhibits the function of agonists. Antagonists may be classified as competitive, non-competitive, and uncompetitive. A competitive antagonist reversibly binds to a given receptor at the same binding site (active site) as an agonist (e.g., the endogenous ligand), but without activating the receptor. Thus, a competitive antagonist affects the amount of agonist necessary to achieve a maximal response but does not affect the magnitude of that maximal response. In contrast, a non-competitive antagonists reduces the magnitude of the maximum response that can be attained by any amount of agonist. An uncompetitive antagonist requires receptor activation by an agonist before the antagonist can bind to a separate allosteric binding site.

The term "efficacy" means the maximum response ($E_{max}$) achievable from a compound. In other words, efficacy can be seen as the relationship between occupancy of a receptor and the ability to initiate a response (in particular, at the molecular, cellular, tissue and/or system level). The response depends on both the binding of the compound (e.g., an agonist) and the receptor to which the compound is bound and which then produces a response. Consequently, the potency of a compound depends on both affinity of the compound to the receptor and efficacy. Below a certain minimum concentration of the compound (e.g., an agonist), the effect caused by the binding of the compound to the receptor is too low to be measured. At and above said minimum concentration the effect becomes measurable and rises with increasing concentration of the compound until, at a certain high concentration, the effect cannot be increased any more, even if the concentration of the compound is further increased. Thus, the effect asymptotes to a maximum $E_{max}$. The $E_{max}$ is the maximum possible effect for the agonist. The concentration of the compound at which the effect is 50% of $E_{max}$ is referred to as the half maximal effective concentration which is designated either as $EC_{50}$ when the effect is an activation or as $IC_{50}$ when the effect is an inactivation (or inhibition). Thus, the $EC_{50}$ value is commonly used as a measure of the potency of an agonist (and refers to the agonist's concentration which induces an activating response halfway between the baseline and maximum after a specified exposure time), whereas the $IC_{50}$ value is commonly used as a measure of the potency of an antagonist (and refers to the antagonist's concentration which induces an inhibiting response halfway between the baseline and maximum after a specified exposure time).

The term "potency" as used herein means a measure of the activity of a compound (e.g., an agonist) expressed in terms of the amount required to produce an effect of given intensity. Thus, a compound of high potency triggers a large response at low concentrations, while a compound of low potency triggers a small response at low concentrations. The potency is proportional to affinity and efficacy. In general, the potency of a compound refers to the concentration of the compound which is required to produce 50% of maximum effect.

TRPM8 (Transient receptor potential cation channel subfamily M member 8 (TRPM8), also designated as the cold and menthol receptor 1 (CMR1)) is a homotetramer ion channel. TRPM8 is composed of N- and C-terminal cycto-plasmatic domains and four identical subunits with a transmembrane domain with six helices (S1 to S6), wherein S1-S4 act as the voltage sensor and allow binding of agonists (e.g., menthol or icilin), whereas S5, S6 and a connecting loop make up the pore, which is a non-selective cation channel consisting of a highly conserved hydrophobic region. Upon activation of TRPM8, $Na^+$ and $Ca^{2+}$ can enter the cell resulting in depolarization and the generation of an action potential and eventually leading to the sensation of cold and cold pain. TRPM8 is expressed in sensory neurons, and it is activated by cold temperatures (preferably 10 to 25° C.) or TRPM8-agonists (sometimes also called "cooling agents", such as menthol, icilin, and WS-12).

Nicotinic acetylcholine receptors (abbreviated as nAChRs) are receptors which signal for muscular contraction upon a chemical stimulus and which are cholinergic, i.e., they form ligand-gated ion channels in the plasma membranes of certain neurons and on the presynaptic and postsynaptic sides of the neuromuscular junction. As ionotropic receptors, nAChRs are directly linked to ion channels and do not use second messengers. nAChR is triggered by the binding of the neurotransmitter acetylcholine (ACh) but can also be opened by nicotine and other substances, preferably nAChR-agonists. nAChRs have a molecular mass of about 290 kDa and are made up of five subunits which are arranged symmetrically around a central pore, wherein each subunit comprises four transmembrane domains with both the N- and C-terminus located extracellularly. nAChRs can be broadly classified into two subtypes: nAChRs of the muscle-type (embryonic form: composed of $\alpha_1$, $\beta_1$, $\gamma$, and $\delta$ subunits in a ratio of 2:1:1:1; adult form: composed of $\alpha_1$, $\beta_1$, $\delta$, and $\epsilon$ subunits in a ratio of 2:1:1:1) and nAChRs of the neuronal-type (various homomeric or heteromeric combinations of subunits $\alpha_2$-$\alpha_{10}$ and $\beta_2$-$\beta_4$, such as $(\alpha_4)_3(\beta_2)_2$, $(\alpha_4)_2(\beta_2)_3$, and $(\alpha_7)_5$). Upon activation of the nAChRs cations move through the ion channel resulting in (i) a depolarization of the plasma membrane and (ii) modulation of different intracellular cascades (by calcium ions) leading, e.g., to the regulation of the activity of some genes or the release of neurotransmitters.

A menthyl group as used herein refers to the moiety

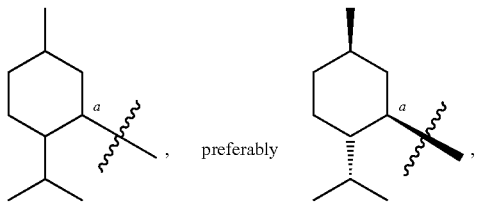

wherein the wiggly line on the right side means that the menthyl group is attached to the rest of the compound through the C atom at position a.

The term "analogue", as used herein, means a member of a group of chemical compounds which have a core structure in common and which exhibit a common effect (e.g., nAChR-agonism) but which differ in respect to their elemental composition. In particular, an analogue is a compound having a core structure identical to that of another compound, but differing from it in respect of one or more atoms, functional groups, or substructures and retaining the common property.

The terms "synergism" and "synergistic" are used interchangeably herein and mean that two (or more) compounds interact in such a way that enhances or increases one or more effects of the compounds. In particular, the enhanced or increased one or more effects are greater than the sum of the effects achieved when the two (or more) compounds were tested separately. For example, if the administration of agonist 1 alone achieves an effect of 20% and the administration of agonist 2 alone achieves an effect of 10%, whereas the administration of both agonists 1 and 2 achieves an effect of more than 35% (preferably at least 40%, such as at least 45%, at least 50%, at least 55%, at least 60%), the combination therapy using agonists 1 and 2 can be considered synergistic. Generally, if the effect achieved by the combination of two (or more) compounds is at least 10% greater (such as at least 15% greater, at least 20% greater, at least 25% greater, at least 30% greater, at least 35% greater, at least 40% greater, at least 45% greater, at least 50% greater, at least 55% greater, at least 60% greater, at least 65% greater, at least 70% greater, at least 75% greater, at least 80% greater, at least 85% greater, at least 90% greater, at least 95% greater, at least 100% greater) than the sum of effects achieved when the two (or more) compounds are tested separately, then the combination can be considered synergistic.

The terms "obesity" and "obese", as used herein, mean a medical condition in which a patient having obesity or being obese has accumulated excess body fat to such an extent that it may detrimentally effect the patient's health, leading to reduced life expectancy and/or increased health problems. For example, obesity can increase the likelihood of various diseases, particularly heart disease, type 2 diabetes, obstructive sleep apnea, and osteoarthritis. According to the WHO, a crude measure for obesity is the body mass index (BMI), a measurement obtained by dividing a patient's weight by the square of the patient's height. If the BMI is greater than 30 kg/m$^2$, the patient is classified "obese", whereas a BMI value within the range 25-30 kg/m$^2$ is classified as "overweight". Thus, a patient having overweight can be considered a patient being at risk to develop obesity and/or an obesity-related disorder. On average, the energy expenditure of obese patients is greater than that of thin counterparts due to the energy required to maintain an increased body mass. A BMI of about 18.5 to 25 is considered normal.

The term "an obesity-related disorder" means any pathological state which is elicited indirectly and/or directly by obesity. Preferably, an obesity-related disorder can be treated or prevented by treating or preventing obesity. Examples of obesity-related disorders include diabetes (e.g., type 2 diabetes), hyperlipidemia (such as hypercholesterolemia and/or hypertriglyceridemia), renal disease (such as diabetic nephropathy), gallbladder disease (such as gall stones), eye disease (such as diabetic retinopathy), osteoarthritis, hypertension, advanced glycoxidation and/or lipoxidation end-product formation, stroke, metabolic syndrome, arteriosclerosis, coronary heart disease, gout, sleep apnea (such as obstructive sleep apnea), non-alcoholic fatty liver disease (NAFLD), and non-alcoholic steatohepatitis (NASH).

Diabetes is a metabolic disease characterized by recurrent or persistent high blood glucose levels. It can be diagnosed by demonstrating any one of the following symptoms: (1) fasting plasma glucose level≥7.0 mmol/l (126 mg/dl); (2) plasma glucose≥11.1 mmol/l (200 mg/dl) two hours after a 75 g oral glucose load (glucose tolerance test); (3) glycated hemoglobin (HbA$_{1C}$)≥48 mmol/mol (≥6.5%); (4) symptoms of high blood sugar and casual plasma glucose≥11.1 mmol/l (200 mg/dl). Patients with fasting glucose levels from 6.1 to 6.9 mmol/l (110 to 125 mg/dl) are considered to have impaired fasting glucose and, thus, can be considered to be at risk of having or developing diabetes. Likewise, patients having plasma glucose at or above 7.8 mmol/l (140 mg/dl), but not over 11.1 mmol/l (200 mg/dl), two hours after a 75 g oral glucose load, are considered to have impaired glucose tolerance and, thus, can be considered to be at risk of having or developing diabetes. Diabetes is preferably type 2 diabetes, i.e., characterized by insulin resistance (i.e., a condition in which the patient's cells fail to respond to the normal actions of the hormone insulin), optionally combined with relatively reduced insulin secretion. In the early stage of type 2 diabetes, the insulin sensitivity is reduced. A primary cause of type 2 diabetes includes obesity, optionally combined with lack of physical activity and/or poor diet.

Hyperlipidemia involves abnormally elevated levels of lipids (in particular cholesterol and/or triglycerides) in the blood (serum) of a patient. For hypercholesterolemia no absolute cutoff between normal and abnormal cholesterol levels exists, and the values must be interpreted in relation to other health conditions and risk factors. For example, for healthy adults, the UK National Health Service recommends upper limits of total cholesterol of 5 mmol/l, and low-density lipoprotein cholesterol (LDL) of 3 mmol/l. For people at high risk of cardiovascular disease, the recommended limit for total cholesterol is 4 mmol/l, and 2 mmol/l for LDL. In the United States, total cholesterol of less than 200 mg/dl is considered desirable, 200 to 239 mg/dl is considered borderline high, and 240 mg/dl or more is considered high. Generally, it is believed that higher levels of total cholesterol increase the risk of cardiovascular disease, particularly coronary heart disease, wherein levels of LDL or non-HDL cholesterol both predict future coronary heart disease. It is useful to determine all lipoprotein subfractions (VLDL, IDL, LDL, and HDL) when assessing hypercholesterolemia.

Renal disease (or renal insufficiency) is a condition in which the kidneys fail to adequately filter waste products from the blood. Preferably, the renal disease is chronic (such as diabetic nephropathy) and can be diagnosed by the determination of urinary albumin, wherein normoalbuminuria is defined by a urinary albumin excretion of <30 mg/24 h (physiological state), microalbuminuria is defined by a urinary albumin excretion in the range of 30-299 mg/24 h, and clinical (overt) albuminuria is defined by an urinary albumin excretion of ≥300 mg/24 h. Thus, a patient having a urinary albumin excretion in the range of 30-299 mg/24 h can be considered being at risk of having or developing renal disease.

Gallbladder diseases are disorders which involve the gallbladder and include gall stones.

Eye diseases are disorders which involve the eye of a patient and include diabetic retinopathy. Diabetic retinopathy is a damage to the retina caused by complications of diabetes which can eventually lead to blindness.

Osteoarthritis is a disorder involving degradation of joints, including articular cartilage and subchondral bone. Symptoms may include joint pain, tenderness, stiffness, locking, and sometimes an effusion. The development of osteoarthritis is often correlated with obesity, optionally with a history of previous joint injury.

Hypertension is a chronic medical condition in which the blood pressure in the arteries is elevated. In adults (age 18 years), hypertension is defined as a systolic and/or a diastolic blood pressure measurement consistently higher than an accepted normal value (e.g., 139 mmHg systolic and/or 89 mmHg diastolic).

Advanced glycoxidation end-products and lipoxidation end-products are considered to play a role in the development and progression of different oxidative-based diseases including diabetes, atherosclerosis, and neurological disorders. For example, it is believed that in diabetes, in cells unable to reduce glucose intake, high blood glucose results in higher intracellular glucose levels which, in turn, result in increased levels of reducing equivalents (such as NADH and FADH) and the production of reactive oxygen species. Thereby multiple pathogenic mechanisms are activated leading, inter alia, to an increased production of advanced glycoxidation end-products. These advanced glycoxidation end-products exhibit some pathological effects, including increased vascular permeability, increased arterial stiffness, inhibition of vascular dilation by interfering with nitric oxide, oxidizing LDL, and enhanced oxidative stress. Reactive oxygen species degrade unsaturated lipids, resulting in the formation of malondialdehyde which is a reactive aldehyde and is considered to be one of the many reactive electrophile species that cause toxic stress in cells and form advanced lipoxidation end-products (i.e., covalent protein adducts). The formation of malondialdehyde can be used as a marker to determine the level of oxidative stress in a patient.

Stroke (also called cerebrovascular accident or insult, or brain attack) is the outcome when poor blood flow to the brain of a patient results in cell death. Stroke can be classified in two types: (1) ischemic (cause: lack of blood flow to the brain) and (2) hemorrhagic (cause: bleeding). The common result is that part of the brain does not function properly. Main risk factors include hypertension, obesity, hypercholesterolemia, and diabetes.

Metabolic syndrome (also called metabolic syndrome X, cardiometabolic syndrome, syndrome X, insulin resistance syndrome, Reaven's syndrome, and CHAOS (in Australia)) is a disorder of energy utilization and storage. It is diagnosed by a co-occurrence of at least three of the following conditions: (i) abdominal (central) obesity (i.e., when excessive abdominal fat around the stomach and abdomen has built up), (ii) hypertension, (iii) elevated fasting plasma glucose, (iv) hypertriglyceridemia (e.g., >150 mg/dl (1.7 mmol/1)), and (v) low high-density cholesterol (HDL) levels (e.g., <40 mg/dl (1.03 mmol/1) in males, <50 mg/dl (1.29 mmol/1) in females). Metabolic syndrome is considered to increase the risk of developing cardiovascular disease and diabetes.

Arteriosclerosis is the thickening, hardening and loss of elasticity of the walls of arteries, thereby gradually restricting the blood flow to the patient's organs and tissues. This process can lead to severe health risks brought on by atherosclerosis, i.e., a specific form of arteriosclerosis caused by the buildup of plaques (including lipids such as cholesterol) in and on the artery walls. As the plaque buildup continues, the supply (with e.g., glucose and oxygen) to the affected regions drastically decreases. Eventually, the complete occlusion of the arteries can occur, leading to a variety of pathological conditions, including heart attack and stroke. Treatment is often in the form of preventative measures of prophylaxis, e.g., using drugs to treat the underlying condition(s), such as drugs for the treatment of hypercholesterolemia and/or drugs for the treatment of hypertension; changing the patient's diet (e.g., eating fewer fatty foods, but more vegetables, fruits, legumes and whole grains; avoiding drinking alcohol; taking in less salt), exercising regularly; and/or inhibiting weight gain, preferably reducing weight. A specific example of arteriosclerosis is coronary heart disease which is caused by the buildup of plaques (including lipids such as cholesterol) in and on the walls of coronary arteries.

Gout is a condition characterized by recurrent attacks of acute inflammatory arthritis, i.e., a red, tender, hot, swollen joint. It frequently occurs together with other disorders including obesity and metabolic syndrome.

Sleep apnea is a disorder characterized by pauses in breathing or instances of shallow or infrequent breathing during sleep. Risk factors include overweight and obesity. One example of sleep apnea is obstructive sleep apnea which is caused by obstruction of the upper airway.

Non-alcoholic fatty liver disease (NAFLD) is a disorder characterized in that fat is deposited in the liver (hepatic steatosis) due to causes other than excessive alcohol use/alcohol abuse. It is reported that NAFLD is related to insulin resistance and the metabolic syndrome. Thus, it is plausible that treatments originally developed for other insulin-resistant states (such as diabetes, in particular type 2 diabetes), e.g., weight loss, may also be useful in treating or preventing NAFLD. Furthermore, NAFLD can also be caused by drugs (e.g., amiodarone, antiviral drugs (nucleoside analogues), corticosteroids, methotrexate, tamoxifen, or tetracycline) or high intake or fructose. Diagnostic signs of NAFLD include increased liver enzymes and steatosis (e.g., determined by making an ultrasound image of the liver). NAFLD may progress to become non-alcoholic steatohepatitis (NASH), a condition in which steatosis (i.e., accumulation of fat) is combined with inflammation and fibrosis (steatohepatitis).

The terms "patient", "subject", "individual", or "animal" relate to multicellular animals, such as vertebrates. For example, vertebrates in the context of the present invention are mammals, birds (e.g., poultry), reptiles, amphibians, bony fishes, and cartilaginous fishes, in particular domesticated animals of any of the foregoing as well as animals (in particular vertebrates) in captivity such as animals (in particular vertebrates) of zoos. Mammals in the context of the present invention include, but are not limited to, humans, non-human primates, domesticated mammals, such as dogs, cats, sheep, cattle, goats, pigs, horses etc., laboratory mammals such as rodents, e.g., mice, rats, rabbits, guinea pigs, etc. as well as mammals in captivity such as mammals of zoos. The term "animal" as used herein also includes humans. Particular non-limiting examples of birds include domesticated poultry, and include birds such as chickens, turkeys, ducks, geese, guinea fowl, pigeons, pheasants etc.; particular non-limiting examples of bony or cartilaginous fish include those suitable for cultivation by aquiculture, and include bony fish such as salmon, trout, perch, carp, cat-fish, etc.

TRPM8-Agonists

One component of the composition of the present invention is an agonist of TRMP8 (TRMP8-agonist). According to the present invention, any TRMP8-agonist may be used, e.g., those described in Bharate and Bharate (Chem. Neurosci. 3 (2012), 248-267), Leffingwell & Associates (www.leffingwell.com/cooler_than_menthol.htm), US 2011/0145970, WO 2012/061698, WO 2008/039522, and WO 2004/026840. Examples of suitable TRMP8-agonists include those selected from the group consisting of a dihydropyrimidine compound, a menthyl compound, and an aliphatic amide.

In one embodiment, the menthyl compound has the general formula (I), preferably the general formula (I'):

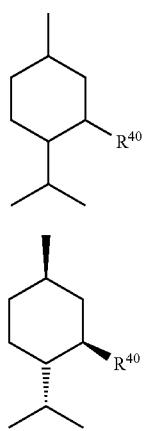

wherein $R^{40}$ is selected from the group consisting of —C(O)NR$^1$R$^2$, —OR$^{11}$, —OC(O)R$^{11}$, —OC(O)OR$^{11}$, and —C(O)OR$^{11}$, wherein R$^1$ and R$^2$ are each independently selected from the group consisting of H, alkyl, cycloalkyl, heterocyclyl aryl, and heteroaryl, wherein each of the alkyl, cycloalkyl, heterocyclyl, aryl, and heteroaryl groups is optionally substituted (e.g., with one or more (in particular 1 to the maximum number of hydrogen atoms bound to the alkyl, cycloalkyl, heterocyclyl, aryl, or heteroaryl group, e.g., 1, 2, 3, 4, 5, 6, 7, 8, 9, or up to 10, such as between 1 to 5, 1 to 4, or 1 to 3, or 1 or 2) independently selected R$^{30}$, wherein R$^{30}$ is a 1$^{st}$ (or 2$^{nd}$ or 3$^{rd}$) level substituent as defined herein); and R$^{11}$ is selected from the group consisting from hydrogen, alkyl, alkenyl, alkynyl, cycloalkyl, heterocyclyl, aryl, and heteroaryl; wherein each of the alkyl, alkenyl, alkynyl, cycloalkyl, heterocyclyl, aryl, and heteroaryl groups is optionally substituted (e.g., with one or more (in particular 1 to the maximum number of hydrogen atoms bound to the alkyl, alkenyl, alkynyl, cycloalkyl, heterocyclyl, aryl, or heteroaryl group, e.g., 1, 2, 3, 4, 5, 6, 7, 8, 9, or up to 10, such as between 1 to 5, 1 to 4, or 1 to 3, or 1 or 2) independently selected R$^{30}$, wherein R$^{30}$ is a 1$^{st}$ (or 2$^{nd}$ or 3$^{rd}$) level substituent as defined herein).

In one preferred embodiment, the menthyl compound has the general formula (Ia), preferably the general formula (Ia'):

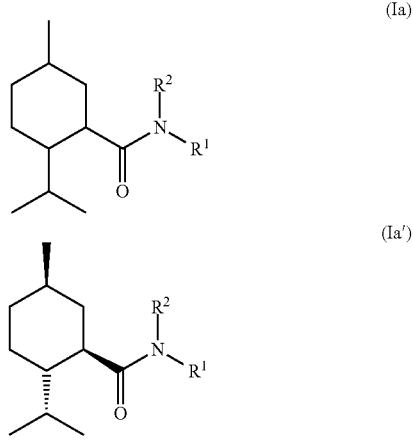

wherein R$^1$ and R$^2$ are each independently selected from the group consisting of H, alkyl, cycloalkyl, aryl, heteroaryl and heterocyclyl, wherein each of the alkyl, cycloalkyl, aryl, heteroaryl, and heterocyclyl groups is optionally substituted (e.g., with one or more (in particular 1 to the maximum number of hydrogen atoms bound to the alkyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected R$^{30}$, wherein R$^{30}$ is a 1$^{st}$ (or 2$^{nd}$ or 3$^{rd}$) level substituent); or R$^1$ and R$^2$ together with the nitrogen atom to which they are attached form a heterocyclic ring which is optionally substituted (e.g., with one or more (in particular 1 to the maximum number of hydrogen atoms bound to the heterocyclic ring, e.g., 1, 2, 3, 4, 5, 6, 7, 8, 9, or up to 10, such as between 1 to 5, 1 to 4, or 1 to 3, or 1 or 2) independently selected R$^{30}$, wherein R$^{30}$ is a 1$^{st}$ (or 2$^{nd}$ or 3$^{rd}$) level substituent). In a preferred embodiment of formula (Ia) (preferably formula (Ia')), the menthyl compound has the general formula (Ia$_1$), preferably the general formula (Ia$_1$'):

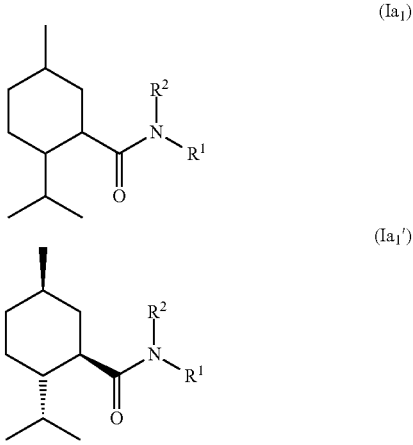

wherein R$^1$ is H or C$_{1-6}$ alkyl (e.g., H or C$_{1-3}$ alkyl, preferably, H or methyl, more preferably H) and R$^2$ is selected from the group consisting of C$_{1-6}$ alkyl (preferably C$_{1-4}$ alkyl), phenyl, 5- or 6-membered heteroaryl containing 1 or 2 ring nitrogen atoms, 3- to 7-membered cycloalkyl, or 5- to 10-membered heterocyclyl, wherein each of the $C_{1-6}$ alkyl (preferably $C_{1-4}$ alkyl), phenyl, 5- or 6-membered heteroaryl containing 1 or 2 ring nitrogen atoms, 3- to 7-membered cycloalkyl, and 5- to 10-membered heterocyclyl groups is optionally substituted with 1, 2, or 3 independently selected $R^{30}$, wherein $R^{30}$ is a $1^{st}$, $2^{nd}$ or $3^{rd}$ level substituent (e.g., $C_{1-3}$ alkyl (optionally substituted with 1 substituent selected from —CN and —NH$_2$), halogen, —OH, —O($C_{1-3}$ alkyl), —CN, —C(O)NH$_2$, —C(O)O($C_{1-3}$ alkyl optionally substituted with 1 —OH), —NHC(O)($C_{1-3}$ alkyl optionally substituted with 1 —NH$_2$), —SO$_2$NH-(5- or 6-membered heteroaryl containing 1 or 2 ring nitrogen atoms), furanyl, 5- or 6-membered heteroaryl containing 1 or 2 ring nitrogen atoms, and phenyl (optionally substituted with 1 substituents selected from —OH and —O($C_{1-3}$ alkyl)); or $R^1$ and $R^2$ together with the nitrogen atom to which they are attached form a 5- to 10-membered heterocyclyl containing 1 or 2 ring nitrogen atoms (such as dihydrobenzimidazolyl), wherein the 5- to 10-membered heterocyclyl is optionally substituted with 1, 2, or 3 independently selected $R^{30}$ (e.g., =O, $C_{1-3}$ alkyl (optionally substituted with 1 NH$_2$), and —O($C_{1-3}$ alkyl optionally substituted with —OH)). Preferred menthyl compounds of formula (Ia), (Ia'), (Ia$_1$) or (Ia$_1$') are those having the general formula (Ia$_2$), preferably the general formula (Ia$_2$') shown in Table 1a.

TABLE 1a (Ia$_2$)

(Ia$_2$')

| $R^1$ | $R^2$ |
|---|---|
| H | ethyl |
| H | tert-butyl |
| H | 2-ethoxyethyl |
| H | —CH$_2$C(O)OCH$_2$CH$_3$ |
| H | —CH(CH$_3$)C(O)OCH$_3$ |
| H | —CH(CH$_3$)C(O)OCH$_2$CH$_3$ |
| H | 2-(2-pyridyl)ethyl |
| H | 2-(2-ethoxyphenyl)ethyl |
| H | 2-hydroxy-2-phenylethyl |
| H | —CH(CH$_3$)C(O)OCH$_3$ |
| H | —CH(CH$_3$)C(O)OCH$_2$CH$_3$ |
| —CH$_3$ | hydroxy(3-hydroxyphenyl)methyl |
| H | —CH(CH$_3$)C(O)O(CH$_2$)$_3$OH |
| H | —CH(CH$_3$)C(O)O(CH(CH$_3$)$_2$OH |
| H | —CH$_2$CH(phenyl)(NHC(O)CH(CH$_3$)NH$_2$) |
| H | 4-methylphenyl |
| H | 3-hydroxy-4-methylphenyl |
| H | 4-methoxyphenyl |
| H | 4-ethoxyphenyl |
| H | 4-fluorophenyl |
| H | 4-cyanophenyl |

TABLE 1a-continued (Ia$_2$)

(Ia$_2$')

| $R^1$ | $R^2$ |
|---|---|
| H | 4-(cyanomethyl)phenyl |
| H | 4-(1H-pyrazol-1-yl)phenyl |
| H | 4-(aminocarbonylmethyl)phenyl |
| H | 4-methoxy-2-((1-aminoethyl)carbonylamino)phenyl |
| H | 4-(2-pyrimidinyl-NHSO$_2$)phenyl |
| H | cyclopropyl |
| H | 1,3-benzodioxol-5-yl |
| H | 2-oxotetrahydrofuran-3-yl |
| H | 1-(2-aminoethyl)-4-(furan-2-yl)-1H-pyrrol-2-yl |

—NR$^1$R$^2$ is

Particularly preferred examples of the menthyl compound of formula (Ia), (Ia'), (Ia$_1$), (Ia$_1$'), (Ia$_2$) or (Ia$_2$') include N-(4-methoxyphenyl)-5-methyl-2-(1-methylethyl)cyclohexanecarboxamide (also designated as WS-12), N-ethyl-5-methyl-2-(1-methylethyl)cyclohexanecarboxamide (also designated as WS-3), ethyl 3-({[5-methyl-2-(propan-2-yl)cyclohexyl]carbonyl}amino)propanoate (also designated as ethyl 3-(p-menthane-3-carboxamido)acetate or WS-5), N-[4-(cyanomethyl)phenyl]-5-methyl-2-(propan-2-yl)cyclohexanecarboxamide (also designated as N-(4-cyanomethylphenyl)-p-menthanecarboxamide or FEMA-4496), and 5-methyl-2-(propan-2-yl)-N-[2-(pyridin-2-yl)ethyl]cyclohexanecarboxamide (also designated as N-(2-(pyridin-2-yl)ethyl)-3-p-menthanecarboxamide or FEMA-4549).

In a further embodiment, the menthyl compound has the general formula (Ib), preferably the general formula (Ib'):

(Ib)

-continued (Ib')

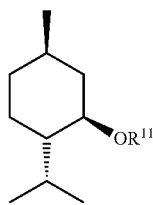

wherein $R^{11}$ is selected from the group consisting from hydrogen alkyl, alkenyl, alkynyl, cycloalkyl, aryl, heteroaryl, and heterocyclyl; wherein each of the alkyl, alkenyl, alkynyl, cycloalkyl, aryl, heteroaryl, and heterocyclyl groups is optionally substituted (e.g., with one or more (in particular 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a $1^{st}$ (or $2^{nd}$ or $3^{rd}$) level substituent). In a preferred embodiment of formula (Ib) (preferably formula (Ib')), the menthyl compound has the general formula (Ib$_1$) or (Ib$_1$'):

(Ib$_1$)

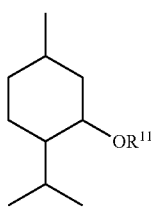

(Ib$_1$')

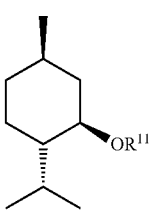

wherein $R^{11}$ is selected from hydrogen and $C_{1-6}$ alkyl (e.g., H or $C_{1-4}$ alkyl) which is optionally substituted with 1 or 2 —OH. Preferred menthyl compounds of formula (Ib), (Ib'), (Ib$_1$) or (Ib$_1$') are those having the formula (Ib$_2$), preferably the general formula (Ib$_2$') shown in Table 1b.

TABLE 1b (Ib$_2$)

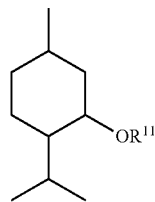

(Ib$_2$')

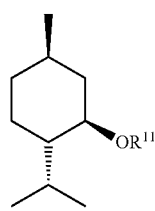

| $R^{11}$ |
| --- |
| H |
| methyl |
| ethyl |
| n-propyl |
| 2-methylpropyl |
| 2,3-dihydroxypropyl |
| 2-hydroxyethyl |
| 2,3-dihydroxy-2-methylpropyl |
| 2-(2-hydroxyethoxy)ethyl |

In a further embodiment, the menthyl compound has the following formula (Ic), preferably the general formula (Ic'):

(Ic)

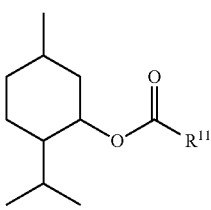

(Ic')

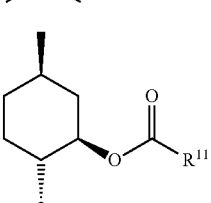

wherein $R^{11}$ is selected from the group consisting from alkyl, alkenyl, alkynyl, cycloalkyl, aryl, heteroaryl, and heterocyclyl; wherein each of the alkyl, alkenyl, alkynyl, cycloalkyl, aryl, heteroaryl, and heterocyclyl groups is optionally substituted (e.g., with one or more (in particular 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a $1^{st}$ (or $2^{nd}$ or $3^{rd}$) level substituent). In a preferred embodiment of formula (Ic) (preferably formula (Ic')), the menthyl compound has the general formula (Ic$_1$) or (Ic$_1$'):

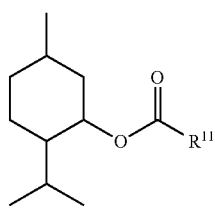
(Ic₁)

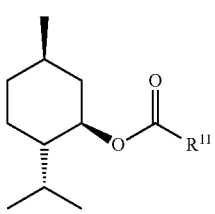
(Ic₁')

wherein $R^{11}$ is selected from $C_{1-6}$ alkyl and 5- or 6-membered heterocyclyl containing 1 or 2 ring nitrogen atoms, wherein each of the $C_{1-6}$ alkyl and 5- or 6-membered heterocyclyl groups is optionally substituted with 1, 2, or 3 independently selected $R^{30}$, wherein $R^{30}$ is a $1^{st}$, $2^{nd}$ or $3^{rd}$ level substituent (e.g., —OH, —COOH, —C(O)NH₂, —C(O)NHCH₃, —C(O)N(CH₃)₂, and —C(O)O(5- or 6-membered cycloalkyl optionally substituted with 1 or 2 $C_{1-3}$ alkyl)). Preferred menthyl compounds of formula (Ic), (Ic'), (Ic₁) or (Ic₁') are those having the general formula (Ic₂), preferably the general formula (Ic₂') shown in Table 1c.

TABLE 1c

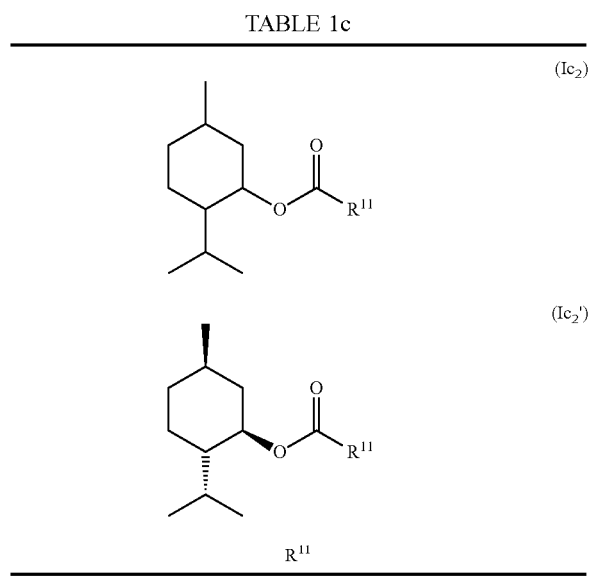

| $R^{11}$ |
|---|
| methyl |
| 1-hydroxyethyl |
| 2-hydroxypropyl |
| 2-carboxyethyl |
| 3-carboxypropyl |
| 3-{[(5-methyl-2-(propan-2-yl)cyclohexyl]oxycarbonyl}propyl |
| 2-oxopyrrolidinyl |
| 2-(dimethylaminocarbonyl)ethyl |
| aminocarbonylmethyl |
| 2-(aminocarbonyl)ethyl |
| 2-((methylamino)carbonyl)ethyl |
| 4-carboxybutyl |
| 6-carboxyhexanyl |

TABLE 1c-continued

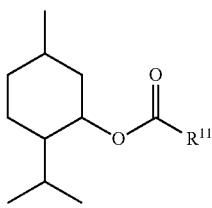
(Ic₂)

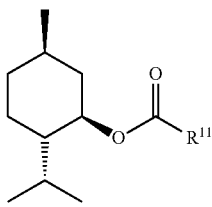
(Ic₂')

| $R^{11}$ |
|---|
| 4-{[(5-methyl-2-(propan-2-yl)cyclohexyl]oxycarbonyl}butyl |
| —CH₂C(O)CH₃ |

In a further embodiment, the menthyl compound has the general formula (Id), preferably the general formula (Id'):

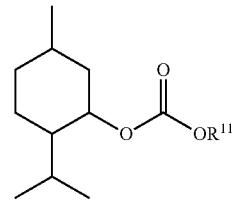
(Id)

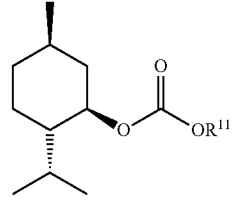
(Id')

wherein $R^{11}$ is selected from the group consisting from alkyl, alkenyl, alkynyl, cycloalkyl, aryl, heteroaryl, and heterocyclyl; wherein each of the alkyl, alkenyl, alkynyl, cycloalkyl, aryl, heteroaryl, and heterocyclyl groups is optionally substituted (e.g., with one or more (in particular 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a $1^{st}$ (or $2^{nd}$ or $3^{rd}$) level substituent). In a preferred embodiment of formula (Id) (or formula (Id')), the menthyl compound has the general formula (Id₁), preferably the general formula (Id₁'):

(Id₁)
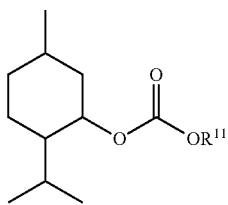

(Id₁')
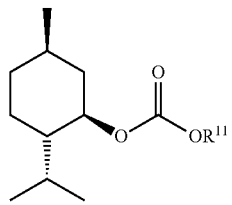

wherein R¹¹ is $C_{1-6}$ alkyl optionally substituted with 1 or 2 —OH. Preferred menthyl compounds of formula (Id), (Id'), (Id₁), or (Id₁') are those having the general formula (Id₂), preferably the general formula (Id₂') shown in Table 1d.

TABLE 1d (Id₂)

(Id₂')

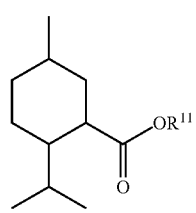

| R¹¹ |
| --- |
| 2-hydroxyethyl |
| 2,3-dihydroxypropyl |
| 2-hydroxypropyl |

In a further embodiment, the menthyl compound has the general formula (Ie), preferably the general formula (Ie'):

(Ie)

(Ie')
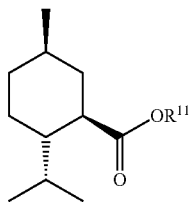

wherein R¹¹ is selected from the group consisting from hydrogen, alkyl, alkenyl, alkynyl, cycloalkyl, aryl, heteroaryl, and heterocyclyl; wherein each of the alkyl, alkenyl, alkynyl, cycloalkyl, aryl, heteroaryl, and heterocyclyl groups is optionally substituted (e.g., with one or more (in particular 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected R³⁰, wherein R³⁰ is a $1^{st}$ (or $2^{nd}$ or $3^{rd}$) level substituent). In a preferred embodiment of formula (Ie) (or formula (Ie')), the menthyl compound has the general formula (Ie₁), preferably the general formula (Ie₁'):

(Ie₁)

(Ie₁')
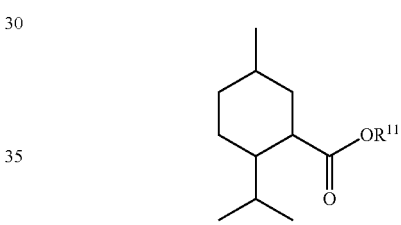

wherein R¹¹ is hydrogen or $C_{1-6}$ alkyl (preferably $C_{1-3}$ alkyl) optionally substituted with 1 or 2 —OH. Preferred menthyl compounds of formula (Ie), (Ie'), (Ie₁), or (Ie₁') are those having the general formula (Ie₂), preferably the general formula (Ie₂') shown in Table 1e.

TABLE 1e (Ie₂)

(Ie₂')
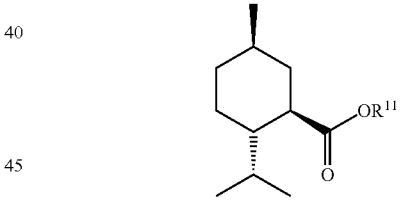

TABLE 1e-continued

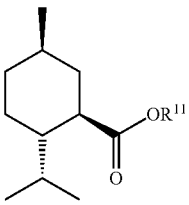

| $R^{11}$ |
|---|
| H |
| 2-hydroxyethyl |
| 2,3-dihydroxypropyl |

In one embodiment, the aliphatic amide compound has the general formula (IIa) or (IIb):

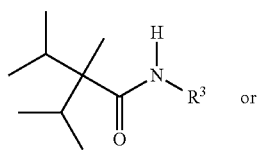 (IIa)

or

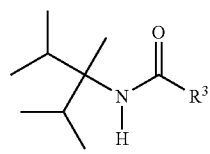 (IIb)

wherein $R^3$ is selected from the group consisting of alkyl, cycloalkyl, aryl, heteroaryl and heterocyclyl, wherein each of the alkyl, cycloalkyl, aryl, heteroaryl, and heterocyclyl groups is optionally substituted (e.g., with one or more (in particular 1 to the maximum number of hydrogen atoms bound to the alkyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a $1^{st}$ (or $2^{nd}$ or $3^{rd}$) level substituent). In a preferred embodiment of formula (II), the aliphatic amide compound has the general formula (IIa$_1$) or (IIb$_1$):

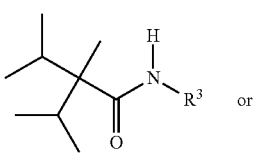 (IIa$_1$)

or

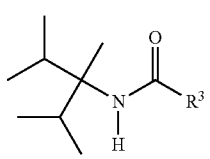 (IIb$_1$)

wherein $R^3$ is selected from the group consisting of $C_{1-6}$ alkyl (preferably $C_{1-3}$ alkyl) and 5- to 10-membered heterocyclyl (preferably 1,3-benzodioxolyl), wherein each of the $C_{1-6}$ alkyl (preferably $C_{1-3}$ alkyl) and 5- to 10-membered heterocyclyl (preferably 1,3-benzodioxolyl) groups is optionally substituted with one $R^{30}$ (e.g., —OH, —OC$_{1-6}$ alkyl or 5- or 6-membered heteroaryl containing 1 or 2 ring nitrogen atoms). Preferred aliphatic amide compounds of formula (IIa), (IIb), (IIa$_1$) or (IIb$_1$) are those having the formula (IIa$_2$) or (IIb$_2$) shown in Table 2.

TABLE 2

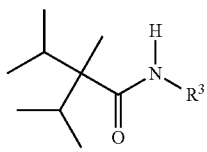 (IIa$_2$)

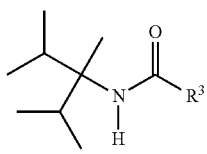 (IIb$_2$)

| $R^3$ |
|---|
| methyl |
| 2-hydroxyethyl |
| 3-propoxypropyl |
| 3-butoxypropyl |
| 2-(2-pyridyl)ethyl |
| 1,3-benzodioxol-5-yl |

Particularly preferred examples of the aliphatic amide compound of formula (IIa), (IIb), (IIa$_1$), (IIb$_1$), (IIa$_2$), or (IIb$_2$) include N,2,3-trimethyl-2-(propan-2-yl)butanamide (also designated as WS-23), N-(2-hydroxyethyl)-2,3-dimethyl-2-(propan-2-yl)butanamide, N-(1,3-benzodioxol-5-yl)-2,3-dimethyl-2-(propan-2-yl)butanamide, 2,3-dimethyl-2-(propan-2-yl)-N-[2-(pyridin-2-yl)ethyl]butanamide, and N-(2,3,4-trimethylpentan-3-yl)-1,3-benzodioxole-5-carboxamide.

In one embodiment, the dihydropyrimidine compound has the general formula (III):

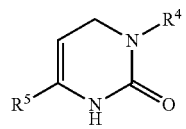 (III)

wherein $R^4$ and $R^5$ are each independently selected from the group consisting of aryl and heteroaryl, wherein each of the aryl and heteroaryl groups is optionally substituted (e.g., with one or more (in particular 1 to the maximum number of hydrogen atoms bound to the aryl or heteroaryl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a $1^{st}$ (or $2^{nd}$ or $3^{rd}$) level substituent). In a preferred embodiment of formula (III), the dihydropyrimidine compound has the general formula (III$_1$):

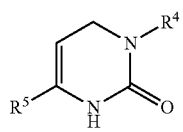

(III$_1$)

wherein R$^4$ and R$^5$ are independently selected from the group consisting of 6-membered aryl and 5- to 6-membered heteroaryl (preferably both of R$^4$ and R$^5$ are phenyl or 5- to 6-membered heteroaryl, more preferably phenyl), wherein each of the 6-membered aryl and 5- to 6-membered heteroaryl groups is optionally substituted with 1 or 2 independently selected R$^{30}$ (e.g., C$_{1-3}$ alkyl (optionally substituted with 1 —OH), —O(C$_{1-3}$ alkyl), —OH, halogen, nitro, and —C(O)NH$_2$)). Preferred dihydropyrimidine compounds of formula (III) (or formula (III$_1$)) are those having the formula (III$_2$) shown in Table 3.

TABLE 3

(III$_2$)

| R$^4$ | R$^5$ |
|---|---|
| 2-hydroxyphenyl | 3-nitrophenyl |
| 2-hydroxyphenyl | 3-methylphenyl |
| 2-hydroxyphenyl | 3-chlorophenyl |
| 3-hydroxyphenyl | 3-nitrophenyl |
| 2-methoxyphenyl | 3-nitrophenyl |
| 3-methoxyphenyl | 3-nitrophenyl |
| 4-hydroxy-2-methylphenyl | 3-nitrophenyl |
| 4-hydroxy-3-methylphenyl | 3-nitrophenyl |
| 2-(hydroxymethyl)phenyl | 3-nitrophenyl |
| 2-(aminocarbonyl)phenyl | 3-nitrophenyl |
| 2-chlorophenyl | 3-nitrophenyl |
| 2-bromophenyl | 3-nitrophenyl |
| 2-iodophenyl | 3-nitrophenyl |
| 3-chlorophenyl | 3-nitrophenyl |
| 3-bromophenyl | 3-nitrophenyl |
| 3-iodophenyl | 3-nitrophenyl |

Particularly preferred examples of the dihydropyrimidine compound of formula (III), (III$_1$), or (III$_2$) include 3-(2-hydroxyphenyl)-6-(3-nitrophenyl)-3,4-dihydropyrimidin-2(1H)-one (also designated as icilin), 3-(2-hydroxyphenyl)-6-(3-methylphenyl)-3,4-dihydropyrimidin-2(1H)-one, 6-(3-chlorophenyl)-3-(2-hydroxyphenyl)-3,4-dihydropyrimidin-2(1H)-one, 3-(3-hydroxyphenyl)-6-(3-nitrophenyl)-3,4-dihydropyrimidin-2(1H)-one, 3-(2-methoxyphenyl)-6-(3-nitrophenyl)-3,4-dihydropyrimidin-2(1H)-one, 3-(3-methoxyphenyl)-6-(3-nitrophenyl)-3,4-dihydropyrimidin-2 (1H)-one, 3-(2-hydroxy-4-methylphenyl)-6-(3-nitrophenyl)-3,4-dihydropyrimidin-2(1H)-one, 3-(2-hydroxy-3-methylphenyl)-6-(3-nitrophenyl)-3,4-dihydropyrimidin-2(1H)-one, 3-[2-(hydroxymethyl)phenyl]-6-(3-nitrophenyl)-3,4-dihydropyrimidin-2(1H)-one, 2-[4-(3-nitrophenyl)-2-oxo-3,6-dihydropyrimidin-1 (2H)-yl]benzamide, 3-(2-chlorophenyl)-6-(3-nitrophenyl)-3,4-dihydropyrimidin-2(1H)-one, 3-(2-bromophenyl)-6-(3-nitrophenyl)-3,4-dihydropyrimidin-2(1H)-one, 3-(2-iodophenyl)-6-(3-nitrophenyl)-3,4-dihydropyrimidin-2 (1H)-one, 3-(3-chlorophenyl)-6-(3-nitrophenyl)-3,4-dihydropyrimidin-2(1H)-one, 3-(3-bromophenyl)-6-(3-nitrophenyl)-3,4-dihydropyrimidin-2(1H)-one, and 3-(3-iodophenyl)-6-(3-nitrophenyl)-3,4-dihydropyrimidin-2 (1H)-one.

Further exemplary TRMP8-agonists which may be used according to the present invention include the compounds shown in Table 4.

TABLE 4

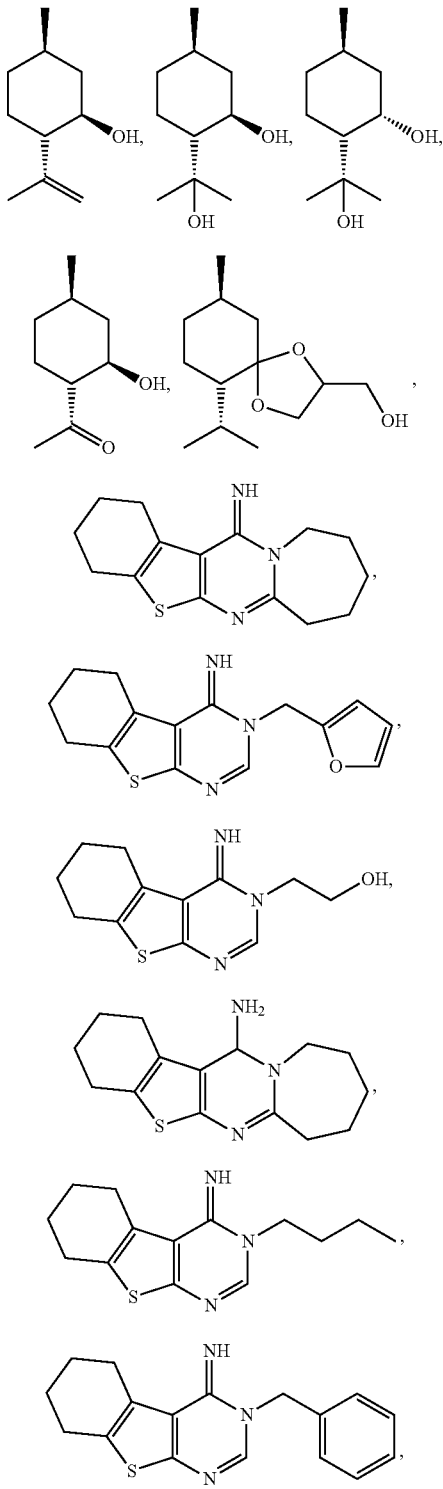

TABLE 4-continued

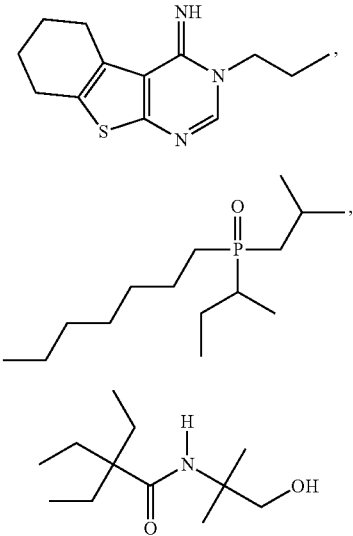

Particularly preferred TRMP8-agonists suitable for the present invention are selected from the group consisting of N-(4-methoxyphenyl)-5-methyl-2-(1-methylethyl)cyclohexanecarboxamide (WS-12), N-ethyl-5-methyl-2-(1-methylethyl)cyclohexanecarboxamide (WS-3), ethyl 3-({[5-methyl-2-(propan-2-yl)cyclohexyl]carbonyl}amino) propanoate (also designated as ethyl 3-(p-menthane-3-carboxamido)acetate or WS-5), 5-methyl-2-(propan-2-yl)-N-[2-(pyridin-2-yl)ethyl]cyclohexanecarboxamide (also designated as N-(2-(pyridin-2-yl)ethyl)-3-p-menthanecarboxamide or FEMA-4549), N,2,3-trimethyl-2-(propan-2-yl) butanamide (also designated as WS-23), N-(2-hydroxyethyl)-2,3-dimethyl-2-(propan-2-yl)butanamide, N-(1,3-benzodioxol-5-yl)-2,3-dimethyl-2-(propan-2-yl) butanamide, 2,3-dimethyl-2-(propan-2-yl)-N-[2-(pyridin-2-yl)ethyl]butanamide, N-(2,3,4-trimethylpentan-3-yl)-1,3-benzodioxole-5-carboxamide, 3-(2-hydroxyphenyl)-6-(3-nitrophenyl)-3,4-dihydropyrimidin-2(1H)-one (also designated as icilin), 3-(2-hydroxyphenyl)-6-(3-methylphenyl)-3,4-dihydropyrimidin-2(1H)-one, 6-(3-chlorophenyl)-3-(2-hydroxyphenyl)-3,4-dihydropyrimidin-2(1H)-one, 3-(3-hydroxyphenyl)-6-(3-nitrophenyl)-3,4-dihydropyrimidin-2(1H)-one, 3-(2-methoxyphenyl)-6-(3-nitrophenyl)-3,4-dihydropyrimidin-2(1H)-one, 3-(3-methoxyphenyl)-6-(3-nitrophenyl)-3,4-dihydropyrimidin-2(1H)-one, 3-(2-hydroxy-4-methylphenyl)-6-(3-nitrophenyl)-3,4-dihydropyrimidin-2(1H)-one, 3-(2-hydroxy-3-methylphenyl)-6-(3-nitrophenyl)-3,4-dihydropyrimidin-2(1H)-one, 3-[2-(hydroxymethyl)phenyl]-6-(3-nitrophenyl)-3,4-dihydropyrimidin-2(1H)-one, 2-[4-(3-nitrophenyl)-2-oxo-3,6-dihydropyrimidin-1(2H)-yl]benzamide, 3-(2-chlorophenyl)-6-(3-nitrophenyl)-3,4-dihydropyrimidin-2(1H)-one, 3-(2-bromophenyl)-6-(3-nitrophenyl)-3,4-dihydropyrimidin-2(1H)-one, 3-(2-iodophenyl)-6-(3-nitrophenyl)-3,4-dihydropyrimidin-2(1H)-one, 3-(3-chlorophenyl)-6-(3-nitrophenyl)-3,4-dihydropyrimidin-2(1H)-one, 3-(3-bromophenyl)-6-(3-nitrophenyl)-3,4-dihydropyrimidin-2(1H)-one, and 3-(3-iodophenyl)-6-(3-nitrophenyl)-3,4-dihydropyrimidin-2(1H)-one, e.g., a compound selected from the group consisting of 3-(2-hydroxyphenyl)-6-(3-nitrophenyl)-3,4-dihydropyrimidin-2(1H)-one (icilin), N-(4-methoxyphenyl)-5-methyl-2-(1-methylethyl)cyclohexanecarboxamide (WS-12), and N-ethyl-5-methyl-2-(1-methylethyl)cyclohexanecarboxamide (WS-3), in particular icilin.

It is intended that the TRMP8-agonists used according to the present invention (in particular, the TRMP8-agonists of any one of formulas (I), (I'), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie'), (Ie$_1$), (Ie$_1$'), (Ie$_2$), (Ie$_2$'), (IIa), (IIb), (IIa$_1$), (IIb$_1$), (IIa$_2$), (IIb$_2$), (III), (III$_1$), (III$_2$), such as those depicted in Tables 1a, 1b, 1c, 1d, 1e, 2, 3, and 4, above) encompass not only the compounds as depicted but also their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof.

The TRMP8-agonists used according to the present invention (in particular, the TRMP8-agonists of any one of formulas (I), (I'), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie'), (Ie$_1$), (Ie$_1$'), (Ie$_2$), (Ie$_2$'), (IIa), (IIb), (IIa$_1$), (IIb$_1$), (IIa$_2$), (IIb$_2$), (III), (III$_1$), (III$_2$), such as those depicted in Tables 1a, 1b, 1c, 1d, 1e, 2, 3, and 4, above) which contain a basic functionality may form salts with a variety of inorganic or organic acids. The TRMP8-agonists according to the present invention (in particular, the TRMP8-agonists of any one of formulas (I), (I'), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie'), (Ie$_1$), (Ie$_1$'), (Ie$_2$), (Ie$_2$'), (IIa), (IIb), (IIa$_1$), (IIb$_1$), (IIa$_2$), (IIb$_2$), (III), (III$_1$), (III$_2$), such as those depicted in Tables 1a, 1b, 1c, 1d, 1e, 2, 3, and 4, above) which contain an acidic functionality may form salts with a variety of inorganic or organic bases. Exemplary inorganic and organic acids/bases as well as exemplary acid/base addition salts of the TRMP8-agonists used according to the present invention are given in the definition of "pharmaceutically acceptable salt" in the section "Pharmaceutical composition", below. The TRMP8-agonists used according to the present invention (in particular, the TRMP8-agonists of any one of formulas (I), (I'), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie'), (Ie$_1$), (Ie$_1$'), (Ie$_2$), (Ie$_2$'), (IIa), (IIb), (IIa$_1$), (IIb$_1$), (IIa$_2$), (IIb$_2$), (III), (III$_1$), (III$_2$), such as those depicted in Tables 1a, 1b, 1c, 1d, 1e, 2, 3, and 4, above) which contain both basic and acidic functionalities may be converted into either base or acid addition salt. The neutral forms of the TRMP8-agonists used according to the present invention (in particular, the TRMP8-agonists of any one of formulas (I), (I'), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie'), (Ie$_1$), (Ie$_1$'), (Ie$_2$), (Ie$_2$'), (IIa), (Ib), (IIa$_1$), (IIb), (IIa$_2$), (IIb$_2$), (III), (III$_1$), (III$_2$), such as those depicted in Tables 1a, 1b, 1c, 1d, 1e, 2, 3, and 4, above) may be regenerated by contacting the salt with a base or acid and isolating the parent compound in the conventional manner.

The TRMP8-agonists used according to the present invention (in particular, the TRMP8-agonists of any one of formulas (I), (I'), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie), (Ie$_1$), (Ie'), (Ie$_2$), (Ie$_2$), (IIa), (IIb), (IIa$_1$), (IIb$_1$), (IIa$_2$), (IIb$_2$), (III), (III$_1$), (III$_2$), such as those depicted in Tables 1a, 1b, 1c, 1d, 1e, 2, 3, and 4, above) may be in a prodrug form. Prodrugs of the TRMP8-agonists used according to the present invention are those compounds that upon administration to an individual undergo chemical conversion under physiological conditions to provide the TRMP8-agonists according to the present invention (in particular, the TRMP8-agonists of any one of formulas (I), (I'), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie'), (Ie$_1$), (Ie$_1$'), (Ie$_2$), (Ie$_2$'), (IIa), (IIb), (IIa$_1$), (IIb$_1$), (IIa$_2$), (IIb$_2$), (III), (III$_1$), (III$_2$), such as those depicted in Tables 1a, 1b, 1c, 1d, 1e, 2, 3, and 4, above). Additionally, prodrugs can be converted to the TRMP8-agonists used according to the present invention (in particular, the TRMP8-agonists of any one of formulas (I), (I'), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie'), (Ie$_1$), (Ie$_1$'), (Ie$_2$), (Ie$_2$'), (IIa), (IIb), (IIa$_1$), (IIb$_1$), (IIa$_2$), (IIb$_2$), (III), (III$_1$), (III$_2$), such as those depicted in Tables 1a, 1b, 1c, 1d, 1e, 2, 3, and 4, above) by chemical or biochemical methods in an ex vivo environment. For example, prodrugs can be slowly converted to the TRMP8-agonists used according to the present invention (in particular, the TRMP8-agonists of any one of formulas (I), (I'), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie'), (Ie$_1$), (Ie$_1$'), (Ie$_2$), (Ie$_2$'), (IIa), (IIb), (IIa$_1$), (IIb$_1$), (IIa$_2$), (IIb$_2$), (III), (III$_1$), (III$_2$), such as those depicted in Tables 1a, 1b, 1c, 1d, 1e, 2, 3, and 4, above) when, for example, placed in a transdermal patch reservoir with a suitable enzyme or chemical reagent. Exemplary prodrugs are esters or amides which are hydrolyzable in vivo.

The TRMP8-agonists used according to the present invention (in particular, the TRMP8-agonists of any one of formulas (I), (I'), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie'), (Ie$_1$), (Ie$_1$'), (Ie$_2$), (Ie$_2$'), (IIa), (IIb), (IIa$_1$), (IIb$_1$), (IIa$_2$), (IIb$_2$), (III), (III$_1$), (III$_2$), such as those depicted in Tables 1a, 1b, 1c, 1d, 1e, 2, 3, and 4, above) can be prepared as described in the literature (cf., e.g., WO 2012/061698, WO 2008/039522, and WO 2004/026840, Bharate and Bharate (Chem. Neurosci. 3 (2012), 248-267), and Leffingwell & Associates (www.leffingwell.com/cooler_than_menthol.htm) or prepared by methods analogous thereto, which are readily known and available to one of ordinary skill in the art of organic synthesis.

Figure 1:
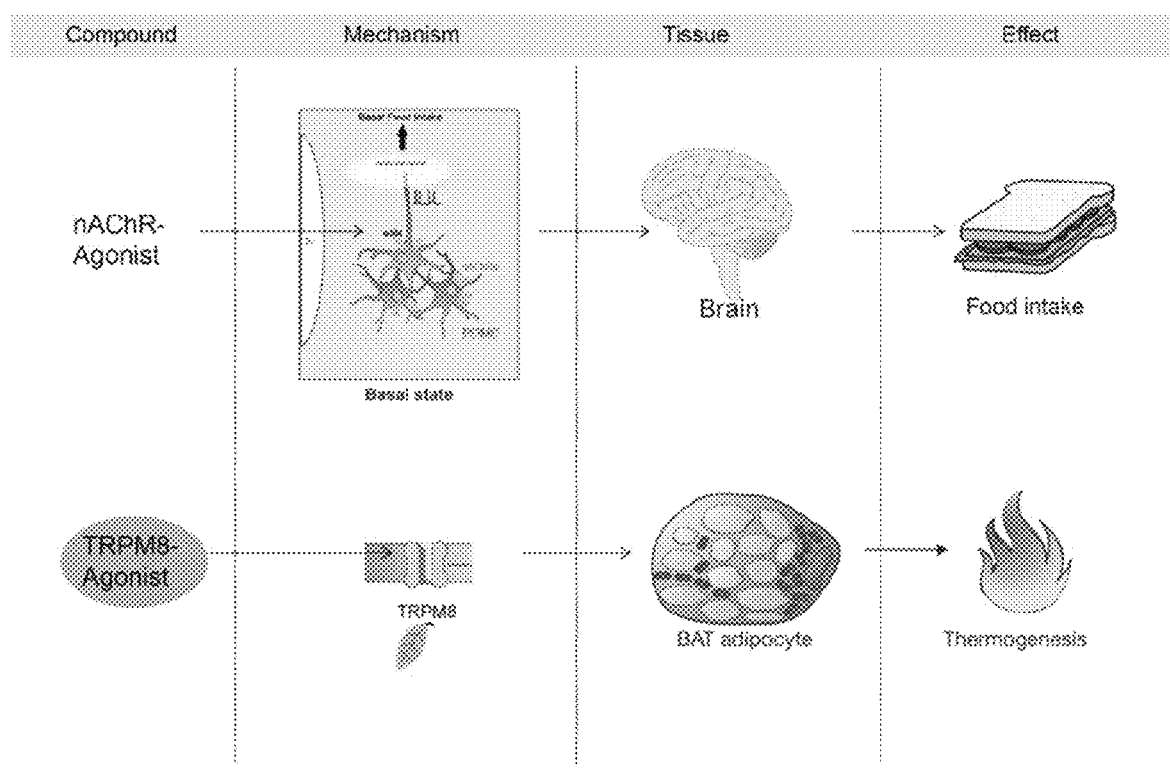
FIG. 1: General schemes of proposed effector mechanisms

Without being bound to any theory, it is believed that generally, TRMP8-agonists act on brown fat tissues (e.g., brown adipose tissue (BAT)), where they mimic cold exposure and increase thermogenesis; cf. FIG. 1.

nAChR-Agonists

A further component of the composition of the present invention is an agonist of the nicotinic acetylcholine receptor (nAChR-agonist). According to the present invention, any nAChR-agonist may be used, e.g., any of those described in WO 2011/080751, WO 2007/100430, WO 2005/117860, and WO 03/037329. Examples of suitable nAChR-agonists include those selected from the group consisting of a dimethylphenylpiperazinium (DMPP) salt or an analogue thereof, cytisine or an analogue thereof, 4-(trifluoromethyl)-10-azatricyclo[6.3.1.0$^{2,7}$]dodeca-2,4,6-triene (CP-601932) or an analogue thereof, nicotine or an analogue thereof, 6-[5-fluoro-2-(pyridin-3-yl)phenoxy]-3-azabicyclo[3.2.1]octane (PF-4575180) or an analogue thereof, epibatidine or an analogue thereof, acetylcholine or an analogue thereof, 3-methyl-5-[(2S)-1-methylpyrrolidin-2-yl]-1,2-oxazole (ABT-418) or an analogue thereof, 3-[(3E)-3-[(2,4-dimethoxyphenyl)methylidene]-5,6-dihydro-4H-pyridin-2-yl]pyridine (GTS-21) or an analogue thereof, lobeline or an analogue thereof, and 4-{[2-(1-methyl-2-pyrrolidinyl)ethyl]thio}phenol (SIB-1553A).

In one embodiment, the nAChR-agonist is a dimethylphenylpiperazinium (DMPP) salt or an analogue thereof having the general formula (IV):

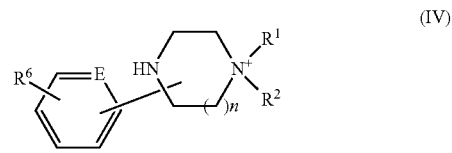

(IV)

wherein $R^1$ and $R^2$ are each independently selected from the group consisting of H and alkyl, wherein the alkyl group is optionally substituted (e.g., with one or more (in particular 1 to the maximum number of hydrogen atoms bound to the alkyl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a 1$^{st}$ (or 2$^{nd}$ or 3$^{rd}$) level substituent); $R^6$ is absent or, when present (replacing one hydrogen atom), is selected from the group consisting of alkyl, halogen, nitro, cyano, isocyano, cyanato, isocyanato, thiocyanato, isothiocyanato, azido, amino, —S(O)$_{1-2}$-(amino), —OS(O)$_{1-2}$-(amino), -(imino)-S(O)$_{1-2}$-(amino), and —Z—$R^{11}$, wherein Z is —O—, —S(O)$_{0-2}$—, —S(O)$_{1-2}$O—, —OS(O)$_{0-2}$—, —OS(O)$_{1-2}$O—, -(imino)-O—, -(imino)-S(O)$_{1-2}$—, -(imino)-S(O)$_{1-2}$—O—, —C(=X)—, —C(=X)X—, —XC(=X)—, and —XC(=X)X—, wherein the alkyl group is optionally substituted (e.g., with one or more (in particular 1 to the maximum number of hydrogen atoms bound to the alkyl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a 1$^{st}$ (or 2$^{nd}$ or 3$^{rd}$) level substituent), each X is independently selected from O, S, and imino, and $R^{11}$ is selected from hydrogen, alkyl, alkenyl, alkynyl, cycloalkyl, heterocyclyl, aryl, and heteroaryl; wherein each of the alkyl, alkenyl, alkynyl, cycloalkyl, heterocyclyl, aryl, and heteroaryl groups is optionally substituted (e.g., with one or more (in particular 1 to the maximum number of hydrogen atoms bound to the alkyl, alkenyl, alkynyl, cycloalkyl, heterocyclyl, aryl, or heteroaryl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a 1$^{st}$ (or 2$^{nd}$ or 3$^{rd}$) level substituent); E is N or CH; and n is 1 or 2. The counter anion may be any anion, preferably an anion derived from a pharmaceutically acceptable acid (e.g., one of the salts specified under the chapter "Pharmaceutical compositions", below, including acetate, ascorbate, aspartate, benzenesulfonate, benzoate, bicarbonate, bisulfate, borate, bromide, butyrate, carbonate, chloride, citrate, dodecylsulfate, edetate, estolate, ethanesulfonate, formate, fumarate, galactate, galacturonate, gluconate, glutamate, glycerophosphate, hemisulfate, heptanoate, hexanoate, 2-hydroxy-ethanesulfonate, iodide, isobutyrate, isothionate, lactate, laurate, lauryl sulfate, malate, maleate, malonate, mandelate, mesylate, methanesulfonate, methylsulfate, 2-naphthalenesulfonate, nitrate, oleate, oxalate, palmitate, phosphate/diphosphate, propionate, salicylate, stearate, sulfate, suberate, succinate, tartrate, tosylate, undecanoate, or valerate). In a preferred embodiment of formula (IV), the DMPP salt has the general formula (IV₁):

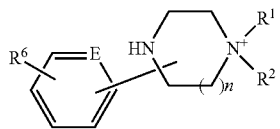

wherein $R^1$ and $R^2$ are each independently selected from the group consisting of H and $C_{1-3}$ alkyl (i.e., methyl, ethyl, n-propyl, or iso-propyl); and $R^6$ is either absent or selected from the group consisting of halogen, —CN, and $C_{1-3}$ alkyl.

Preferred DMPP salts or analogues thereof having formula (IV) (or formula (IV₁)) are those having the formula (IV₂) shown in Table 5.

TABLE 5

(IV₂)

| $R^1$ | $R^2$ | $R^6$ | E | n |
|---|---|---|---|---|
| —CH₃ | —CH₃ | — | CH | 1 |
| —CH₃ | —CH₂CH₂CH₃ | — | CH | 1 |
| —CH₃ | —CH₂CH₂CH₃ | — | CH | 2 |
| —CH₂CH₃ | —CH₂CH₃ | — | CH | 1 |
| —CH₂CH₃ | —CH₂CH₃ | — | CH | 2 |
| —CH₂CH₃ | —CH₃ | — | CH | 1 |
| —CH₂CH₃ | —CH₃ | — | CH | 2 |
| —CH₃ | —CH₃ | — | CH | 2 |
| —CH₃ | H | — | N | 1 |
| H | H | halogen | N | 1 |

Particularly preferred examples of DMPP salts or analogues thereof having formula (IV), (IV₁), or (IV₂) include DMPP, i.e., a compound of formula (IV₂), wherein $R^6$ is absent; E is CH; the phenyl ring is attached to the piperazinyl moiety by the $2^{nd}$ N atom (i.e., the N atom which does not bear $R^1/R^2$); n is 1; and $R^1$ and $R^2$ are each methyl, e.g., as halogenide (such as chloride, bromide, or iodide).

In one embodiment, the nAChR-agonist is cytisine or an analogue having the general formula (V), preferably the general formula (V'):

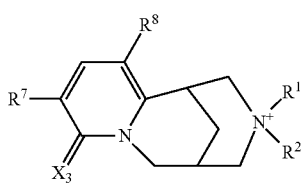

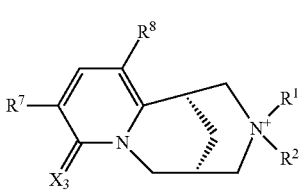

wherein $R^7$ and $R^8$ are each independently selected from the group consisting of hydrogen, alkyl, alkenyl, aryl, halogen, —CN, —NC, —NCO, —CNO, —SCN, —NCS, —N₃, —NO₂, —OH, and —NH₂; $X_3$ is selected from O and S; at least one of $R^1$ and $R^2$ is present and $R^1$ and $R^2$ are each independently selected from the group consisting of absent, hydrogen, alkyl, and —Y'—Z', wherein Y' is —S(O)$_{1-2}$—, —S(O)$_{1-2}$O—, —C(=X')—, —C(=X')X'—, and —X'C(=X')—, wherein each X' is independently selected from O, S, and imino, and Z' is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl groups is optionally substituted (e.g., with one or more (in particular 1 to the maximum number of hydrogen atoms bound to the alkyl, alkenyl, alkynyl, cycloalkyl, heterocyclyl, aryl, or heteroaryl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a $1^{st}$ (or $2^{nd}$ or $3^{rd}$) level substituent). If $R^1$ and $R^2$ are present, the compound of formula (V) contains a quaternary nitrogen atom. In this case, the corresponding counter anion may be any anion, preferably an anion derived from a pharmaceutically acceptable acid as described herein. In a preferred embodiment of formula (V) (or formula (V')), the nAChR-agonist has the general formula (V₁), preferably the general formula (V₁'):

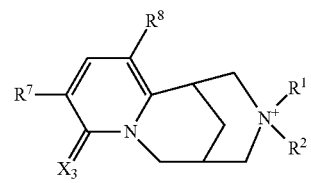

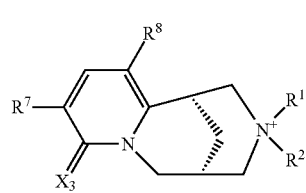

wherein $R^7$ and $R^8$ are independently selected from the group consisting of hydrogen, $C_{1-3}$ alkyl, phenyl, vinyl, and halogen; $X_3$ is selected from O and S; and $R^1$ and $R^2$ are independently selected from the group consisting of absent, hydrogen, and $C_{1-3}$ alkyl (e.g., methyl or ethyl) optionally substituted with 1 phenyl. Preferred compounds of formula (V), (V'), (V₁), or (V₁') are those having the general formula (V₂), preferably the general formula (V₂) shown in Table 6.

TABLE 6

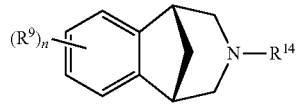

(V₂)

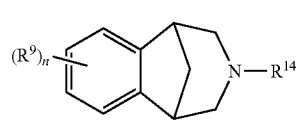

(V₂')

| R¹ | R² | R⁷ | R⁸ | X₃ |
|---|---|---|---|---|
| H | — | H | H | O |
| —(CH₂)₃CH₃ | — | H | H | O |
| H | — | halogen | halogen | O |
| H | — | H | H | S |
| —CH₃ | —CH₃ | halogen | halogen | O |
| —CH₃ | —CH₃ | halogen | halogen | S |
| —CH₂CH₃ | —CH₃ | H | H | O |
| —CH₂CH₃ | —CH₃ | H | H | S |
| —CH₂CH₃ | —CH₂CH₃ | H | H | O |
| —CH₂CH₃ | —CH₂CH₃ | H | H | S |
| H | — | Br | H | O |
| H | — | H | Br | O |
| H | — | Cl | H | O |
| H | — | H | Cl | O |
| H | — | F | H | O |
| H | — | H | F | O |
| H | — | F | F | O |
| H | — | —CH₂CH₃ | H | O |
| H | — | H | —CH₂CH₃ | O |
| H | — | —CH₂CH₃ | —CH₂CH₃ | O |
| H | — | —CH₃ | H | O |
| H | — | H | —CH₃ | O |
| H | — | —CH₃ | —CH₃ | O |
| H | — | phenyl | H | O |
| H | — | H | phenyl | O |
| H | — | phenyl | phenyl | O |
| H | — | vinyl | H | O |
| H | — | H | vinyl | O |
| H | — | vinyl | vinyl | O |
| —CH₃ | — | Br | H | O |
| benzyl | — | Br | H | O |
| benzyl | — | Cl | H | O |

Particularly preferred examples of compounds of formula (V), (V'), (V₁), (V₁'), (V₂), or (V₂') include cytisine (i.e., the compound of formula (V'), wherein R¹ is H; R² is absent; R⁷ and R⁸ are H; and X is O).

In one embodiment, the nAChR-agonist is 4-(trifluoromethyl)-10-azatricyclo[6.3.1.0²,⁷]dodeca-2,4,6-triene (CP-601932) or an analogue thereof having the general formula (VI), preferably the general formula (VI'):

(VI)

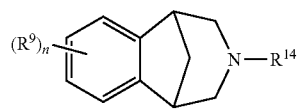

(VI')

wherein n is 0, 1, or 2; each $R^9$ is independently selected from the group consisting of halogen, nitro, cyano, isocyano, cyanato, isocyanato, thiocyanato, isothiocyanato, azido, alkyl, alkenyl, alkynyl, cycloalkyl, heterocyclyl, aryl, heteroaryl, amino, —S(O)$_{1-2}$-(amino), —OS(O)$_{1-2}$-(amino), -(imino)-S(O)$_{1-2}$-(amino), and —Z—$R^{11}$, wherein Z is —O—, —S(O)$_{0-2}$—, —S(O)$_{1-2}$O—, —OS(O)$_{0-2}$—, —OS(O)$_{1-2}$O—, -(imino)-O—, -(imino)-S(O)$_{1-2}$—, -(imino)-S(O)$_{1-2}$—O—, —C(=X)—, —C(=X)X—, —XC(=X)—, and —XC(=X)X—, wherein each X is independently selected from O, S, and imino, and $R^{11}$ is selected from hydrogen, alkyl, alkenyl, alkynyl, cycloalkyl, heterocyclyl, aryl, and heteroaryl; wherein each of the alkyl, alkenyl, alkynyl, cycloalkyl, heterocyclyl, aryl, and heteroaryl groups (of $R^9$ and $R^{11}$) is optionally substituted (e.g., with one or more (in particular 1 to the maximum number of hydrogen atoms bound to the alkyl, alkenyl, alkynyl, cycloalkyl, heterocyclyl, aryl, or heteroaryl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a $1^{st}$ (or $2^{nd}$ or $3^{rd}$) level substituent); or two $R^9$ (which are preferably attached to C atoms that are directly adjacent) may join together with the atoms to which they are attached to form a 5- to 8-membered ring which is optionally substituted (e.g., with one or more (in particular 1 to the maximum number of hydrogen atoms bound to the 5- to 8-membered ring, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a $1^{st}$ (or $2^{nd}$ or $3^{rd}$) level substituent); and $R^{14}$ is selected from the group consisting of hydrogen, alkyl, alkenyl, and —Y'—Z', wherein Y' is —S(O)$_{1-2}$—, —S(O)$_{1-2}$O—, —C(=X')—, —C(=X')X'—, and —X'C(=X')—, wherein each X' is independently selected from O, S, and imino, and Z' is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl groups is optionally substituted (e.g., with one or more (in particular 1 to the maximum number of hydrogen atoms bound to the alkyl, alkenyl, alkynyl, cycloalkyl, heterocyclyl, aryl, or heteroaryl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a $1^{st}$ (or $2^{nd}$ or $3^{rd}$) level substituent). In a preferred embodiment of formula (VI) (or formula (VI')), the nAChR-agonist has the general formula (VI₁), preferably the general formula (VI₁'):

(VI₁)

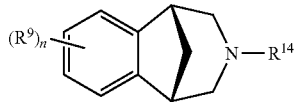

(VI₁')

wherein $R^9$ is independently selected from the group consisting of $C_{1-3}$ alkyl, —$CF_3$, halogen, —CN, —$NO_2$, —$NH_2$, —OH, acetyl, —$S(O)_2N(CH_3)_2$, 5-membered heteroaryl (optionally substituted with 1 $C_{1-3}$ alkyl), phenyl, or —$SO_2$-(5-membered heterocyclyl); or two $R^9$ (which are preferably attached to C atoms that are directly adjacent) may join together with the atoms to which they are attached to form a 6-membered heteroareno containing 1 or 2 ring nitrogen atoms (e.g., pyrazino, pyridino, pyrimidino, or pyridazino); and $R^{14}$ is hydrogen. Preferred compounds of formula (VI), (VI'), (VI$_1$), or (VI$_1$') are those having the general formula (VI$_2$), preferably the general formula (VI$_2$') shown in Table 7.

TABLE 7

(VI$_2$)

$(R^9)_n$ ... N—$R^{14}$ (VI$_2$')

$(R^9)_n$ ... N—$R^{14}$

| $R^9$ (position) | $R^9$ (position) | n | $R^{14}$ |
|---|---|---|---|
| —$CF_3$ (4) | — | 1 | H |
| — | — | 0 | H |
| —$CH_3$ (4) | — | 1 | H |
| F (4) | — | 1 | H |
| —$CF_3$ (3) | — | 1 | H |
| F (3) | — | 1 | H |
| —$NO_2$ (4) | — | 1 | H |
| —$NH_2$ (4) | — | 1 | H |
| —NHC(O)$CH_3$ (4) | — | 1 | H |
| —OH (4) | —NHC(O)(2-fluorophenyl) (5) | 2 | H |
| Cl (4) | — | 1 | H |
| —CN (4) | — | 1 | H |
| 5-methyl-1,2,4-oxadiazol-3-yl (4) | — | 1 | H |
| —C(O)$CH_3$ (4) | — | 1 | H |
| —OH (4) | — | 1 | H |
| 2-methyl-2H-pyrazol-3-yl (4) | — | 1 | H |
| 1-methyl-1H-pyrazol-3-yl (4) | — | 1 | H |
| Cl (4) | Cl (5) | 2 | H |
| —$S(O)_2N(CH_3)_2$ (4) | — | 1 | H |
| 1-pyrrolidinylsulfonyl (4) | — | 1 | H |
| phenyl (3) | — | 1 | H |
| —OH (3) | — | 1 | H |
| F (4) | F (5) | 2 | H |
| pyrazino (4 + 5) | | 2 | H |

Particularly preferred examples of compounds of formula (VI), (VI'), (VI$_1$), (VI$_1$'), (VI$_2$), or (VI$_2$') include 4-(trifluoromethyl)-10-azatricyclo[6.3.1.0$^{2,7}$]dodeca-2,4,6-triene (CP-601932; i.e., the compound of formula (VI'), wherein n is 1; $R^9$ is trifluoromethyl (position 4); and $R^{14}$ is H) and (6R,10S)-7,8,9,10-tetrahydro-6,10-methano-6H-pyrazino[2,3-h]-[3]benzazepine (varenicline, i.e., the compound of formula (VI'), wherein n is 2; the two $R^9$ groups (at positions 4 and 5) join together with the atoms to which they are attached to form pyrazino; and $R^{14}$ is H).

In one embodiment, the nAChR-agonist is nicotine or an analogue thereof having the general formula (VII):

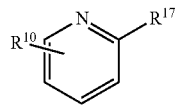

(VII)

wherein $R^{10}$ is independently selected from the group consisting of alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl groups is optionally substituted (e.g., with one or more (in particular 1 to the maximum number of hydrogen atoms bound to the alkyl, alkenyl, alkynyl, cycloalkyl, heterocyclyl, aryl, or heteroaryl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a 1$^{st}$ (or 2$^{nd}$ or 3$^{rd}$) level substituent); and $R^{17}$ is selected from the group consisting of hydrogen and halogen. In a preferred embodiment of formula (VII), the nAChR-agonist has the general formula (VIII):

(VII$_1$)

wherein $R^{10}$ is selected from the group consisting of 3- to 6-membered cycloalkyl (optionally substituted with 1 or 2 independently selected $R^{30}$), 5- to 6-membered heterocyclyl (optionally substituted with 1 or 2 independently selected $R^{30}$), and $C_{1-3}$ alkyl substituted with one 5- to 6-membered heterocyclyl or heteroaryl (optionally substituted with 1 or 2 independently selected $R^{30}$). Preferred compounds of formula (VII) or (VII$_1$) are those having the formula (VII$_2$) shown in Table 8.

TABLE 8

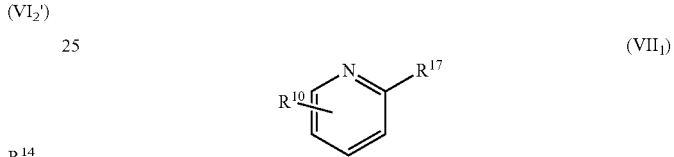

(VII$_2$)

| $R^{10}$ (position) | $R^{17}$ |
|---|---|
| 1-methylpyrrolidin-2-yl (3) | H |
| (1-methylpyrrolidin-2-yl)methyl (3) | H |
| (E)-2-(3-methyl-1,2-oxazol-5-yl)ethenyl (3) | H |
| 2-[(trimethylamino)methyl]cyclopropyl (4) | H |
| 1,1-dimethylpyrrolidin-2-yl (3) | halogen |
| 1,1-dimethylpiperidin-2-yl (3) | halogen |
| 1,1-dimethylpiperidin-2-yl (3) | H |
| 1,1-dimethylpiperidin-2-yl (3) | H |
| (1,1-dimethylpyrrolidin-2-yl)methyl (3) | H |
| (1,1-dimethylpiperidin-2-yl)methyl (3) | H |

Particularly preferred examples of compounds of formula (VII), (VII$_1$), or (VII$_2$) include nicotine (i.e., the compound of formula (VII), wherein $R^{10}$ (at position 3) is 1-methylpyrrolidin-2-yl; and $R^{17}$ is H).

In one embodiment, the nAChR-agonist is 6-[5-fluoro-2-(pyridin-3-yl)phenoxy]-3-azabicyclo[3.2.1]octane (PF-4575180) or an analogue thereof having the general formula (VIII), preferably the general formulöa (VIII'):

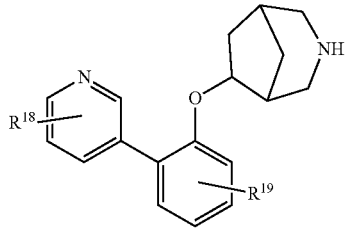

(VIII)

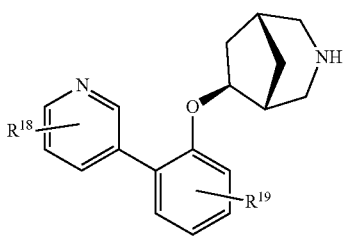

(VIII')

wherein $R^{18}$ and $R^{19}$ are each independently either absent or selected from the group consisting of halogen, nitro, cyano, isocyano, cyanato, isocyanato, thiocyanato, isothiocyanato, azido, alkyl, alkenyl, alkynyl, cycloalkyl, heterocyclyl, aryl, heteroaryl, amino, —S(O)$_{1\text{-}2}$-(amino), —OS(O)$_{1\text{-}2}$-(amino), -(imino)-S(O)$_{1\text{-}2}$-(amino), and —Z—$R^{11}$, wherein Z is —O—, —S(O)$_{0\text{-}2}$—, —S(O)$_{1\text{-}2}$O—, —OS(O)$_{0\text{-}2}$—, —OS(O)$_{1\text{-}2}$O—, -(imino)-O—, -(imino)-S(O)$_{1\text{-}2}$—, -(imino)-S(O)$_{1\text{-}2}$—O—, —C(=X)—, —C(=X)X—, —XC(=X)—, and —XC(=X)X—, wherein each X is independently selected from O, S, and imino, and $R^{11}$ is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl groups is optionally substituted (e.g., with one or more (in particular 1 to the maximum number of hydrogen atoms bound to the alkyl, alkenyl, alkynyl, cycloalkyl, heterocyclyl, aryl, or heteroaryl group, e.g., 1, 2, 3, 4, 5, 6, 7, 8, 9, or up to 10, such as between 1 to 5, 1 to 4, or 1 to 3, or 1 or 2) independently selected $R^{30}$ wherein $R^{30}$ is a 1$^{st}$ (or 2$^{nd}$ or 3$^{rd}$) level substituent). In a preferred embodiment of formula (VIII) (or formula (VIII')), the nAChR-agonist has the general formula (VIII$_1$), preferably the general formula (VIII$_1$'):

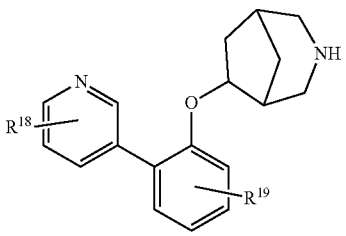

(VIII$_1$)

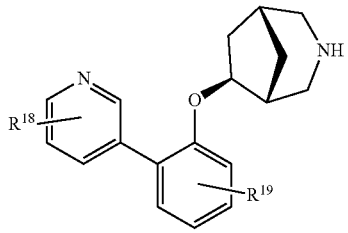

(VIII$_1$')

wherein $R^{18}$ is absent or selected from the group consisting of halogen, C$_{1\text{-}3}$ alkyl, —O(C$_{1\text{-}3}$ alkyl), —NH$_2$, —NHSO$_2$(C$_{1\text{-}3}$ alkyl), —NHC(O)(C$_{1\text{-}3}$ alkyl), and —C(O)NH$_2$; and $R^{19}$ is absent or halogen. Preferred compounds of formula (VIII), (VIII'), (VIII$_1$), or (VIII$_1$') are those having the general formula (VIII$_2$), preferably the general formula (VIII$_2$') shown in Table 9.

TABLE 9

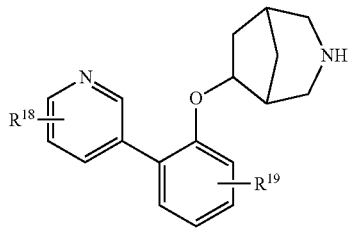

(VIII$_2$)

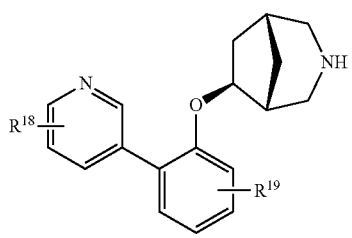

(VIII$_2$')

| $R^{18}$ (position) | $R^{19}$ (position) |
|---|---|
| absent | absent |
| —OCH$_3$ (4) | absent |
| —OCH$_3$ (5) | absent |
| —OH (4) | absent |
| —OH (5) | absent |
| F (4) | absent |
| F (5) | absent |
| —NH$_2$ (4) | absent |
| —NH$_2$ (5) | absent |
| —NHSO$_2$CH$_3$ (4) | absent |
| —NHSO$_2$CH$_3$ (5) | absent |
| —NHSO$_2$CH$_2$CH$_3$ (5) | absent |
| —NHSO$_2$CH(CH$_3$)$_2$ (5) | absent |
| —NHC(O)CH$_3$ (5) | absent |
| —C(O)NH$_2$ (5) | absent |
| absent | F (5) |

Particularly preferred examples of compounds of formula (VIII), (VIII'), (VIII$_1$), (VIII$_1$'), (VIII$_2$), or (VIII$_2$') include 6-[5-fluoro-2-(pyridin-3-yl)phenoxy]-3-azabicyclo[3.2.1]octane (PF-4575180, i.e., the compound of formula (VIII'), wherein $R^{18}$ is absent and $R^{19}$ (at position 5) is F).

In one embodiment, the nAChR-agonist is epibatidine or an analogue thereof having the general formula (IX), preferably the general formula (IX'):

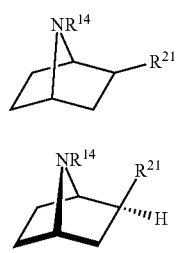

(IX)

(IX')

wherein R[14] is selected from the group consisting of hydrogen, alkyl, and —Y'—Z', wherein Y' is —S(O)$_{1-2}$—, —S(O)$_{1-2}$O—, —C(=X')—, —C(=X')X'—, and —X'C(=X')—, wherein each X' is independently selected from O, S, and imino, and Z' is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl groups is optionally substituted (e.g., with one or more (in particular 1 to the maximum number of hydrogen atoms bound to the alkyl, alkenyl, alkynyl, cycloalkyl, heterocyclyl, aryl, or heteroaryl group, e.g., 1, 2, 3, 4, 5, 6, 7, 8, 9, or up to 10, such as between 1 to 5, 1 to 4, or 1 to 3, or 1 or 2) independently selected R[30], wherein R[30] is a 1$^{st}$ (or 2$^{nd}$ or 3$^{rd}$) level substituent); and R[21] is selected from the group consisting of aryl, heteroaryl, cycloalkyl, and heterocyclyl, wherein each of the aryl, heteroaryl, cycloalkyl, and heterocyclyl groups is optionally substituted (e.g., with one or more (in particular 1 to the maximum number of hydrogen atoms bound to the aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected R[30], wherein R[30] is a 1$^{st}$ (or 2$^{nd}$ or 3$^{rd}$) level substituent). In a preferred embodiment of formula (IX) (or (formula (IX')), the nAChR-agonist has the general formula (IX$_1$), preferably (IX$_1$'):

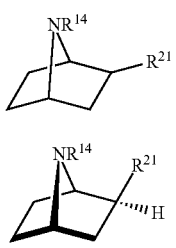

(IX$_1$)

(IX$_1$')

wherein R[14] is pyridyl, oxazolyl, pyridazinyl, pyrrolidinyl, or piperidinyl, wherein each of the pyridyl, oxazolyl, pyridazinyl, pyrrolidinyl, and piperidinyl groups is optionally substituted with 1 or 2 independently selected R[30] (such as halogen, alkyl (e.g., C$_{1-3}$ alkyl), —NH$_2$, —NH(CH$_3$), —N(CH$_3$)$_2$, and —[N(CH$_3$)$_3$]$^+$); and R[21] is selected from the group consisting of H and alkyl (e.g., C$_{1-3}$ alkyl). Preferred compounds of formula (IX), (IX'), (IX$_1$), or (IX$_1$') are those having the general formula (IX$_2$), preferably the general formula (IX$_2$') shown in Table 10.

TABLE 10

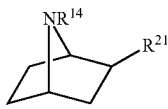

(IX$_2$)

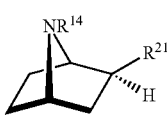

(IX$_2$')

| R[14] | R[21] |
|---|---|
| H | 6-halogenopyridin-3-yl |
| H | 6-chloropyridin-3-yl |
| H | 6-halogeno-5-phenylpyridin-3-yl |
| H | 3-methyl-1,2-oxazol-5-yl |
| H | pyridazin-4-yl |
| —CH$_3$ | 6-halogenopyridin-3-yl |
| H | 1,1-dimethylpyrrolidin-2-yl |
| —CH$_3$ | 1,1-dimethylpyrrolidin-2-yl |
| H | 1,1-dimethylpiperidin-2-yl |
| —CH$_3$ | 1,1-dimethylpiperidin-2-yl |
| H | 2-(trimethylamino)pyridin-5-yl |

Particularly preferred examples of compounds of formula (IX), (IX'), (IX$_1$), (IX$_1$'), (IX$_2$), or (IX$_2$') include epibatidine, i.e., the compound of formula IX', wherein R[14] is H and R[21] is 6-chloropyridin-3-yl.

In one embodiment, the nAChR-agonist is acetylcholine or an analogue thereof having the general formula (X):

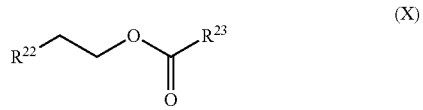

(X)

wherein R[22] is —N(C$_{1-3}$ alkyl)$_3$; and R[23] is selected from —CH$_3$ and —NH(CH)$_3$. In a preferred embodiment of formula (X), R[22] is selected from —N(CH$_3$)$_3$, —N(CH$_3$)(CH$_2$CH$_3$)$_2$, and —N(CH$_2$CH$_3$)$_3$. Preferred compounds of formula (X) are those having the formula (X$_1$) shown in Table 11.

TABLE 11

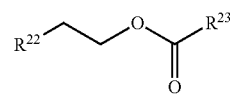

(X$_1$)

| R[22] | R[23] |
|---|---|
| —N(CH$_3$)$_3$ | —CH$_3$ |
| —N(CH$_3$)(CH$_2$CH$_3$)$_2$ | —CH$_3$ |
| —N(CH$_2$CH$_3$)$_3$ | —CH$_3$ |
| —N(CH$_3$)$_3$ | —NH(CH)$_3$ |
| —N(CH$_3$)(CH$_2$CH$_3$)$_2$ | —NH(CH)$_3$ |
| —N(CH$_2$CH$_3$)$_3$ | —NH(CH)$_3$ |

Particularly preferred examples of compounds of formula (X) or (X$_1$) include acetylcholine (i.e., the compound of formula (X), wherein R[22] is —N(CH$_3$)$_3$ and R[23] is —CH$_3$) and N-methylcarbamylcholine (i.e., the compound of formula (X), wherein R[22] is —N(CH$_3$)$_3$ and R[23] is —NH(CH$_3$)$_3$).

In one embodiment, the nAChR-agonist is 3-methyl-5-[(2S)-1-methylpyrrolidin-2-yl]-1,2-oxazole (ABT-418) or an analogue thereof having the general formula (XI), preferably the general formula (XI'):

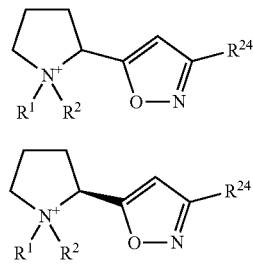

wherein at least one of $R^1$ and $R^2$ is present and $R^1$ and $R^2$ are each independently selected from the group consisting of absent, hydrogen, alkyl, and —Y'—Z', wherein Y' is —S(O)$_{1-2}$—, —S(O)$_{1-2}$O—, —C(=X')—, —C(=X')X'—, and —X'C(=X')—, wherein each X' is independently selected from O, S, and imino, and Z' is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl groups is optionally substituted (e.g., with one or more (in particular 1 to the maximum number of hydrogen atoms bound to the alkyl, alkenyl, alkynyl, cycloalkyl, heterocyclyl, aryl, or heteroaryl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a 1$^{st}$ (or 2$^{nd}$ or 3$^{rd}$) level substituent); and $R^{24}$ is alkyl. If $R^1$ and $R^2$ are present, the compound of formula (X) contains a quaternary nitrogen atom. In this case, the corresponding counter anion may be any anion, preferably derived from a pharmaceutically acceptable acid as described herein. In a preferred embodiment of formula (XI) (or formula (XI')), the nAChR-agonist has the general formula (XI$_1$), preferably the general formula (XI'):

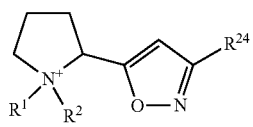

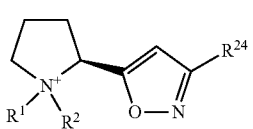

wherein $R^1$ and $R^2$ are each independently selected from the group consisting of hydrogen and $C_{1-6}$ alkyl (e.g., $C_{1-3}$ alkyl such as methyl or ethyl); and $R^{24}$ is $C_{1-3}$ alkyl (e.g., methyl or ethyl, preferably methyl). Preferred compounds of formula (XI), (XI'), (XI$_1$), or (XI$_1$') are those having the general formula (XI$_2$), preferably the general formula (XI$_2$') shown in Table 12.

TABLE 12

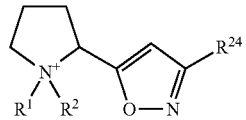

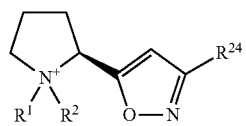

| $R^1$ | $R^2$ | $R^{24}$ |
|---|---|---|
| —CH$_3$ | — | —CH$_3$ |
| —CH$_3$ | —CH$_3$ | —CH$_3$ |
| —CH$_2$CH$_3$ | —CH$_3$ | —CH$_3$ |
| —CH$_2$CH$_3$ | —CH$_2$CH$_3$ | —CH$_3$ |

Particularly preferred examples of compounds of formula (XI), (XI'), (XI$_1$), (XI$_1$'), (XI$_2$), or (XI$_2$') include 3-methyl-5-[(2S)-1-methylpyrrolidin-2-yl]-1,2-oxazole (ABT-418), i.e., a compound of formula (XI'), wherein $R^1$ is —CH$_3$; $R^2$ is absent; and $R^{24}$ is —CH$_3$.

In one embodiment, the nAChR-agonist is 3-[(3E)-3-[(2,4-dimethoxyphenyl)methylidene]-5,6-dihydro-4H-pyridin-2-yl]pyridine (GTS-21) or an analogue thereof having the following formula (XII):

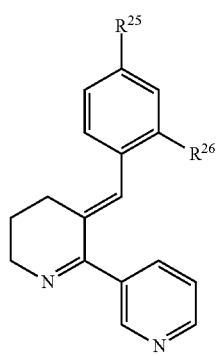

wherein $R^{25}$ and $R^{26}$ are each independently selected from alkyl, —OR$^{11}$, and —NR$^{12}$R$^{13}$, wherein $R^{12}$ and $R^{13}$ are each independently selected from the group consisting of H, alkyl, cycloalkyl, heterocyclyl, aryl, and heteroaryl, wherein each of the alkyl, cycloalkyl, heterocyclyl, aryl, and heteroaryl groups is optionally substituted (e.g., with one or more (in particular 1 to the maximum number of hydrogen atoms bound to the alkyl, cycloalkyl, heterocyclyl, aryl, or heteroaryl group, e.g., 1, 2, 3, 4, 5, 6, 7, 8, 9, or up to 10, such as between 1 to 5, 1 to 4, or 1 to 3, or 1 or 2) independently selected $R^{30}$ wherein $R^{30}$ is a 1$^{st}$ (or 2$^{nd}$ or 3$^{rd}$) level substituent as defined herein), and $R^{11}$ is selected from the group consisting from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, heteroaryl groups is optionally substituted (e.g., with one or more (in particular 1 to the maximum number of hydrogen atoms bound to the alkyl, alkenyl, alkynyl, cycloalkyl, heterocyclyl, aryl, or heteroaryl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a $1^{st}$ (or $2^{nd}$ or $3^{rd}$) level substituent as defined herein). In a preferred embodiment or formula (XII), the nAChR-agonist has the general formula (XII$_1$):

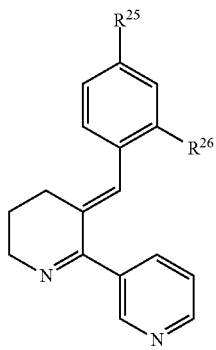

(XII$_1$)

wherein $R^{25}$ and $R^{26}$ are each independently selected from —O(C$_{1-3}$ alkyl) (e.g., —OCH$_3$ or —OCH$_2$CH$_3$), —NH (CH$_3$), —N(CH$_3$)$_2$, and —N$^+$(CH$_3$)$_3$. Preferred compounds of formula (XII) or (XII$_1$) are those having the general formula (XII$_2$) shown in Table 13.

TABLE 13

(XII$_2$)

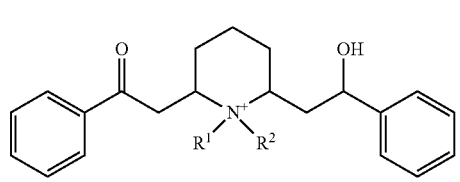

| $R^{25}$ | $R^{26}$ |
|---|---|
| —OCH$_3$ | —OCH$_3$ |
| —N$^+$(CH$_3$)$_3$ | —OCH$_3$ |
| —OCH$_3$ | —N$^+$(CH$_3$)$_3$ |

Particularly preferred examples of compounds of formula (XII), (XII$_1$), or (XII$_2$) include 3-[(3E)-3-[(2,4-dimethoxy-phenyl)methylidene]-5,6-dihydro-4H-pyridin-2-yl]pyridine (GTS-21), i.e., a compound of formula (XII), wherein $R^{25}$ and $R^{26}$ are both —OCH$_3$.

In one embodiment, the nAChR-agonist is lobeline or an analogue thereof having the following formula (XIII), preferably the general formula (XIII'):

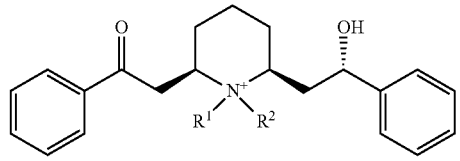

(XIII)

(XIII')

wherein at least one of $R^1$ and $R^2$ is present and $R^1$ and $R^2$ are each independently selected from the group consisting of absent, hydrogen, alkyl, and —Y'—Z', wherein Y' is —S (O)$_{1-2}$—, —S(O)$_{1-2}$O—, —C(=X')—, —C(=X')X'—, and —X'C(=X')—, wherein each X' is independently selected from O, S, and imino, and Z' is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl groups is optionally substituted (e.g., with one or more (in particular 1 to the maximum number of hydrogen atoms bound to the alkyl, alkenyl, alkynyl, cycloalkyl, heterocyclyl, aryl, or heteroaryl group, e.g., 1, 2, 3, 4, 5, 6, 7, 8, 9, or up to 10, such as between 1 to 5, 1 to 4, or 1 to 3, or 1 or 2) independently selected $R^{30}$, wherein $R^{30}$ is a $1^{st}$ (or $2^{nd}$ or $3^{rd}$) level substituent). If $R^1$ and $R^2$ are present, the compound of formula (XIII) contains a quaternary nitrogen atom. In this case, the corresponding counter anion may be any anion, preferably derived from a pharmaceutically acceptable acid as described herein. In a preferred embodiment of formula (XIII) (or formula (XIII')), the nAChR-agonist has the general formula (XIII), preferably the general formula (XIII$_1$'):

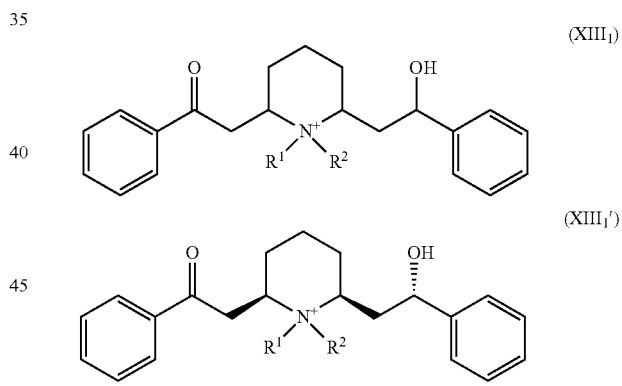

wherein $R^1$ and $R^2$ are independently selected from the group consisting of absent, hydrogen, and C$_{1-6}$ alkyl (e.g., C$_{1-3}$ alkyl such as methyl or ethyl). Preferred compounds of formula (XIII), (XIII'), (XIII$_1$), or (XIII$_1$') are those having the formula (XIII$_2$) or (XIII$_2$') shown in Table 14.

TABLE 14

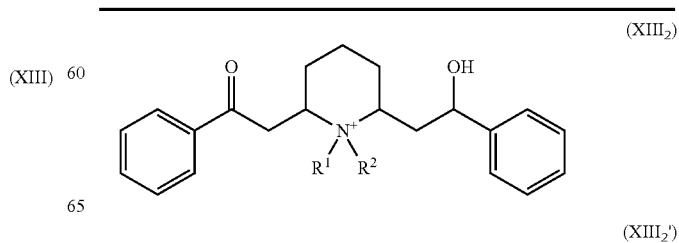

TABLE 14-continued

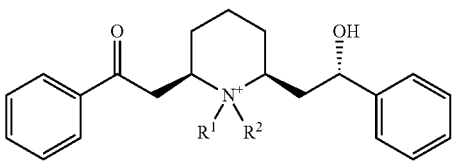

| R¹ | R² |
|---|---|
| H | — |
| —CH₃ | —CH₃ |
| —CH₂CH₃ | —CH₃ |
| —CH₂CH₃ | —CH₂CH₃ |

Particularly preferred examples of compounds of formula (XIII); (XIII'), (XIII$_1$), (XIII$_1$'), (XIII$_2$), or (XIII$_2$') include lobeline, i.e., a compound of formula (XIII$_2$'), wherein R¹ is H and R² is absent.

Particularly preferred nAChR-agonists suitable for the present invention are selected from the group consisting of a dimethylphenylpiperazinium (DMPP) salt, cytisine, 4-(trifluoromethyl)-10-azatricyclo[6.3.1.0²,⁷]dodeca-2,4,6-triene (CP-601932), varenicline, nicotine, 6-[5-fluoro-2-(pyridin-3-yl)phenoxy]-3-azabicyclo[3.2.1]octane (PF-4575180), epibatidine, acetylcholine, N-methylcarbamylcholine, 3-methyl-5-[(2S)-1-methylpyrrolidin-2-yl]-1,2-oxazole (ABT-418), 3-[(3E)-3-[(2,4-dimethoxyphenyl)methylidene]-5,6-dihydro-4H-pyridin-2-yl]pyridine (GTS-21), lobeline, and 4-{[2-(1-methyl-2-pyrrolidinyl)ethyl]thio}phenol (SIB-1553A, e.g. as hydrochloride salt), such as a compound selected from the group consisting of a DMPP salt, cytisine, and nicotine, in particular a DMPP salt.

Examples of suitable nAChR-agonists include those which are $\alpha_1\beta_1\delta\epsilon$ agonists, $\alpha_1\beta_1\delta\gamma$ agonists, $\alpha_3\beta_4$ agonists, $\alpha_4\beta_2$ agonists or $\alpha_7$ agonists (preferably, $\alpha_3\beta_4$ agonists, $\alpha_4\beta_2$ agonists or $\alpha_7$ agonists) of the nicotinic acetylcholine receptor. In one embodiment, the nAChR-agonists used according to the present invention are selective for the $\alpha_3\beta_4$ and/or $\alpha_4\beta_2$ subtype of the nicotinic acetylcholine receptor.

It is intended that the nAChR-agonists used according to the present invention (in particular, the nAChR-agonists of any one of formulas (IV), (IV$_1$), (IV$_2$), (V), (V'), (V$_1$), (V$_1$'), (V$_2$), (V$_2$'), (VI), (VI'), (VI$_1$), (VI$_1$'), (VI$_2$), (VI$_2$'), (VII), (VII$_1$), (VII$_2$), (VIII), (VIII'), (VIII$_1$), (VIII$_1$'), (VIII$_2$), (VIII$_2$'), (IX), (IX¹), (IX$_1$), (IX$_1$'), (IX$_2$), (IX$_2$'), (X), (X$_1$), (XI), (XI'), (XI$_1$), (XI$_1$'), (XI$_2$), (XI$_2$'), (XII), (XII$_1$), (XII$_2$), (XIII), (XIII'), (XIII$_1$), (XIII$_1$'), (XIII$_2$), and (XIII$_2$') such as those depicted in Tables 5, 6, 7, 8, 9, 10, 11, 12, 13, and 14, above) encompass not only the compounds as depicted but also their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof.

The nAChR-agonists used according to the present invention (in particular, the nAChR-agonists of any one of formulas (IV), (IV$_1$), (IV$_2$), (V), (V'), (V$_1$), (V$_1$'), (V$_2$), (V$_2$'), (VI), (VI'), (VII), (VI$_1$'), (VI$_2$), (VI$_2$'), (VII), (VII), (VII$_2$), (VIII), (VIII'), (VIII), (VIII'), (VIII$_2$), (VIII$_2$'), (IX), (IX¹), (IX$_1$), (IX$_1$'), (IX$_2$), (IX$_2$'), (X), (X$_1$), (XI), (XI'), (XI$_1$), (XI$_1$'), (XI$_2$), (XI$_2$'), (XII), (XII$_1$), (XII$_2$), (XIII), (XIII'), (XIII$_1$), (XIII$_1$'), (XIII$_2$), and (XIII$_2$') such as those depicted in Tables 5, 6, 7, 8, 9, 10, 11, 12, 13, and 14, above) which contain a basic functionality may form salts with a variety of inorganic or organic acids. The nAChR-agonists used according to the present invention (in particular, the nAChR-agonists of any one of formulas (IV), (IV$_1$), (IV$_2$), (V), (V'), (V$_1$), (V$_1$'), (V$_2$), (V$_2$'), (VI), (VI'), (VI$_1$), (VI$_1$'), (VI$_2$), (VI$_2$'), (VII), (VII$_1$), (VII$_2$), (VIII), (VIII'), (VIII), (VIII'), (VIII$_2$), (VIII$_2$'), (IX), (IX'), (IX$_1$), (IX$_1$'), (IX$_2$), (IX$_2$'), (X), (X$_1$), (XI), (XI'), (XI$_1$), (XI$_1$'), (XI$_2$), (XI$_2$'), (XII), (XII$_1$), (XII$_2$), (XIII), (XIII'), (XIII$_1$), (XIII$_1$'), (XIII$_2$), and (XIII$_2$') such as those depicted in Tables 5, 6, 7, 8, 9, 10, 11, 12, 13, and 14, above) which contain an acidic functionality may form salts with a variety of inorganic or organic bases. Exemplary inorganic and organic acids/bases as well as exemplary acid/base addition salts of the nAChR-agonists used according to the present invention are given in the definition of "pharmaceutically acceptable salt" in the section "Pharmaceutical composition", below. The nAChR-agonists used according to the present invention (in particular, the nAChR-agonists of any one of formulas (IV), (IV$_1$), (IV$_2$), (V), (V'), (V$_1$), (V$_1$'), (V$_2$), (V$_2$'), (VI), (VI'), (VI$_1$), (VI$_1$'), (VI$_2$), (VI$_2$'), (VII), (VII), (VII$_2$), (VIII), (VIII'), (VIII), (VIII'), (VIII$_2$), (VIII$_2$'), (IX), (IX'), (IX$_1$), (IX$_1$'), (IX$_2$), (IX$_2$'), (X), (X$_1$), (XI), (XI'), (XI$_1$), (XI$_1$'), (XI$_2$), (XI$_2$'), (XII), (XII$_1$), (XII$_2$), (XIII), (XIII'), (XIII$_1$), (XIII$_1$'), (XIII$_2$), and (XIII$_2$') such as those depicted in Tables 5, 6, 7, 8, 9, 10, 11, 12, 13, and 14, above) which contain both basic and acidic functionalities may be converted into either base or acid addition salt. The neutral forms of the nAChR-agonists used according to the present invention (in particular, the nAChR-agonists of any one of formulas (IV), (IV$_1$), (IV$_2$), (V), (V'), (V$_1$), (V$_1$'), (V$_2$), (V$_2$'), (VI), (VI'), (VI$_1$), (VI$_1$'), (VI$_2$), (VI$_2$'), (VII), (VII), (VII$_2$), (VIII), (VIII'), (VIII), (VIII'), (VIII$_2$), (VIII$_2$'), (IX), (IX'), (IX$_1$), (IX$_1$'), (IX$_2$), (IX$_2$'), (X), (X$_1$), (XI), (XI'), (XI$_1$), (XI$_1$'), (XI$_2$), (XI$_2$'), (XII), (XII$_1$), (XII$_2$), (XIII), (XIII'), (XIII$_1$), (XIII$_1$'), (XIII$_2$), and (XIII$_2$') such as those depicted in Tables 5, 6, 7, 8, 9, 10, 11, 12, 13, and 14, above) may be regenerated by contacting the salt with a base or acid and isolating the parent compound in the conventional manner.

The nAChR-agonists used according to the present invention (in particular, the nAChR-agonists of any one of formulas (IV), (IV$_1$), (IV$_2$), (V), (V'), (V$_1$), (V$_1$'), (V$_2$), (V$_2$'), (VI), (VI'), (VI$_1$), (VI$_1$'), (VI$_2$), (VI$_2$'), (VII), (VII$_1$), (VII$_2$), (VIII), (VIII'), (VIII$_1$), (VIII$_1$'), (VIII$_2$), (VIII$_2$'), (IX), (IX'), (IX$_1$), (IX¹'), (IX$_2$), (IX$_2$'), (X), (X$_1$), (XI), (XI'), (XI$_1$), (XI$_1$'), (XI$_2$), (XI$_2$'), (XII), (XII$_1$), (XII$_2$), (XIII), (XIII'), (XIII$_1$), (XIII$_1$'), (XIII$_2$), and (XIII$_2$') such as those depicted in Tables 5, 6, 7, 8, 9, 10, 11, 12, 13, and 14, above) may be in a prodrug form. Prodrugs of the nAChR-agonists used according to the present invention are those compounds that upon administration to an individual undergo chemical conversion under physiological conditions to provide the nAChR-agonists used according to the present invention (in particular, the nAChR-agonists of any one of formulas (IV), (IV$_1$), (IV$_2$), (V), (V'), (V$_1$), (V$_1$'), (V$_2$), (V$_2$'), (VI), (VI'), (VI$_1$), (VI$_1$'), (VI$_2$), (VI$_2$'), (VII), (VII$_1$), (VII$_2$), (VIII), (VIII'), (VIII$_1$), (VIII$_1$'), (VIII$_2$), (VIII$_2$'), (IX), (IX'), (IX$_1$), (IX$_1$'), (IX$_2$), (IX$_2$'), (X), (X$_1$), (XI), (XI'), (XI$_1$), (XI$_1$'), (XI$_2$), (XI$_2$'), (XII), (XII$_1$), (XII$_2$), (XIII), (XIII'), (XIII$_1$), (XIII$_1$'), (XIII$_2$), and (XIII$_2$') such as those depicted in Tables 5, 6, 7, 8, 9, 10, 11, 12, 13, and 14, above). Additionally, prodrugs can be converted to the nAChR-agonists used according to the present invention (in particular, the nAChR-agonists of any one of formulas (IV), (IV$_1$), (IV$_2$), (V), (V'), (V$_1$), (V$_1$'), (V$_2$), (V$_2$'), (VI), (VI'), (VI$_1$), (VI$_1$'), (VI$_2$), (VI$_2$'), (VII), (VII$_1$), (VII$_2$), (VIII), (VIII'), (VIII$_1$), (VIII$_1$'), (VIII$_2$), (VIII$_2$'), (IX), (IX'), (IX$_1$), (IX$_1$'), (IX$_2$), (IX$_2$'), (X), (X$_1$), (XI), (XI'), (XI$_1$), (XI$_1$'), (XI$_2$), (XI$_2$'), (XII), (XII$_1$), (XII$_2$), (XIII), (XIII'), (XIII$_1$), (XIII$_1$'), (XIII$_2$), and (XIII$_2$') such as those depicted in Tables 5, 6, 7, 8, 9, 10, 11, 12, 13, and 14, above) by chemical or biochemical methods in an ex vivo environment. For example, prodrugs can be slowly converted to the nAChR-agonists used according to the present invention (in particular, the 35 nAChR-agonists of any one of formulas (IV), (IV$_1$), (IV$_2$), (V), (V'), (V$_1$), (V$_1$'), (V$_2$), (V$_2$'), (VI), (VI'), (VI$_1$), (VI$_1$'), (VI$_2$), (VI$_2$'), (VII), (VII$_1$), (VII$_2$), (VIII), (VIII'), (VIII$_1$), (VIII$_1$'), (VIII$_2$), (VIII$_2$'), (IX), (IX'), (IX$_1$), (IX$_1$'), (IX$_2$), (IX$_2$'), (X), (XI), (XI), (XI'), (XI$_1$), (XI$_1$'), (XI$_2$), (XI$_2$'), (XII), (XII$_1$), (XII$_2$), (XIII), (XIII'), (XIII$_1$), (XIII'), (XIII$_2$), and (XIII$_2$') such as those depicted in Tables 5, 6, 7, 8, 9, 10, 11, 12, 13, and 14, above) when, for example, placed in a transdermal patch reservoir with a suitable enzyme or chemical reagent. Exemplary prodrugs are esters or amides which are hydrolyzable in vivo.

The nAChR-agonists used according to the present invention (in particular, the nAChR-agonists of any one of formulas (IV), (IV$_1$), (IV$_2$), (V), (V'), (V$_1$), (V$_1$'), (V$_2$), (V$_2$'), (VI), (VI'), (VI$_1$), (VI$_1$'), (VI$_2$), (VI$_2$'), (VII), (VII), (VII$_2$), (VIII), (VIII'), (VIII$_1$), (VIII$_1$'), (VIII$_2$), (VIII$_2$'), (IX), (IX'), (IX$_1$), (IX$_1$'), (IX$_2$), (IX$_2$'), (X), (XI), (XI), (XI'), (XI$_1$), (XI$_1$'), (XI$_2$), (XI$_2$'), (XII), (XII$_1$), (XII$_2$), (XIII), (XIII'), (XIII$_1$), (XIII'), (XIII$_2$), and (XIII$_2$') such as those depicted in Tables 5, 6, 7, 8, 9, 10, 11, 12, 13, and 14, above) can be prepared as described in the literature (cf., e.g., WO 2011/080751, WO 2007/100430, WO 2005/117860, WO 03/037329, and Lowe III et al. (Bioorg. Med. Chem. Ltt. 20 (2010), 4749-4752), Chatterjee et al. (Neuropsychopharmacology 36 (2011), 603-615)) or prepared by methods analogous thereto, which are readily known and available to one of ordinary skill in the art of organic synthesis.

Without being bound to any theory, it is believed that in general, nAChR-agonists act on nicotinic acetylcholine receptors in areas of the brain which control the food intake. Thus, by activating these areas utilizing nAChR-agonists it is believed that the food intake decreases; cf. FIG. 1.

Conjugates of a Agonist of TRPM8 (TRPM8-Agonist) and an Agonist of the Nicotinic Acetylcholine Receptor (nAChR-Agonist)

Another aspect of the present invention is a conjugate consisting of an agonist of TRPM8 (TRPM8-agonist) and an agonist of the nicotinic acetylcholine receptor (nAChR-agonist) connected by a linker. The agonist of TRPM8 (TRPM8-agonist) and an agonist of the nicotinic acetylcholine receptor (nAChR-agonist) can be connected by any suitable linker known in the art. It is also understood that the linker depends on the nature of the molecules to be linked together and that the TRPM8-agonist and/or the nAChR-agonist prior the attachment to the linker moiety might be modified, i.e. by introduction of a chemical group like a hydroxyl-group, in order to allow an attachment to the linker. It is also understood by that such modification is carried out in a manner, that the TRPM8-agonist and/or the nAChR-agonist retains the biological activity. The TRPM8-against can be any one of formulas (I), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie'), (Ie$_1$), (Ie'), (Ie$_2$), (Ie$_2$'), (IIa), (IIb), (IIa$_1$), (IIb$_1$), (IIa$_2$), (IIb$_2$), (III), (III$_1$), (III$_2$), such as those depicted in Tables 1a, 1b, 1c, 1d, 1e, 2, 3, and 4, above). The nAChR-agonist can be any one of formulas (IV), (IV$_1$), (IV$_2$), (V), (V'), (V$_1$), (V$_1$'), (V$_2$), (V$_2$'), (VI), (VI'), (VI$_1$), (VI$_1$'), (VI$_2$), (VI$_2$'), (VII), (VII$_1$), (VII$_2$), (VIII), (VIII'), (VIII$_1$'), (VIII$_2$), (VIII$_2$'), (IX), (IX'), (IX$_1$), (IX$_1$'), (IX$_2$), (IX$_2$'), (X), (XI), (XI), (XI'), (XI), (XI'), (XI$_2$), (XI$_2$'), (XII), (XII$_1$), (XII$_2$), (XIII), (XIII'), (XIII$_1$), (XIII'), (XIII$_2$), and (XIII$_2$') such as those depicted in Tables 5, 6, 7, 8, 9, 10, 11, 12, 13, and 14, above).

The term "conjugate" or "TRPM8-agonist-nAChR-agonist conjugate" as used herein in general refers to the linkage of an agonist of TRPM8 (TRPM8-agonist) with an agonist of the nicotinic acetylcholine receptor (nAChR-agonist). The linkage can be covalent bonds. Various linkers, known in the art and described herein, can be employed in order to form the TRPM8-agonist-nAChR-agonist conjugate.

An TRPM8-agonist-nAChR-agonist conjugate as is preferred herein has the formula T-(L-(A)x)y, ((T)v-L)w-(A)x or ((T)v-L)w-(L-(A)x)y. "T" stands for an TRPM8-agonist according to any one of formulas (I), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie'), (Ie$_1$), (Ie$_1$'), (Ie$_2$), (Ie$_2$'), (IIa), (IIb), (IIa$_1$), (IIb$_1$), (IIa$_2$), (IIb$_2$), (III), (III$_1$), (III$_2$), such as those depicted in Tables 1a, 1b, 1c, 1d, 1e, 2, 3, and 4, above), "L" stands for a linker and "A" stands for an nAChR-agonist according to any one of formulas (IV), (IV$_1$), (IV$_2$), (V), (V'), (V$_1$), (V$_1$'), (V$_2$), (V$_2$'), (VI), (VI'), (VI$_1$), (VI$_1$'), (VI$_2$), (VI$_2$'), (VII), (VII$_1$), (VII$_2$), (VIII), (VIII'), (VIII), (VIII'), (VIII$_2$), (VIII$_2$'), (IX), (IX$^1$), (IX$_1$), (IX$_1$'), (IX$_2$), (IX$_2$'), (X), (X$_1$), (XI), (XI'), (XI), (XI'), (XI$_2$), (XI$_2$'), (XII), (XII), (XII$_2$), (XIII), (XIII'), (XIII), (XIII'), (XIII$_2$), and (XIII$_2$') such as those depicted in Tables 5, 6, 7, 8, 9, 10, 11, 12, 13, and 14, above). "v" may be an integer from 1 to 10. "w" may be an integer from 1 to 10. "x" may be an integer from 1 to 10. "y" may be an integer from 1 to 10. Accordingly, v may be 1, 2, 3, 4, 5, 6, 7, 8, 9 or 10. Accordingly, w may be 1, 2, 3, 4, 5, 6, 7, 8, 9 or 10. Accordingly, x may be 1, 2, 3, 4, 5, 6, 7, 8, 9 or 10. Accordingly, y may be 1, 2, 3, 4, 5, 6, 7, 8, 9 or 10. As purely illustrative examples, v, w, x or y may be an integer from 1 to 8, from 1 to 6, from 1 to 4, or from 1 to 2.

While the TRPM8-agonist to nAChR-agonist ratio has an exact integer value for a specific conjugate molecule (e.g., y multiplied by x in the formula T-(L-(A)x)y), it is understood that the value will often be an average value when used to describe a sample containing many molecules, due to some degree of inhomogeneity, typically associated with the conjugation step.

In accordance with the present disclosure, the TRPM8-agonist may be linked, via covalent attachment by a linker, to the nAChR-agonist. As used herein, a "linker" is any chemical moiety that is capable of linking a TRPM8-agonist to a nAChR-agonist. Accordingly, the nAChR-agonist can be linked to the TRPM8-agonist through a linker L. L is any chemical moiety that is capable of linking the TRPM8-agonist to the nAChR-agonist. Preferably, the linker L attaches the TRPM8-agonist to the nAChR-agonist through covalent bond(s). The linker reagent is a bifunctional or multifunctional moiety which can be used to link a nAChR-agonist and a TRPM8-agonist to form TRPM8-agonist-nAChR-agonist conjugates. TRPM8-agonist-nAChR-agonist conjugates can be prepared using a linker having a reactive functionality for binding to the nAChR-agonist and to the TRPM8-agonist. Alternatively the nAChR-agonist and to the TRPM8-agonist might be modified to contain a reactive functionality. A side chain or suitable moiety of the TRPM8-agonist can form a bond with a functional group of a linker reagent. These side chains and suitable moieties can be introduced to either the TRPM8 or nAChR-agonist in multiple positions relative to the native molecule. Structure activity relationship studies previously conducted have demonstrated that reactive functional groups can be placed in several positions on the TRPM8 or nACHR-agonists without affecting the native functionality of these molecules. Thus, alternative functional group locations can participate in crosslinking these two molecules with a linker reagent. The terms "linker reagent", "cross-linking reagent", "linker derived from a cross-linking reagent" and "linker" may be used interchangeably throughout the present disclosure.

Linkers can be susceptible to cleavage (cleavable linker), such as, acid-induced cleavage, photo-induced cleavage, peptidase-induced cleavage, esterase-induced cleavage, and disulfide bond cleavage, at conditions under which the nAChR-agonist and/or the TRPM8-agonist remains active. Alternatively, linkers can be substantially resistant to cleavage (e.g., stable linker or non-cleavable linker). In some aspects, the linker may be a procharged linker, a hydrophilic linker, or a dicarboxylic acid based linker. Accordingly, in some embodiments of any one of the TRPM8-agonist-nAChR-agonist conjugates disclosed herein the linker (L) is selected from the group consisting of a cleavable linker, a non-cleavable linker, a hydrophilic linker, a procharged linker and a dicarboxylic acid based linker. In some embodiments, L is a cleavable linker. In some embodiments, L is a non-cleavable linker. In some embodiments, L is an acid-labile linker, photo-labile linker, peptidase cleavable linker, esterase cleavable linker, a disulfide bond reducible linker, a hydrophilic linker, a procharged linker, or a dicarboxylic acid based linker.

Non-cleavable linkers are any chemical moiety capable of linking a nAChR-agonist to a TRPM8-agonist in a stable, covalent manner and does not fall off under the categories listed above for cleavable linkers. Thus, non-cleavable linkers are substantially resistant to acid-induced cleavage, photo-induced cleavage, peptidase-induced cleavage, esterase-induced cleavage and disulfide bond cleavage. Furthermore, non-cleavable refers to the ability of the chemical bond in the linker or adjoining to the linker to withstand cleavage induced by an acid, photolabile-cleaving agent, a peptidase, an esterase, or a chemical or physiological compound that cleaves a disulfide bond, at conditions under which the TRPM8-agonist or the nAChR-agonist does not lose its activity.

Acid-labile linkers are linkers cleavable at acidic pH. For example, certain intracellular compartments, such as endosomes and lysosomes, have an acidic pH (pH 4-5), and provide conditions suitable to cleave acid-labile linkers.

Photo-labile linkers are linkers that are useful at the body surface and in many body cavities that are accessible to light. Furthermore, infrared light can penetrate tissue.

Some linkers can be cleaved by peptidases, i.e. peptidase cleavable linkers. In this regard, certain peptides are readily cleaved inside or outside cells, see e.g. Trout et al., 79 Proc. Natl. Acad. Sci. USA, 626-629 (1982) and Umemoto et al. 43 Int. J. Cancer, 677-684 (1989). Peptides are composed of α-amino acids and peptidic bonds, which chemically are amide bonds between the carboxylate of one amino acid and the amino group of a second amino acid.

Some linkers can be cleaved by esterases, i.e. esterase cleavable linkers. In this regard, certain esters can be cleaved by esterases present inside or outside of cells. Esters are formed by the condensation of a carboxylic acid and an alcohol.

Procharged linkers are derived from charged cross-linking reagents that retain their charge after incorporation into an antibody drug conjugate. Examples of procharged linkers can be found in US 2009/0274713.

Suitable cross-linking reagents that form a non-cleavable linker between the nAChR-agonist and the TRPM8-agonist are those well known in the art for antibody drug-conjugate formation, and can form non-cleavable linkers that comprise a sulfur atom (such as SMCC) or those that are without a sulfur atom. Preferred cross-linking reagents that form non-cleavable linkers between the nAChR-agonist, and the TRPM8-agonist comprise a maleimido- or haloacetyl-based moiety. According to the present disclosure, such non-cleavable linkers are said to be derived from maleimido- or haloacetyl-based moieties.

Cross-linking reagents comprising a maleimido-based moiety include but are not limited to, N-succinimidyl-4-(maleimidomethyl)cyclohexane-1-carboxylate (SMCC), sulfosuccinimidyl 4-(N-maleimidomethyl)cyclohexane-1-carboxylate (sulfo-SMCC), N-succinimidyl-4-(maleimidomethyl)cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-succinimidyl ester (EMCS), m-maleimidobenzoyl-N-hydroxysuccinimide ester (MBS), N-(α-maleimidoacetoxy)-succinimide ester (AMSA), succinimidyl-6-(β-maleimidopropionamido) hexanoate (SMPH), N-succinimidyl-4-(p-maleimidophenyl)-butyrate (SMPB), N-(-p-maleomidophenyl)isocyanate (PMIP) and maleimido-based cross-linking reagents containing a polyethythene glycol spacer, such as maleimide-PEG-NHS, which is denoted herein also as MAL-PEG-NHS. These cross-linking reagents form non-cleavable linkers derived from maleimido-based moieties. Representative structures of maleimido-based cross-linking reagents are shown below.

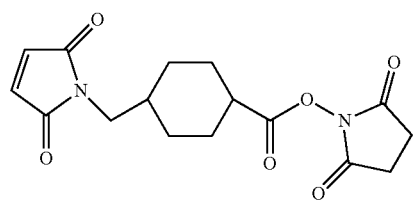

SMCC

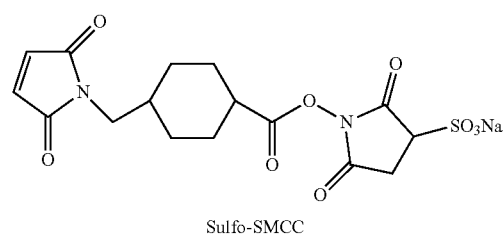

Sulfo-SMCC

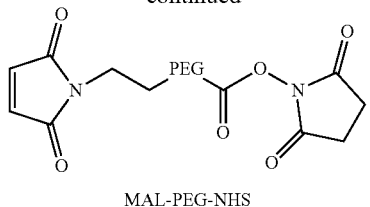

MAL-PEG-NHS

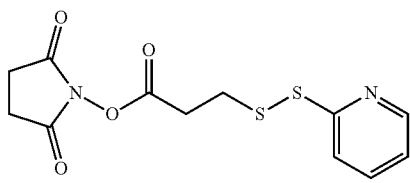

N-succinimidyl-3-(2-pyridyldithio)propionate (SPDP),

In some embodiments, the linker L is derived from N-succinimidyl-4-(maleimidomethyl)cyclohexanecarboxylate (SMCC), sulfosuccinimidyl 4-(N-maleimidomethyl)cyclohexane-1-carboxylate (sulfo-SMCC) or MAL-PEG-NHS.

Cross-linking reagents comprising a haloacetyl-based moiety include N-succinimidyl iodoacetate (SIA), N-succinimidyl(4-iodoacetyl)aminobenzoate (SIAB), N-succinimidyl bromoacetate (SBA) and N-succinimidyl 3-(bromoacetamido)propionate (SBAP). These cross-linking reagents form a non-cleavable linker derived from haloacetyl-based moieties. Representative structures of haloacetyl-based cross-linking reagents are shown below.

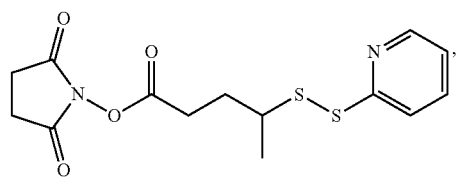

N-succinimidyl-4-(2-pyridyldithio)pentanoate (SPP)

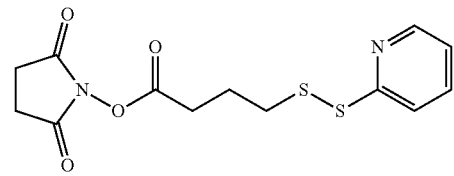

N-succinimidyl-4-(2-pyridyldithio)butanoate (SPDB)

In some embodiments the linker L is derived from N-succinimidyl iodoacetate (SIA) or N-succinimidyl(4-iodoacetyl)aminobenzoate (SIAB).

Suitable cross-linking reagents that form a cleavable linker are well known in the art. Disulfide containing linkers are linkers cleavable through disulfide exchange, which can occur under physiological conditions. According to the present disclosure, such cleavable linkers are said to be derived from disulfide-based moieties. Suitable disulfide cross-linking reagents include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB) and N-succinimidyl-4-(2-pyridyldithio)2-sulfo-butanoate (sulfo-SPDB), the structures of which are shown below. These disulfide cross-linking reagents form a cleavable linker derived from disulfide-based moieties.

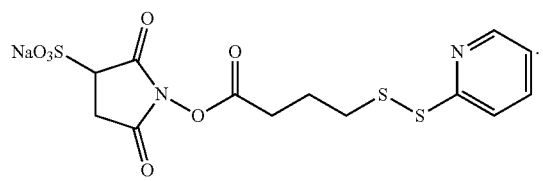

N-succinimidyl-4-(2-pyridyldithio)2-sulfo-butanoate (sulfo-SPDB)

In some embodiments, the linker L is derived from N-succinimidyl-4-(2-pyridyldithio)butanoate), (SPDB)

Suitable cross-linking reagents that form a charged linker are known as procharged cross-linking reagents. In an embodiment, the linker L is derived from the procharged cross-linking reagent which is CX1-1. The structure of CX1-1 is shown below:

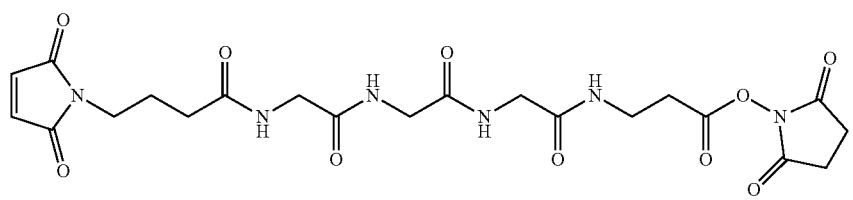

2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1)

Further linkers which may be suitably used are maleimidocaproyl (MC), maleimidocaproyl (MC) with a self-cleaving peptide, maleimidodiaminopropionyl (mDPR) with a self-cleaving peptide, and 4-(N-maleimidomethyl)-cyclohexane-1-carbonyl (MCC).

In some embodiments the TRPM8-agonist is connected by a linker to another TRPM8-agonist. In some embodiments the nAChR-agonist is connected by a linker to another nAChR-agonist. In some embodiments the TRPM8-agonist is icilin. In some embodiments the TRPM8-agonist is N-(4-methoxyphenyl)-5-methyl-2-(1-methylethyl)cyclohexanecarboxamide (also designated as WS-12). In some embodiments the nAChR-agonist is dimethylphenylpiperazinium (DMPP). In a preferred embodiment icilin is connected to dimethylphenylpiperazinium (DMPP) by a linker. In another preferred embodiment N-(4-methoxyphenyl)-5-methyl-2-(1-methylethyl)cyclohexanecarboxamide (also designated as WS-12) is connected to dimethylphenylpiperazinium (DMPP) by a linker.

Composition Comprising a TRPM8-Agonist and an nAChR-Agonists

As demonstrated in the present application, the combined action of a TRPM8-agonist and an nAChR-agonist results in synergistric effects. In particular, a combination of a TRPM8-agonist and an nAChR-agonist leads to (i) an synergistically increase of weight loss (i.e., greater weight loss in less time compared to each monotherapy or control), (ii) better glucose tolerance (i.e., faster restoration of normal blood glucose level compared to monotherapy with icilin or control), (iii) higher insulin sensitivity (i.e., less insulin is required to achieve a faster restoration of normal blood glucose level compared to each monotherapy or control), and (iv) better reduction in hepatic lipid accumulation compared to each monotherapy or control. Thus, it has been shown that the combination of an nAChR-agonist with a TRPM8-agonist improves multiple aspects of glucose and lipid metabolism and, therefore, is suitable to inhibit weight gain (e.g., weight gain following smoking cessation or for reducing weight), treat obesity, and/or treat obesity-related disorders (such as metabolic syndrome).

In certain embodiments, the composition of the present invention comprising a TRPM8-agonist and an nAChR-agonist exhibits pharmacological properties (effectiveness against obesity; effectiveness against obesity-related disorders; effectiveness for inhibition of weight gain (e.g., weight gain following smoking cessation or for reducing weight); toxicity; bioavailability; side effects; dosing; patient compliance; compatibility; stability; half-life; etc.), which are in at least one aspect superior to the pharmacological properties exhibited by one or more of known anti-obesity drugs such as orlistat, sibutramine, and liraglutide.

In one embodiment, the composition of the present invention may further comprise an additional active compound (which is not a TRMP8-agonist as specified herein and not an nAChR-agonist as specified herein). Such an additional active compound may be selected from any compound which can be used for inhibiting weight gain (e.g., weight gain following smoking cessation or for reducing weight) and/or for treating obesity and/or obesity-related disorders. Exemplary additional active compounds in this respect include anti-obesity drugs which reduce appetite and/or decrease fat absorption.

In a preferred embodiment, the composition of the present invention is a pharmaceutical composition, in particular a pharmaceutical composition as specified below.

Pharmaceutical Compositions

The TRMP8-agonists used according to the present invention (in particular, the TRMP8-agonists of any one of formulas (I), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie'), (Ie$_1$), (Ie$_1$'), (Ie$_2$), (Ie$_2$'), (IIa), (Ib), (IIa$_1$), (IIb$_1$), (IIa$_2$), (IIb$_2$), (III), (III$_1$), (III$_2$), such as those depicted in Tables 1a, 1b, 1c, 1d, 1e, 2, 3, and 4, above) as well as the nAChR-agonists used according to the present invention (in particular, the nAChR-agonists of any one of formulas (IV), (IV$_1$), (IV$_2$), (V), (V'), (V$_1$), (V$_1$'), (V$_2$), (V$_2$'), (VI), (VI'), (VI$_1$), (VI$_1$'), (VI$_2$), (VI$_2$'), (VII), (VII$_1$), (VII$_2$), (VIII), (VIII'), (VIII$_1$), (VIII$_1$'), (VIII$_2$), (VIII$_2$'), (IX), (IX'), (IX$_1$), (IX$_1$'), (IX$_2$), (IX$_2$'), (X), (X$_1$), (XI), (XI'), (XI$_1$), (XI$_1$'), (XI$_2$), (XI$_2$'), (XII), (XII$_1$), (XII$_2$), (XIII), (XIII'), (XIII$_1$), (XIII$_1$'), (XIII$_2$), and (XIII$_2$') such as those depicted in Tables 5, 6, 7, 8, 9, 10, 11, 12, 13, and 14, above) are preferably administered to a patient in need thereof via a pharmaceutical composition. In one embodiment, the pharmaceutical composition comprises (i) a TRMP8-agonist as described above (e.g. having the general formula (I), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie'), (Ie$_1$), (Ie$_1$'), (Ie$_2$), (Ie$_2$'), (IIa), (IIb), (IIa$_1$), (IIb$_1$), (IIa$_2$), (IIb$_2$), (III), (III$_1$), (III$_2$), such as those depicted in Tables 1a, 1b, 1c, 1d, 1e, 2, 3, and 4, above, or a hydrate, solvate, salt, complex, racemic mixture, diastereomer, enantiomer, or tautomer thereof or an isotopically enriched form of any of the foregoing), (ii) an nAChR-agonist as described above (e.g. having the general formula (IV), (IV$_1$), (IV$_2$), (V), (V'), (VI), (V'), (V$_2$), (V$_2$'), (VI), (VI'), (VI$_1$), (VI$_1$'), (VI$_2$), (VI$_2$'), (VII), (VII$_1$), (VII$_2$), (VIII), (VIII'), (VIII$_1$), (VIII$_1$'), (VIII$_2$), (VIII$_2$'), (IX), (IX'), (IX$_1$), (IX$_1$'), (IX$_2$), (IX$_2$'), (X), (XI), (XI), (XI'), (XI$_1$), (XI$_1$'), (XI$_2$), (XI$_2$'), (XII), (XII$_1$), (XII$_2$), (XIII), (XIII'), (XIII$_1$), (XIII$_1$'), (XIII$_2$), and (XIII$_2$') such as those depicted in Tables 5, 6, 7, 8, 9, 10, 11, 12, 13, and 14, above, or a hydrate, solvate, salt, complex, racemic mixture, diastereomer, enantiomer, or tautomer thereof or an isotopically enriched form of any of the foregoing); and (iii) one or more pharmaceutically acceptable excipients. In one embodiment, the pharmaceutical composition is a kit comprising (1) a first container including the TRPM8-agonist and (2) a second container including the nAChR-agonist, wherein the one or more pharmaceutically acceptable excipients may be present in one or both of first and second containers or may be present in one or more additional containers.

The pharmaceutical composition may be administered to an individual by any route, such as enterally or parenterally.

The expressions "enteral administration" and "administered enterally" as used herein mean that the drug administered is taken up by the stomach and/or the intestine. Examples of enteral administration include oral and rectal administration. The expressions "parenteral administration" and "administered parenterally" as used herein mean modes of administration other than enteral administration, usually by injection or topical application, and include, without limitation, intravenous, intramuscular, intraarterial, intrathecal, intracapsular, intraosseous, intraorbital, intracardiac, intradermal, intraperitoneal, transtracheal, subcutaneous, subcuticular, intraarticular, subcapsular, intracerebral, intracerebroventricular, subarachnoid, intraspinal, epidural and intrasternal administration (such as by injection and/or infusion) as well as topical administration (e.g., epicutaneous, inhalational, or through mucous membranes (such as buccal, sublingual or vaginal)).

The compounds used according to the present invention are generally applied in "pharmaceutically acceptable amounts" and in "pharmaceutically acceptable preparations". Such compositions may contain salts, buffers, preserving agents, carriers and optionally other therapeutic agents. "Pharmaceutically acceptable salts" comprise, for example, acid addition salts which may, for example, be formed by mixing a solution of compounds with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, arginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, galactate, galacturonate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isobutyrate, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, phthalate, picrate, pivalate, polygalacturonate, propionate, salicylate, stearate, sulfate, suberate, succinate, tannate, tartrate, teoclate, tosylate, triethiodide, undecanoate, valerate, and the like (see, for example, Berge et al., "Pharmaceutical Salts", *J. Pharm. Sci.*, 66, pp. 1-19 (1977)).

The term "excipient" when used herein is intended to indicate all substances in a pharmaceutical composition which are not active ingredients (e.g., which are therapeutically inactive ingredients that do not exhibit any therapeutic effect in the amount/concentration used), such as, e.g., carriers, binders, lubricants, thickeners, surface active agents, preservatives, emulsifiers, buffers, flavoring agents, colorants, or antioxidants.

The compositions described in the present invention may comprise a pharmaceutically acceptable carrier. As used herein, "pharmaceutically acceptable carrier" includes any and all solvents, dispersion media, coatings, isotonic and absorption delaying agents, and the like that are physiologically compatible. The "pharmaceutically acceptable carrier" may be in the form of a solid, semisolid, liquid, or combinations thereof. Preferably, the carrier is suitable for enteral (such as oral) or parenteral administration (such as intravenous, intramuscular, subcutaneous, spinal or epidermal administration (e.g., by injection or infusion)). Depending on the route of administration, the active compound, i.e., the compound used in the present invention, either alone or in combination with one or more additional active compounds, may be coated in a material to protect the active compound(s) from the action of acids and other natural conditions that may inactivate the active compound.

Examples of suitable aqueous and non-aqueous carriers which may be employed in the pharmaceutical compositions according to the present invention include water (e.g., water for injection), ethanol, polyols (such as glycerol, propylene glycol, polyethylene glycol, and the like), aqueous solutions of a salt, carbohydrate, sugar alcohol, or an amino acid (such as saline or an aqueous amino acid solution), and suitable mixtures and/or buffered forms thereof, vegetable oils (such as olive oil), and injectable organic esters (such as ethyl oleate). Proper fluidity can be maintained, for example, by the use of coating materials, such as lecithin, by the maintenance of the required particle size in the case of dispersions, and by the use of surfactants.

Pharmaceutically acceptable carriers include sterile aqueous solutions or dispersions and sterile powders for the extemporaneous preparation of sterile injectable solutions or dispersions. The use of such media and agents for pharmaceutically active compounds is known in the art. Except insofar as any conventional media or agent is incompatible with the active compound, use thereof in the pharmaceutical compositions according to the present invention is contemplated.

Additional active compounds can be administered together with, before or after the TRMP8-agonist and the nAChR-agonist used according to the present invention or incorporated into the compositions. In one embodiment, the pharmaceutical composition described herein comprises a TRMP8-agonist as described above (including a hydrate, solvate, salt, complex, racemic mixture, diastereomer, enantiomer, or tautomer thereof or an isotopically enriched form of any of the foregoing), an nAChR-agonist as described above (including a hydrate, solvate, salt, complex, racemic mixture, diastereomer, enantiomer, or tautomer thereof or an isotopically enriched form of any of the foregoing), at least one additional active compound, and one or more pharmaceutically acceptable excipients.

The "additional active compound" (which is not a TRMP8-agonist as specified herein and not an nAChR-agonist as specified herein) may be selected from any compound which can be used for inhibiting weight gain (e.g., weight gain following smoking cessation or for reducing weight) and/or for treating obesity and/or obesity-related disorders. Exemplary additional active compounds in this respect include anti-obesity drugs which reduce appetite and/or decrease fat absorption.

Furthermore, in one embodiment, the administration of a pharmaceutical composition according to the present invention may be combined with dieting and/or exercising. For example, for better diet quality the consumption of energy-dense foods, such as those high in fat and sugars, can be reduced and/or the amount of dietary fiber can be increased. In a further embodiment, the administration of a pharmaceutical composition according to the present invention may be combined with a gastric balloon which may assist with weight loss, or with surgery to reduce stomach volume and/or bowel length.

The pharmaceutical composition described herein may comprise, in addition to the TRMP8-agonist as described above and the nAChR-agonist as described above, at least one, e.g., 1, 2, 3, 4, 5, 6, 7 or 8, additional active compounds. According to the present teaching, the at least additional active compound (e.g., the anti-obesity drug which reduces appetite and/or decreases fat absorption) may be formulated together with one or both of the TRMP8-agonist as described above and the nAChR-agonist as described above in a single pharmaceutical composition. Alternatively, the pharmaceutical composition may be structured as kit of parts, wherein the TRMP8-agonist is provided in a first formulation, the nAChR-agonist is provided in a second formulation and the at least one additional active compound (e.g., the anti-obesity drug which reduces appetite and/or decreases fat absorption) is provided in a third formulation, i.e., a third pharmaceutical composition. The first, second, and third pharmaceutical compositions may be combined prior to use. In other words, before administering the final pharmaceutical composition, a formulation comprising the additional active compound may be added to a mixture of the first pharmaceutical composition comprising the TRMP8-agonist and the second pharmaceutical composition comprising the nAChR-agonist. Alternatively, the present teaching envisages administering the TRMP8-agonist and the nAChR-agonist formulated in a first pharmaceutical composition and administering the at least one additional active compound formulated in a second pharmaceutical composition. The pharmaceutical compositions may be administered concomitantly or in succession. For example, the first pharmaceutical composition may be administered at a first point in time, the second pharmaceutical composition may be administered at a second point in time, and the third pharmaceutical composition may be administered at a third point in time, wherein the points in time may be separated by, for example, 0, or up to 1, 2, 3, 4, 5 or 10 min, up to 1, 2, 3, 4, 5 or 10 hours, up to 1, 2, 3, 4, 5 or 10 days, up to 1, 2, 3, 4, 5 or 10 weeks, up to 1, 2, 3, 4, 5 or 10 months or up to 1, 2, 3, 4, 5 or 10 years.

The compositions may also contain adjuvants such as preservatives, wetting agents, emulsifying agents, pH buffering agents, and dispersing agents. Prevention of the presence of microorganisms may be ensured by sterilization procedures and/or by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the active compounds, which may be used in a suitable hydrated form, and/or the pharmaceutical compositions according to the present invention, are formulated into pharmaceutically acceptable dosage forms by conventional methods known to those of skill in the art (cf., e.g., Remington, "The Science and Practice of Pharmacy" edited by Allen, Loyd V., Jr., $22^{nd}$ edition, Pharmaceutical Sciences, September 2012; Ansel et al., "Pharmaceutical Dosage Forms and Drug Delivery Systems", $7^{th}$ edition, Lippincott Williams & Wilkins Publishers, 1999.).

A pharmaceutical composition can be administered by a variety of methods known in the art. As will be appreciated by the skilled artisan, the route and/or mode of administration will vary depending upon the desired results. The pharmaceutical compositions containing one or more active compounds can be prepared with carriers that will protect the one or more active compounds against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such compositions are generally known to those skilled in the art. See, e.g., Sustained and Controlled Release Drug Delivery Systems, J. R. Robinson, ed., Marcel Dekker, Inc., New York, 1978.

To administer a compound used in the present invention by certain routes of administration, it may be necessary to coat the compound with, or co-administer the compound with, a material to prevent its inactivation. For example, the compound may be administered to an individual in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 7: 27(1984)).

Pharmaceutical compositions typically are sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

An injectable composition should be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof. Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the individuals to be treated; each unit contains a predetermined quantity of active compound calculated to produce the desired therapeutic effect in association with the required pharmaceutical carrier. The specification for the dosage unit forms used according to the present invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic/pharmaceutical formulations, compositions used according to the present invention include those suitable for enteral administration (such as oral or rectal) or parenteral administration (such as nasal, topical (including vaginal, buccal and sublingual)). The compositions may conveniently be presented in unit dosage form and may be prepared by any methods known in the art of pharmacy. The amount of active ingredient (in particular, the amount of each of the TRMP8-agonist and the nAChR-agonist used according to the present invention) which can be combined with a carrier material to produce a pharmaceutical composition (such as a single dosage form) will vary depending upon the individual being treated, and the particular mode of administration. The amount of active ingredient which can be combined with a carrier material to produce a single dosage form will generally be that amount of the composition which produces a therapeutic effect.

Generally, out of 100% (for the pharmaceutical formulations/compositions), the amount of each active ingredient (in particular, the amount of each of the TRMP8-agonist and the nAChR-agonist used according to the present invention, optionally together with other therapeutically active agents, if present in the pharmaceutical formulations/compositions) will range from about 0.01% to about 99%, preferably from about 0.1% to about 70%, most preferably from about 1% to about 30%, wherein the reminder is preferably composed of the one or more pharmaceutically acceptable excipients.

The amount of active ingredient, e.g., the amount of each of the TRMP8-agonist and the nAChR-agonist used according to the present invention, in a unit dosage form and/or when administered to an individual or used in therapy, may range from about 0.1 mg to about 1000 mg (for example, from about 1 mg to about 500 mg, such as from about 10 mg to about 200 mg) per unit, administration or therapy. In certain embodiments, a suitable amount of such active ingredient may be calculated using the mass or body surface area of the individual, including amounts of between about 1 mg/kg and 10 mg/kg (such as between about 2 mg/kg and 5 mg/kg), or between about 1 mg/m$^2$ and about 400 mg/m$^2$ (such as between about 3 mg/m$^2$ and about 350 mg/m$^2$ or between about 10 mg/m$^2$ and about 200 mg/m$^2$). For example, the nAChR-agonist may be administered in an amount of about 1 to 20 mg/kg body weight, such as about 2 to 15 mg/kg body weight, or about 5 to 10 mg/kg body weight. Suitable amounts of the TRPM8-agonist to be administered include about 1 to 50 µmol/kg body weight (such as about 2 to 40 µmol/kg body weight, about 5 to 30 µmol/kg body weight, or about 10 to 20 µmol/kg body weight) or about 1 to 20 mg/kg body weight (such as about 2 to 15 mg/kg body weight or about 5 to 10 mg/kg body weight).

Actual dosage levels of the active ingredients in the pharmaceutical compositions used according to the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start with doses of the compounds used according to the present invention at levels lower than that required in order to achieve the desired therapeutic effect and gradually increase the dosage until the desired effect is achieved. In general, a suitable daily dose of a composition used according to the present invention will be that amount of the compound which is the lowest dose effective to produce a therapeutic effect. Such an effective dose will generally depend upon the factors described above. It is preferred that administration be oral, intravenous, intramuscular, intraperitoneal, or subcutaneous, preferably administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound used according to the present invention to be administered alone, it is preferable to administer the compound as a pharmaceutical formulation/composition.

For oral administration, the pharmaceutical composition used according to the present invention can take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). Liquid preparations for oral administration can be in the form of, for example, solutions, syrups, or suspensions, or can be presented as a dry product for constitution with water or other suitable vehicle before use. Such liquid preparation can be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxycarbonates, sorbic acids). The preparations can also contain buffer salts, flavouring, coloring and sweetening agents as deemed appropriate. Preparations for oral administration can be suitably formulated to give controlled release of the pharmaceutical composition of the invention.

In one embodiment, the TRMP8-agonist and the nAChR-agonist are administered parenterally (e.g., intravenously, intramuscularly, or subcutaneously, preferably subcutaneously).

The pharmaceutical composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

For administration by inhalation, the pharmaceutical composition used according to the present invention is conveniently delivered in the form of an aerosol spray presentation from a pressurized pack or a nebulizer, with the use of a suitable propellant (e.g., dichlorodifluoromethane, trichlorofluoromethane, dichlorotetrafluoroethane, carbon dioxide, nitrogen, or other suitable gas). In the case of a pressurized aerosol, the dosage unit can be determined by providing a valve to deliver a metered amount. Capsules and cartridges of, for example, gelatine, for use in an inhaler or insufflator can be formulated containing a powder mix of the pharmaceutical composition used according to the present invention and a suitable powder base such as lactose or starch.

The pharmaceutical composition according to the present invention can be formulated for parenteral administration by injection, for example, by bolus injection or continuous infusion. In one embodiment, the compounds or compositions used according to the present invention may be administered by slow continuous infusion over a long period, such as more than 24 hours, in order to reduce toxic side effects. The administration may also be performed by continuous infusion over a period of from 2 to 24 hours, such as of from 2 to 12 hours. Such regimen may be repeated one or more times as necessary, for example, after 6 months or 12 months.

In yet another embodiment, the compounds or compositions used according to the present invention are administered by maintenance therapy, such as, e.g., once a week for a period of 6 months or more.

Formulations for injection can be presented in units dosage form (e.g., in phial, in multi-dose container), and with an added preservative. The pharmaceutical composition according to the present invention can take such forms as suspensions, solutions or emulsions in oily or aqueous vehicles, and can contain formulatory agents such as suspending, stabilizing, or dispersing agents. Alternatively, the agent can be in powder form for constitution with a suitable vehicle (e.g., sterile pyrogen-free water) before use. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Compositions according to the present invention which are suitable for vaginal administration also include pessaries, tampons, creams, gels, pastes, foams or spray formulations containing such carriers as are known in the art to be appropriate. Dosage forms for the topical or transdermal administration of compositions used according to the present invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

Therapeutic/pharmaceutical compositions can be administered with medical devices known in the art. For example, in a preferred embodiment, a therapeutic/pharmaceutical composition used according to the present invention can be administered with a needleless hypodermic injection device, such as the devices disclosed in U.S. Pat. Nos. 5,399,163; 5,383,851; 5,312,335; 5,064,413; 4,941,880; 4,790,824; or U.S. Pat. No. 4,596,556. Examples of well-known implants and modules useful in the present invention include those described in: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

Many other such implants, delivery systems, and modules are known to those skilled in the art. In certain embodiments, the compounds used according to the present invention can be formulated to ensure proper distribution in vivo. For example, the blood-brain barrier (BBB) excludes many highly hydrophilic compounds. To ensure that the compounds used according to the present invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, and thus enhance targeted drug delivery (see, e.g., V. V. Ranade (1989) *J. Clin. Pharmacol.* 29: 685). Exemplary targeting moieties include folate or biotin (see, e.g., U.S. Pat. No. 5,416,016 to Low et al.); mannosides (Umezawa et al., (1988) *Biochem. Biophys. Res. Commun.* 153: 1038); antibodies (P. G. Bloeman et al. (1995) *FEBS Lett.* 357: 140; M. Owais et al. (1995) *Antimicrob. Agents Chemother.* 39: 180); and surfactant protein A receptor (Briscoe et al. (1995) *Am. J. Physiol.* 1233: 134).

In one embodiment, the compounds used according to the present invention are formulated in liposomes. In a more preferred embodiment, the liposomes include a targeting moiety. In a most preferred embodiment, the compounds in the liposomes are delivered by bolus injection to a site proximal to the desired area. Such liposome-based composition should be fluid to the extent that easy syringability exists, should be stable under the conditions of manufacture and storage and should be preserved against the contaminating action of microorganisms such as bacteria and fungi.

A "therapeutically effective dosage" for therapy/treatment can be measured by objective responses which can either be complete or partial. A complete response (CR) is defined as no clinical, radiological or other evidence of a condition, disorder or disease. A partial response (PR) results from a reduction in disease of greater than 50%. Median time to progression is a measure that characterizes the durability of the objective tumor response.

A "therapeutically effective dosage" for therapy/treatment can also be measured by its ability to stabilize the progression of a condition, disorder or disease. The ability of a compound to act as agonist for TRPM8 or nAChR can be evaluated by using appropriate in vitro assays known to the skilled practitioner. Alternatively, the properties of a composition of the present invention can be evaluated by examining the ability of the composition in appropriate animal model systems known to the skilled practitioner (e.g. DIO mice). A therapeutically effective amount of the compounds used according to the present invention can cure, heal, alleviate, relieve, alter, remedy, ameliorate, improve or affect the condition, disorder or disease or the symptoms of the condition, disorder or disease or the predisposition toward the condition, disorder or disease in an individual. One of ordinary skill in the art would be able to determine such amounts based on such factors as the individual's size, the severity of the individual's symptoms, and the particular composition or route of administration selected.

The pharmaceutical composition according to the invention can also, if desired, be presented in a pack, or dispenser device which can contain one or more unit dosage forms containing the active compound. The pack can for example comprise metal or plastic foil, such as blister pack. The pack or dispenser device can be accompanied with instruction for administration.

Therapeutic Applications

Generally, the present invention demonstrates that the combination of TRMP8-agonist and nAChR-agonist as described herein is capable of inhibiting weight gain (e.g., or for reducing weight) and/or treat obesity and/or obesity-related disorders.

Thus, in one aspect, the present invention is directed at a composition as described herein (in particular, a pharmaceutical composition as described herein) for use in medicine.

In a further aspect, the present invention provides a composition as described herein (in particular, a pharmaceutical composition as described herein) for treating or preventing a disease selected from the group consisting of obesity and obesity-related disorders or conditions (such as diabetes (e.g., type 2 diabetes), hyperlipidemia (such as hypercholesterolemia and/or hypertriglyceridemia), renal disease (such as diabetic nephropathy), gallbladder disease (such as gall stones), eye disease (such as diabetic retinopathy), osteoarthritis, hypertension, advanced glycoxidation and/or lipoxidation end-product formation, stroke, metabolic syndrome, arteriosclerosis, coronary heart disease, gout, sleep apnea (such as obstructive sleep apnea), non-alcoholic fatty liver disease (NAFLD), and/or non-alcoholic steatohepatitis (NASH)).

In a further aspect, the present invention provides a composition as described herein (e.g., a pharmaceutical composition as described herein) for inhibiting weight gain. In one embodiment, the weight gain is caused by smoking cessation and/or for reducing weight.

In a further aspect, the present invention provides a method of treating or preventing a disease in a subject in need thereof, comprising administering to the subject a TRPM8-agonist and an nAChR-agonist (e.g., using a composition, in particular a pharmaceutical composition as described herein), wherein the disease is preferably selected from the group consisting of obesity and obesity-related disorders (such as diabetes (e.g., type 2 diabetes), hyperlipidemia (such as hypercholesterolemia and/or hypertriglyceridemia), renal disease (such as diabetic nephropathy), gallbladder disease (such as gall stones), eye disease (such as diabetic retinopathy), osteoarthritis, hypertension, advanced glycoxidation and/or lipoxidation end-product formation, stroke, metabolic syndrome, arteriosclerosis, coronary heart disease, gout, sleep apnea (such as obstructive sleep apnea), non-alcoholic fatty liver disease (NAFLD), and/or non-alcoholic steatohepatitis (NASH)).

In a further aspect, the present invention provides a method of inhibiting weight gain in a subject in need thereof, comprising administering to the subject a TRPM8-agonist and an nAChR-agonist (e.g., using a composition, in particular a pharmaceutical composition as described herein). In one embodiment, the weight gain is caused by smoking cessation and/or for reducing weight.

In any of the therapeutic applications described herein, the composition (in particular the pharmaceutical composition) may include printed instructions for use of the composition in the treatment or prevention of a disease.

The "additional active compound" (which is not a TRMP8-agonist as specified herein and not an nAChR-agonist as specified herein) may be selected from any compound which can be used for inhibiting weight gain (e.g., weight gain following smoking cessation or for reducing weight) and/or for treating obesity and/or obesity-related disorders. Exemplary additional active compounds in this respect include anti-obesity drugs which reduce appetite and/or decrease fat absorption.

Furthermore, in one embodiment, the administration of a pharmaceutical composition according to the present invention may be combined with dieting and/or exercising. For example, for better diet quality the consumption of energy-dense foods, such as those high in fat and sugars, can be reduced and/or the amount of dietary fiber can be increased. In a further embodiment, the administration of a pharmaceutical composition according to the present invention may be combined with a gastric balloon which may assist with weight loss, or with surgery to reduce stomach volume and/or bowel length.

In any of the above aspects (including the aspects relating to the composition of the invention, the aspects relating to the pharmaceutical composition of the invention, and the therapeutic aspects), the TRMP8-agonist may be selected from any of the TRMP8-agonists specified above, in particular, the TRMP8-agonists of any one of formulas (I), (Ia), (Ia'), (Ia$_1$), (Ia$_1$'), (Ia$_2$), (Ia$_2$'), (Ib), (Ib'), (Ib$_1$), (Ib$_1$'), (Ib$_2$), (Ib$_2$'), (Ic), (Ic'), (Ic$_1$), (Ic$_1$'), (Ic$_2$), (Ic$_2$'), (Id), (Id'), (Id$_1$), (Id$_1$'), (Id$_2$), (Id$_2$'), (Ie), (Ie'), (Ie$_1$), (Ie$_1$'), (Ie$_2$), (Ie$_2$'), (IIa), (IIb), (IIa$_1$), (IIb$_1$), (IIa$_2$), (IIb$_2$), (III), (III$_1$), (III$_2$), such as those depicted in Tables 1a, 1b, 1c, 1d, 1e, 2, 3, and 4, above, including their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof. For example, in any of the above aspects (including the aspects relating to the composition of the invention, the aspects relating to the pharmaceutical composition of the invention, and the therapeutic aspects), the TRMP8-agonist may be selected from N-(4-methoxyphenyl)-5-methyl-2-(1-methylethyl)cyclohexanecarboxamide (WS-12), N-ethyl-5-methyl-2-(1-methylethyl)cyclohexanecarboxamide (WS-3), ethyl 3-({[5-methyl-2-(propan-2-yl)cyclohexyl]carbonyl}amino) propanoate (also designated as ethyl 3-(p-menthane-3-carboxamido)acetate or WS-5), 5-methyl-2-(propan-2-yl)-N-[2-(pyridin-2-yl)ethyl]cyclohexanecarboxamide (also designated as N-(2-(pyridin-2-yl)ethyl)-3-p-menthanecarboxamide or FEMA-4549), N,2,3-trimethyl-2-(propan-2-yl) butanamide (also designated as WS-23), N-(2-hydroxyethyl)-2,3-dimethyl-2-(propan-2-yl)butanamide, N-(1,3-benzodioxol-5-yl)-2,3-dimethyl-2-(propan-2-yl) butanamide, 2,3-dimethyl-2-(propan-2-yl)-N-[2-(pyridin-2-yl)ethyl]butanamide, N-(2,3,4-trimethylpentan-3-yl)-1,3-benzodioxole-5-carboxamide, 3-(2-hydroxyphenyl)-6-(3- nitrophenyl)-3,4-dihydropyrimidin-2(1H)-one (also designated as icilin), 3-(2-hydroxyphenyl)-6-(3-methylphenyl)-3,4-dihydropyrimidin-2(1H)-one, 6-(3-chlorophenyl)-3-(2-hydroxyphenyl)-3,4-dihydropyrimidin-2(1H)-one, 3-(3-hydroxyphenyl)-6-(3-nitrophenyl)-3,4-dihydropyrimidin-2(1H)-one, 3-(2-methoxyphenyl)-6-(3-nitrophenyl)-3,4-dihydropyrimidin-2(1H)-one, 3-(3-methoxyphenyl)-6-(3-nitrophenyl)-3,4-dihydropyrimidin-2(1H)-one, 3-(2-hydroxy-4-methylphenyl)-6-(3-nitrophenyl)-3,4-dihydropyrimidin-2(1H)-one, 3-(2-hydroxy-3-methylphenyl)-6-(3-nitrophenyl)-3,4-dihydropyrimidin-2(1H)-one, 3-[2-(hydroxymethyl)phenyl]-6-(3-nitrophenyl)-3,4-dihydropyrimidin-2(1H)-one, 2-[4-(3-nitrophenyl)-2-oxo-3,6-dihydropyrimidin-1(2H)-yl]benzamide, 3-(2-chlorophenyl)-6-(3-nitrophenyl)-3,4-dihydropyrimidin-2(1H)-one, 3-(2-bromophenyl)-6-(3-nitrophenyl)-3,4-dihydropyrimidin-2(1H)-one, 3-(2-iodophenyl)-6-(3-nitrophenyl)-3,4-dihydropyrimidin-2(1H)-one, 3-(3-chlorophenyl)-6-(3-nitrophenyl)-3,4-dihydropyrimidin-2(1H)-one, 3-(3-bromophenyl)-6-(3-nitrophenyl)-3,4-dihydropyrimidin-2(1H)-one, and 3-(3-iodophenyl)-6-(3-nitrophenyl)-3,4-dihydropyrimidin-2(1H)-one (including their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof), e.g., a compound selected from the group consisting of 3-(2-hydroxyphenyl)-6-(3-nitrophenyl)-3,4-dihydropyrimidin-2(1H)-one (icilin), N-(4-methoxyphenyl)-5-methyl-2-(1-methylethyl)cyclohexanecarboxamide (WS-12), and N-ethyl-5-methyl-2-(1-methylethyl)cyclohexanecarboxamide (WS-3) (including their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof), in particular icilin (including its solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof).

In any of the above aspects (including the aspects relating to the composition of the invention, the aspects relating to the pharmaceutical composition of the invention, and the therapeutic aspects), the nAChR-agonist may be selected from any of the nAChR-agonists specified above, in particular, the nAChR-agonists of any one of formulas (IV), (IV$_1$), (IV$_2$), (V), (V'), (V$_1$), (V$_1$'), (V$_2$), (V$_2$'), (VI), (VI'), (VI$_1$), (VI$_1$'), (VI$_2$), (VI$_2$'), (VII), (VII$_1$), (VII$_2$), (VIII), (VIII'), (VIII$_1$), (VIII$_1$'), (VIII$_2$), (VIII$_2$'), (IX), (IX'), (IX), (IX$_1$'), (IX$_2$), (IX$_2$'), (X), (XI), (XI), (XI'), (XII), (XII'), (XI$_2$), (XI$_2$'), (XII), (XII$_1$), (XII$_2$), (XIII), (XIII'), (XIII$_1$), (XIII$_1$'), (XIII$_2$), and (XIII$_2$') such as those depicted in Tables 5, 6, 7, 8, 9, 10, 11, 12, 13, and 14, above, including their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof. For example, in any of the above aspects (including the aspects relating to the composition of the invention, the aspects relating to the pharmaceutical composition of the invention, and the therapeutic aspects), the nAChR-agonist may be selected from a dimethylphenylpiperazinium (DMPP) salt, cytisine, 4-(trifluoromethyl)-10-azatricyclo[6.3.1.0$^{2,7}$]dodeca-2,4,6-triene (CP-601932), varenicline, nicotine, 6-[5-fluoro-2-(pyridin-3-yl)phenoxy]-3-azabicyclo[3.2.1]octane (PF-4575180), epibatidine, acetylcholine, N-methylcarbamylcholine, 3-methyl-5-[(2S)-1-methylpyrrolidin-2-yl]-1,2-oxazole (ABT-418), 3-[(3E)-3-[(2,4-dimethoxyphenyl)methylidene]-5,6-dihydro-4H-pyridin-2-yl]pyridine (GTS-21), lobeline, and 4-{[2-(1-methyl-2-pyrrolidinyl)ethyl]thio}phenol (SIB-1553A) (including their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof), such as a compound selected from the group consisting of a DMPP salt, cytisine, and nicotine (including their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof), in particular a DMPP salt.

In one embodiment of all aspects specified above (including the aspects relating to the composition of the invention, the aspects relating to the pharmaceutical composition of the invention, and the therapeutic aspects), it is preferred that (i) the TRMP8-agonist is selected from a TRMP8-agonist having formula (III), (III$_1$), (III$_2$), (Ia), (Ia'), (Ia$_1$), (Ia$_1$'), (Ia$_2$), or (Ia$_2$') (including their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof) and (ii) the nAChR-agonist is selected from a nAChR-agonist having formula (IV), (IV$_1$), (IV$_2$), (V), (V'), (V$_1$), (V$_1$'), (V$_2$), or (V$_2$') (including their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof).

In a further embodiment of all aspects specified above (including the aspects relating to the composition of the invention, the aspects relating to the pharmaceutical composition of the invention, and the therapeutic aspects), it is preferred that (i) the TRMP8-agonist is selected from N-(4-methoxyphenyl)-5-methyl-2-(1-methylethyl)cyclohexanecarboxamide (WS-12), N-ethyl-5-methyl-2-(1-methylethyl)cyclohexanecarboxamide (WS-3), ethyl 3-({[5-methyl-2-(propan-2-yl)cyclohexyl]carbonyl}amino) propanoate (also designated as ethyl 3-(p-menthane-3-carboxamido)acetate or WS-5), 5-methyl-2-(propan-2-yl)-N-[2-(pyridin-2-yl)ethyl]cyclohexanecarboxamide (also designated as N-(2-(pyridin-2-yl)ethyl)-3-p-menthanecarboxamide or FEMA-4549), N,2,3-trimethyl-2-(propan-2-yl)butanamide (also designated as WS-23), N-(2-hydroxyethyl)-2,3-dimethyl-2-(propan-2-yl)butanamide, N-(1,3-benzodioxol-5-yl)-2,3-dimethyl-2-(propan-2-yl) butanamide, 2,3-dimethyl-2-(propan-2-yl)-N-[2-(pyridin-2-yl)ethyl]butanamide, N-(2,3,4-trimethylpentan-3-yl)-1,3-benzodioxole-5-carboxamide, 3-(2-hydroxyphenyl)-6-(3- nitrophenyl)-3,4-dihydropyrimidin-2(1H)-one (also designated as icilin), 3-(2-hydroxyphenyl)-6-(3-methylphenyl)-3,4-dihydropyrimidin-2(1H)-one, 6-(3-chlorophenyl)-3-(2-hydroxyphenyl)-3,4-dihydropyrimidin-2(1H)-one, 3-(3-hydroxyphenyl)-6-(3-nitrophenyl)-3,4-dihydropyrimidin-2(1H)-one, 3-(2-methoxyphenyl)-6-(3-nitrophenyl)-3,4-dihydropyrimidin-2(1H)-one, 3-(3-methoxyphenyl)-6-(3-nitrophenyl)-3,4-dihydropyrimidin-2(1H)-one, 3-(2-hydroxy-4-methylphenyl)-6-(3-nitrophenyl)-3,4-dihydropyrimidin-2(1H)-one, 3-(2-hydroxy-3-methylphenyl)-6-(3-nitrophenyl)-3,4-dihydropyrimidin-2(1H)-one, 3-[2-(hydroxymethyl)phenyl]-6-(3-nitrophenyl)-3,4-dihydropyrimidin-2(1H)-one, 2-[4-(3-nitrophenyl)-2-oxo-3,6-dihydropyrimidin-1(2H)-yl]benzamide, 3-(2-chlorophenyl)-6-(3-nitrophenyl)-3,4-dihydropyrimidin-2(1H)-one, 3-(2-bromophenyl)-6-(3-nitrophenyl)-3,4-dihydropyrimidin-2(1H)-one, 3-(2-iodophenyl)-6-(3-nitrophenyl)-3,4-dihydropyrimidin-2(1H)-one, 3-(3-chlorophenyl)-6-(3-nitrophenyl)-3,4-dihydropyrimidin-2(1H)-one, 3-(3-bromophenyl)-6-(3-nitrophenyl)-3,4-dihydropyrimidin-2(1H)-one, and 3-(3-iodophenyl)-6-(3-nitrophenyl)-3,4-dihydropyrimidin-2(1H)-one (including their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof), e.g., a compound selected from the group consisting of 3-(2-hydroxyphenyl)-6-(3-nitrophenyl)-3,4-dihydropyrimidin-2(1H)-one (icilin), N-(4-methoxyphenyl)-5-methyl-2-(1-methylethyl)cyclohexanecarboxamide (WS-12), and N-ethyl-5-methyl-2-(1-methylethyl)cyclohexanecarboxamide (WS-3), in particular icilin; and (ii) the nAChR-agonist is selected from a dimethylphenylpiperazinium (DMPP) salt, cytisine, 4-(trifluoromethyl)-10-azatricyclo[6.3.1.0$^{2,7}$] dodeca-2,4,6-triene (CP-601932), varenicline, nicotine, 6-[5-fluoro-2-(pyridin-3-yl)phenoxy]-3-azabicyclo[3.2.1] octane (PF-4575180), epibatidine, acetylcholine, N-methylcarbamylcholine, 3-methyl-5-[(2S)-1-methylpyrrolidin-2-yl]-1,2-oxazole (ABT-418), 3-[(3E)-3-[(2,4-dimethoxyphenyl)methylidene]-5,6-dihydro-4H-pyridin-2-yl]pyridine (GTS-21), lobeline, and 4-{[2-(1-methyl-2-pyrrolidinyl)ethyl]thio}phenol (SIB-1553A) (including their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof), such as a compound selected from the group consisting of a DMPP salt, cytisine, and nicotine (including their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof), in particular a DMPP salt.

Other features and advantages of the present invention will be apparent from the following examples which are included to demonstrate preferred embodiments of the present invention but which do not limit the present invention. Rather, in light of the present disclosure, the skilled person will appreciate that many changes can be made in the specific embodiments which are disclosed and still obtain a like or similar result without departing from the scope of the invention.

EXAMPLES

Materials and Methods

Animals, Diet and Treatment

Six- to eight-week-old male C57Bl/6 mice were given ad libitum access to a high-fat, high-sugar diet comprising 58% kcal fat (D12331; Research Diets, New Brunswick, N.J.). The mice had free access to water and were maintained at 23±1° C., constant humidity and on a 12-h light-dark cycle. Mice were maintained under these conditions for a minimum of 20 weeks before study initiation. At study start, mice were randomized into groups matched for body weight and body composition. Compounds were administered subcutaneously 1 h before the onset of the dark phase. Co-administration of compounds was administered by single formulated injections. Assessment of energy intake, energy expenditure and home-cage activity were performed using an indirect calorimetry system (TSE Phenotmaster, TSE Systems, Bad Homburg, Germany).

Glucose Metabolism

Glucose tolerance was analyzed in 6 h fasted mice, following an intraperitoneal challenge with 1.5 g glucose per kg body weight. Glucose levels were measured in blood sampled from the tail veins before (0 min) and at 15, 30, 60 and 120 min post injection. To measure glucose-stimulated insulin secretion blood was collected from tail veins into EDTA-coated microvette tubes (Sarstedt) at time points 0, 15 and 60 min post glucose injection. Insulin sensitivity was assessed in 6 h fasted mice following an intraperitoneal injection of 0.7 U of insulin (Actrapid) per kg body weight. Blood glucose levels were measured before (0 min) and at 15, 30, 60 and 120 minutes after the insulin injection. Insulin was measured with commercially available kit (ALPCO Diagnostics, Salem, N.H.) per the manufacturer's instructions.

The abbreviations used in the present invention have the following meanings:

d=day
mg/dl=milligram/deciliter
h=hour
kg=kilogram
min=minute

Example 1—Effects of a Monotherapy (Using the nAChR-Agonist DMPP Alone) on Obese Mice To assess the effect of DMPP alone on the body weight and food intake, diet-induced obese (DIO) male mice were treated 14 days with vehicle (control) or DMPP (1 mg/kg, 5 mg/kg or 10 mg/ml). Compounds were administered by daily subcutaneous injections. The results of these treatments are shown in FIGS. 2(A) and 2(B) (control: white circle; or DMPP: 1 mg/kg (white square), 5 mg/kg (white triangle) or 10 mg/ml (black triangle)). The data presented in these figures demonstrate that the dose-dependent weight lowering effect results from a reduction in food intake.

We also investigated the effect of DMPP alone on glucose tolerance and area under the curve (AUC). Glucose tolerance was assessed following 7-days treatment of DIO male mice with vehicle (control) or DMPP (1 mg/kg, 5 mg/kg or 10 mg/ml). Compounds were administered by daily subcutaneous injections. The results of these treatments are shown in FIGS. 2(C) and 2(D) (control: white circle; DMPP: 1 mg/kg (white square), 5 mg/kg (white triangle) or 10 mg/ml (black triangle)). The data presented in these figures demonstrate that the dose-dependent improvement in glucose tolerance is compound specific virtue.

Example 2—Effects of a Monotherapy (Using the TRPM8-Agonist Icilin Alone) on Obese Mice To assess the effect of icilin alone on the body weight and food intake, DIO male mice were treated 16 days with vehicle (control) or icilin (0.6 mg/kg or 6 mg/kg). The results of these treatments are shown in FIGS. 3(A) and 3(B) (control: white circle; icilin: 0.6 mg/kg (star) or 6 mg/kg (black circle)). The effect on energy expenditure was investigated by a 5-days treatment of DIO male mice with vehicle (control) or icilin (6 mg/kg). Compounds were administered by daily subcutaneous injections. The results of these treatments are shown in FIG. 3(C) (control: white bar; icilin: black bar). The data presented in FIG. 3(A) to (C) demonstrate that the dose-dependent weight loss after icilin treatment results from an increased energy expenditure.

Glucose tolerance was assessed following 7-days treatment of DIO male mice with vehicle (control) or icilin (6 mg/kg). The results are shown in FIG. 3(D) (control: white; icilin: black). Fasting glucose was assessed following 23-days treatment of DIO male mice with vehicle (control) or icilin (6 mg/kg). Compounds were administered by daily subcutaneous injections. The results are shown in FIG. 3(E) (control: white bar; icilin: black bar). The data presented in FIGS. 3(D) and (E) demonstrate that icilin does not lead to a short term improvement in glucose tolerance (7d treatment), but a long-term treatment (23d) results in improved fasting glucose levels.

Example 3—Effects of a Combination Therapy (Using the nAChR-Agonist DMPP Together with the TRPM8-Agonist Icilin) on Obese Mice To assess the effect of the combination therapy on the body weight, DIO male mice were treated 4 days with vehicle (control), DMPP alone (10 mg/kg), icilin alone (5 mg/kg) or DMPP (10 mg/ml)+icilin (5 mg/kg). Compounds were administered by daily subcutaneous injections. The results are shown in FIG. 4(A) (control: white circle; DMPP alone: grey diamond; icilin alone: black star; DMPP+icilin: checkered square). Glucose tolerance was assessed following 7-days treatment of DIO male mice with vehicle (control), DMPP alone (10 mg/kg), icilin alone (5 mg/kg) or DMPP (10 mg/ml)+icilin (5 mg/kg). Compounds were administered by daily subcutaneous injections. The results are shown in FIG. 4(B) to (F) (Fig. (B) to (D): control: white circle, DMPP alone: grey diamond; icilin alone: black star; DMPP+icilin: checkered square). The data presented in FIGS. 4(A) and (F) demonstrate that the combination of DMPP and icilin results in (i) an synergistically increase of the weight loss, (ii) better glucose tolerance, and (iii) higher insulin sensitivity. Thus, it has been shown that the combination of an nAChR-agonist with a TRPM8-agonist improves multiple aspects of glucose metabolism.

Example 4—Effects of a Combination Therapy (Using the nAChR-Agonist DMPP Together with the TRPM8-Agonist Icilin) on Hepatic Lipid Accumulation To assess the effect of the combination therapy on hepatic lipid accumulation, DIO male mice were treated 2-weeks with vehicle, DMPP (10 mg/kg), icilin (5 mg/kg) or DMPP (10 mg/ml)+icilin (5 mg/kg). Compounds were administered by daily subcutaneous injections. The results are shown in FIG. 5, wherein FIG. 5(A) demonstrates the effect on non-alcoholic fatty liver disease activity score (NAFLD Score) and FIG. 5(B) demonstrates the effect on histological H&E staining of livers from representative mice. As can be seen form the results presented in FIG. 5, the combination of DMPP and icilin reverses hepatic steatosis (diet-induced fatty liver disease). Thus, it has been shown that the lipid metabolism is improved by a combination of an nAChR-agonist with a TRPM8-agonist.

Example 5—Effects of a Combination Therapy (Using an nAChR-Agonist DMPP and a TRPM8-agonist N-(4-methoxyphenyl)-5-methyl-2-(1-methylethyl)cyclohexanecarboxamide (also Designated as WS-12)) on Obese Mice To assess the effect of the combination therapy on the body weight, DIO male mice were treated for 6 consecutive days with either vehicle (control, black circles), the nAChR-agonist DMPP alone (5 mg/kg; blue circles), the TRMP8-agonist N-(4-methoxyphenyl)-5-methyl-2-(1-methylethyl)cyclohexanecarboxamide (also designated as WS-12) alone (20 nmol/kg; 5 mg/kg; red circles), or the combination of DMPP (5 mg/kg)+N-(4-methoxyphenyl)-5-methyl-2-(1-methylethyl)cyclohexanecarboxamide (5 mg/kg) (white circles). Compounds were administered by daily subcutaneous injections in a volume of 5 ul/g body weight. The results are shown in FIG. 6(A) (control: black circle; DMPP alone: light grey circle; N-(4-methoxyphenyl)-5-methyl-2-(1-methylethyl)cyclohexanecarboxamide (also designated as WS-12) alone (blue circle); DMPP+N-(4-methoxyphenyl)-5-methyl-2-(1-methylethyl)cyclohexanecarboxamide (also designated as WS-12) (white circle). FIG. 6B shows the percent weight loss at the end of the study (day 6) with vehicles controls (black bar), DMPP (blue bar), WS-12 (red bar) or the combination of DMPP and WS-12 (white bar). To demonstrate the synergistic effect, the bar for the combination therapy shows the effects of both monotherapies (dashed horizontal line).

In summary, these data show that the combination of DMPP and WS-12 synergistically lowers body weight gain. The body weight lowering effect of the combination therapy is greater as expected by the sum of the two respective mono therapies.

The invention claimed:

1. A composition comprising 3-(2-hydroxyphenyl)-6-(3-nitrophenyl)-3,4-dihydropyrimidin-2(1H)-one (icilin) or a solvate, salt, complex, or prodrug thereof and a dimethylphenylpiperazinium (DMPP) salt or an analogue thereof.

2. The composition of claim 1, which is in the form of a kit comprising a first container including the 3-(2-hydroxyphenyl)-6-(3-nitrophenyl)-3,4-dihydropyrimidin-2(1H)-one (icilin) or a solvate, salt, complex, or prodrug thereof and a second container including the dimethylphenylpiperazinium (DMPP) salt or an analogue thereof.

3. The composition of claim 1, wherein the dimethylphenylpiperazinium (DMPP) salt or an analogue thereof has a general formula:

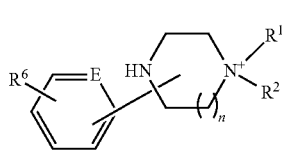

wherein $R^1$ and $R^2$ are each independently selected from the group consisting of H and alkyl, wherein the alkyl group is optionally substituted; $R^6$ is selected from the group consisting of absent, alkyl, halogen, nitro, cyano, isocyano, cyanato, isocyanato, thiocyanato, isothiocyanato, azido, amino, —S(O)$_{1-2}$-(amino), —OS(O)$_{1-2}$-(amino), -(imino)-S(O)$_{1-2}$-(amino), and —Z—$R^{11}$, wherein Z is —O—, —S(O)$_{0-2}$—, —S(O)$_{1-2}$O—, —OS(O)$_{0-2}$—, —OS(O)$_{1-2}$O—, -(imino)-O—, -(imino)-S(O)$_{1-2}$—, -(imino)-S(O)$_{1-2}$—O—, —C(=X)—, —C(=X)X—, —XC(=X)—, and —XC(=X)X—, wherein the alkyl group is optionally substituted, each X is independently selected from O, S, and imino, and $R^{11}$ is selected from hydrogen, alkyl, alkenyl, alkynyl, cycloalkyl, heterocyclyl, aryl, and heteroaryl, wherein each of the alkyl, alkenyl, alkynyl, cycloalkyl, heterocyclyl, aryl, and heteroaryl groups is optionally substituted; E is N or CH; and n is 1 or 2.

4. The composition of claim 1, further comprising one or more pharmaceutically acceptable excipients.

5. The composition of claim 1 for use in medicine.

6. The composition of claim 5, further including printed instructions for use of the composition in the treatment or prevention of a disease.

7. The composition of claim 5 for treating or preventing a disease selected from the group consisting of obesity and obesity-related disorders or conditions.

* * * * *